(12) United States Patent
Van Zandt et al.

(10) Patent No.: US 7,361,671 B2
(45) Date of Patent: Apr. 22, 2008

(54) SUBSTITUTED HETEROARYLALKANOIC ACIDS

(75) Inventors: Michael C. Van Zandt, Guilford, CT (US); Leo Geraci, Clinton, CT (US)

(73) Assignee: The Institute for Pharmaceutical Discovery, Inc., Brandford, CT (US)

( * ) Notice: Subject to any disclaimer, the term of this patent is extended or adjusted under 35 U.S.C. 154(b) by 0 days.

(21) Appl. No.: 10/295,414

(22) Filed: Nov. 14, 2002

(65) Prior Publication Data
US 2003/0166668 A1 Sep. 4, 2003

Related U.S. Application Data

(60) Provisional application No. 60/378,626, filed on May 7, 2002, provisional application No. 60/336,055, filed on Nov. 15, 2001.

(51) Int. Cl.
*A61K 31/4436* (2006.01)
*A61K 31/443* (2006.01)
*C07D 417/12* (2006.01)
*C07D 417/14* (2006.01)
*C07D 417/04* (2006.01)

(52) U.S. Cl. .................. 514/338; 514/333; 546/270.1; 546/256

(58) Field of Classification Search ............. 546/270.1, 546/323, 342, 301, 302, 303, 321, 339, 286, 546/322, 256; 514/338, 345, 277, 354, 256
See application file for complete search history.

(56) References Cited

U.S. PATENT DOCUMENTS 5,990,314 A * 11/1999 Daines ...................... 546/341

FOREIGN PATENT DOCUMENTS

WO   WO 9322285 A1 * 11/1993
WO   WO 0123383 A1 *  4/2001

OTHER PUBLICATIONS

Mylari BL et al. J. Med. Chem. (1992) 35, 457-465.*

* cited by examiner

*Primary Examiner*—Patricia L. Morris
(74) *Attorney, Agent, or Firm*—McDonnell Boehnen Hulbert & Berghoff LLP

(57) ABSTRACT

Disclosed are substituted heteroarylalkanoic acids acids of the following formula D-A-C(O)R', where D, A, and R' are defined herein. These compounds are useful in the treatment of chronic complications arising from diabetes mellitus. Also disclosed are pharmaceutical compositions containing the compounds and methods of treatment employing the compounds, as well as methods for their synthesis.

36 Claims, No Drawings

SUBSTITUTED HETEROARYLALKANOIC ACIDS

This application claims benefit of U.S. Provisional Application Ser. No. 60/336,055, filed Nov. 15, 2001, and U.S. Provisional Application Ser. No. 60/378,626, filed May 7, 2002.

BACKGROUND OF INVENTION

1. Field of the Invention

The present invention relates to heteroarylalkanoic acids and derivatives thereof. More specifically, it relates to such compounds capable of inhibiting aldose reductase and lowering uric acid levels.

2. Description of the Related Art

The use of aldose reductase inhibitors (ARIs) for the treatment of diabetic complications is well known. The complications arise from elevated levels of glucose in tissues such as the nerve, kidney, retina and lens that enters the polyol pathway and is converted to sorbitol via aldose reductase. Because sorbitol does not easily cross cell membranes, it accumulates inside certain cells resulting in changes in osmotic pressure, alterations in the redox state of pyridine nucleotides (i.e. increased NADH/NAD$^+$ ratio) and depleted intracellular levels of myoinositol. These biochemical changes, which have been linked to diabetic complications, can be controlled by inhibitors of aldose reductase.

Uric acid containing deposits (also known as trophi) resulting from unphysiologically elevated plasma uric acid levels tend to occur in various tissues throughout the body, leading to the disease condition known as gout and gouty arthritis. Uric acid containing deposits in such conditions may occur in cartilage, bone, bursae, tendons, connective tissue overlying bony prominences, as well as, subcutaneously and in the area of kidney. Elevated blood uric acid levels also occur in number of other disease conditions including myeloid leukemia, myeloid dysplasia, pernicious anemia, psoriasis, diabetes mellitus and renal disease.

Acute gout responds to colchicine. Nonsteroidal anti-inflammatory agents are also useful in acute attacks. Long-term therapy is directed to preventing hyperuricemia by giving uriosuric drugs. Patients with gout have a tendency to form uric acid kidney stones.

Treatment for gout consists of the administration of anti-inflammatory agents, dietary modifications, and the use of drugs that diminish uric acid formation, as well as drugs that enhance excretion of uric acid by the kidney. The latter drugs are the uricosuric agents, some of which act as competitive inhibitors of both uric acid transport and the transport of other organic anions.

One of the peculiar characteristics of the uric acid transport system is that, although the net activity of tubular function is reabsorption of uric acid, the molecule is both secreted and reabsorbed during its passage through the nephron. The secretory and reabsorptive mechanisms vary in importance along the proximal tubule, with reabsorption dominating in the S1 and S3 segments and secretion dominating in the S2 segment. As a consequence of this bidirectional transport, drugs that inhibit uric acid transport may decrease rather than increase the excretion of uric acid. Obviously, such an effect compromises their therapeutic usefulness.

SUMMARY OF THE INVENTION

This invention provides heterarylalkanoic acids that interact with and inhibit aldose reductase. Such compounds preferably have high affinity for aldose reductase. Such compounds also preferably have high selectivity for the enzyme. More preferably, they have both high affinity and high selectivity for the enzyme.

In a broad aspect, the invention provides compounds of Formula I

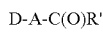   I or a pharmaceutically acceptable salt thereof wherein

D is a heteroaryl group selected from the group consisting of

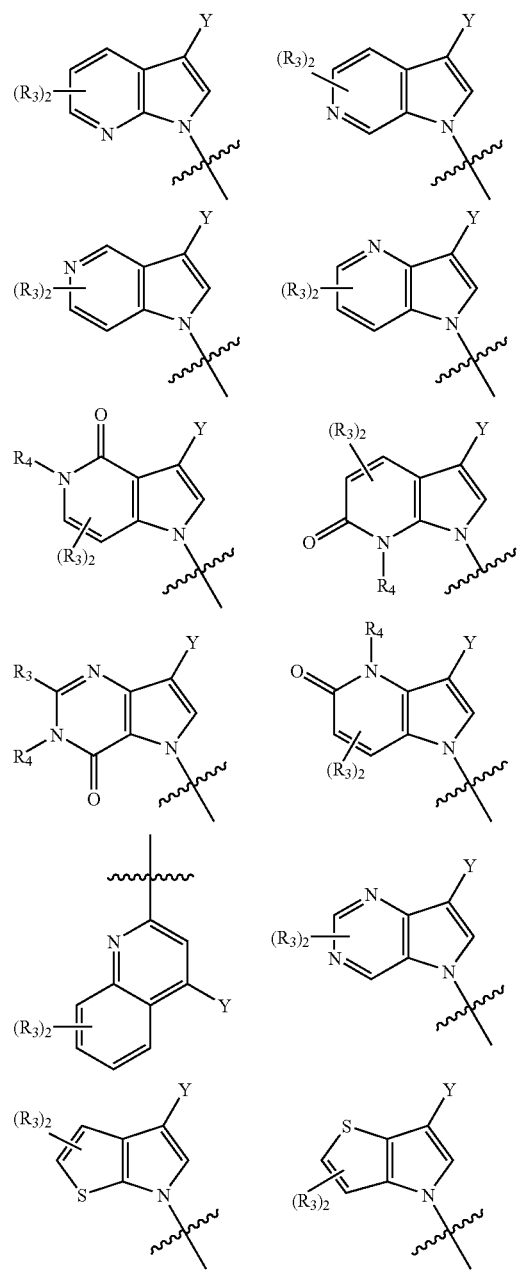

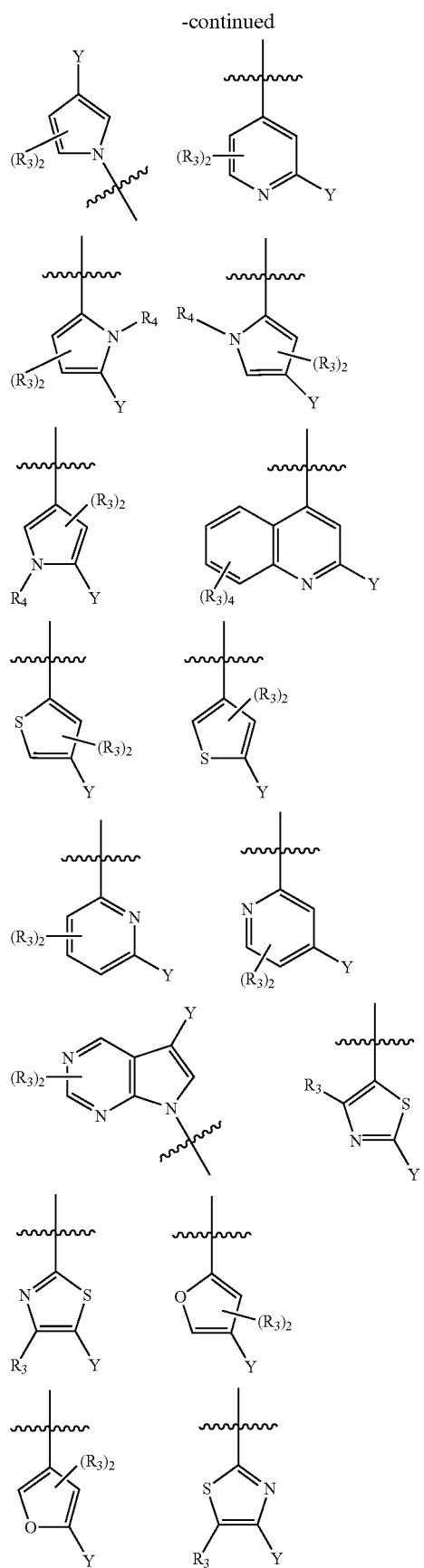
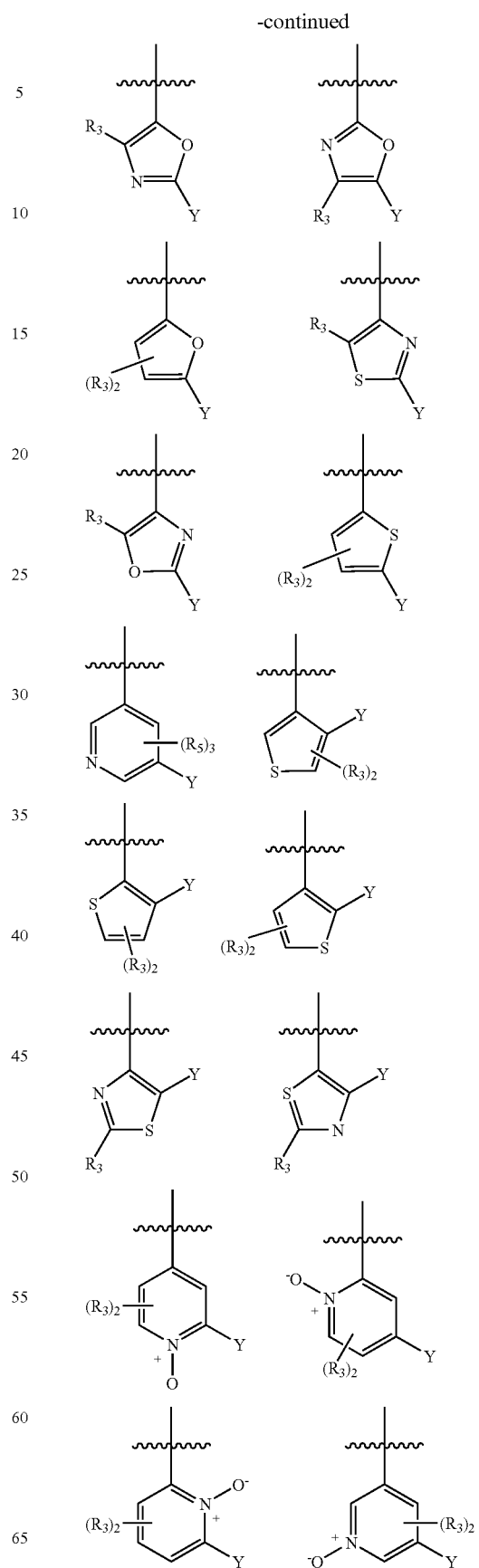

-continued

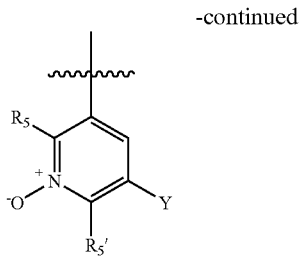

where
Y is -Z-Ar where
  Z is a bond, O, S, C(O)NH, or $C_1$-$C_6$ alkylene optionally substituted with $C_1$-$C_2$ alkyl; and
  Ar represents
    an aryl or aryl($C_1$-$C_6$)alkyl group, where the aryl portion is optionally substituted with up to 5 groups independently selected from
      (1) halogen, ($C_1$-$C_6$)alkyl, hydroxy, ($C_1$-$C_6$)haloalkyl, ($C_2$-$C_6$)haloacetyl, cyano, nitro, ($C_1$-$C_6$)alkanoyl, ($C_1$-$C_6$)alkylthio, ($C_1$-$C_6$)haloalkylthio, $OR_7$, $SR_7$, $S(O)R_7$, $S(O)_2R_7$ and $N(R_7)_2$ wherein each $R_7$ is independently hydrogen, $C_1$-$C_6$ alkyl, $C_1$-$C_6$ haloalkyl, or $C_1$-$C_6$ haloalkoxy; and
      (2) phenyl, pyridyl, furyl, and thienyl, each of which is optionally substituted with one, two, or three groups independently selected from halogen, ($C_1$-$C_6$)alkyl, hydroxy, halogen, ($C_1$-$C_6$)haloalkyl, ($C_2$-$C_6$)haloacetyl, cyano, nitro, ($C_1$-$C_6$)alkanoyl, ($C_1$-$C_6$)alkylthio, ($C_1$-$C_6$)haloalkylthio, $OR_{17}$, $SR_{17}$, $S(O)R_{17}$, $S(O)_2R_{17}$ and $N(R_{17})_2$ wherein each $R_{17}$ is independently hydrogen, $C_1$-$C_6$ alkyl, $C_1$-$C_6$ haloalkyl, or $C_1$-$C_6$ haloalkoxy;
    a heteroaryl or heteroaryl($C_1$-$C_6$)alkyl group, where the heteroaryl portion is optionally substituted by one, two or three groups independently selected from
      (1) halogen, ($C_1$-$C_6$)alkyl, hydroxy, ($C_1$-$C_6$)haloalkyl, ($C_2$-$C_6$)haloacetyl, cyano, nitro, ($C_1$-$C_6$)alkanoyl, ($C_1$-$C_6$)alkylthio, ($C_1$-$C_6$)haloalkylthio, $OR_{27}$, $SR_{27}$, $S(O)R_{27}$, $S(O)_2R_{27}$ and $N(R_{27})_2$ wherein each $R_{27}$ is independently hydrogen, $C_1$-$C_6$ alkyl, $C_1$-$C_6$ haloalkyl, and $C_1$-$C_6$ haloalkoxy; and
      (2) phenyl, pyridyl, furyl, and thienyl, each of which is optionally substituted with one, two, or three groups independently selected from halogen, ($C_1$-$C_6$)alkyl, hydroxy, halogen, ($C_1$-$C_6$)haloalkyl, ($C_2$-$C_6$)haloacetyl, cyano, nitro, ($C_1$-$C_6$)alkanoyl, ($C_1$-$C_6$)alkylthio, ($C_1$-$C_6$)haloalkylthio, $OR_{37}$, $SR_{37}$, $S(O)R_{37}$, $S(O)_2R_{37}$ and $N(R_{37})_2$ wherein each $R_{37}$ is independently hydrogen, $C_1$-$C_6$ alkyl, $C_1$-$C_6$ haloalkyl, or $C_1$-$C_6$ haloalkoxy;
$R_3$ is hydrogen, halogen, hydroxy, ($C_1$-$C_6$)alkyl, ($C_1$-$C_6$)haloalkyl, amino, ($C_1$-$C_6$)alkylamino, di($C_1$-$C_6$)alkylamino, aryl, aryl alkyl, —$SR_{15}$ or —$OR_{15}$, where $R_{15}$ is ($C_1$-$C_6$)alkyl, aryl, or aryl($C_1$-$C_6$)alkyl where each aryl is optionally mono-, di-, or trisubstituted with halogen, ($C_1$-$C_6$)alkyl, hydroxy, halogen, ($C_1$-$C_6$)haloalkyl, ($C_2$-$C_6$)haloacetyl, cyano, nitro, ($C_1$-$C_6$)alkanoyl, ($C_1$-$C_6$)alkylthio, ($C_1$-$C_6$)haloalkylthio, $OR_7$, $SR_7$, $S(O)R_7$, $S(O)_2R_7$ and $N(R_7)_2$;
$R_4$ is hydrogen, halogen, hydroxy, ($C_1$-$C_6$)alkoxy, ($C_1$-$C_6$)alkyl, ($C_1$-$C_6$)alkanoyl, or benzoyl where the phenyl portion is optionally mono-, di-, or trisubstituted with halogen, ($C_1$-$C_6$)alkyl, hydroxy, halogen, ($C_1$-$C_6$)haloalkyl, ($C_2$-$C_6$)haloacetyl, cyano, nitro, ($C_1$-$C_6$)alkanoyl, ($C_1$-$C_6$)alkylthio, ($C_1$-$C_6$)haloalkylthio, $OR_7$, $SR_7$, $S(O)R_7$, $S(O)_2R_7$ and $N(R_7)_2$;
$R_5$ is hydrogen, halogen, hydroxy, ($C_1$-$C_6$)alkoxy, ($C_1$-$C_6$)alkyl, halo($C_1$-$C_6$)alkyl, hydroxy, amino, mono- or di($C_1$-$C_6$)alkylamino, aryl alkyl, or aryl where each aryl is optionally substituted with up to three groups independently selected from halogen, ($C_1$-$C_6$)alkyl, hydroxy, halogen, ($C_1$-$C_6$)haloalkyl, ($C_2$-$C_6$)haloacetyl, cyano, nitro, ($C_1$-$C_6$)alkanoyl, ($C_1$-$C_6$)alkylthio, ($C_1$-$C_6$)haloalkylthio, $OR_7$, $SR_7$, $S(O)R_7$, $S(O)_2R_7$ and $N(R_7)_2$;
$R_6$ is hydrogen, ($C_1$-$C_6$)alkyl, oxo, ($C_3$-$C_7$)cycloalkyl, ($C_3$-$C_7$)cycloalkyl ($C_1$-$C_6$)alkyl or aryl($C_1$-$C_6$)alkyl where the aryl portion is optionally mono-, di-, or trisubstituted with halogen, ($C_1$-$C_6$)alkyl, hydroxy, halogen, ($C_1$-$C_6$)haloalkyl, ($C_2$-$C_6$)haloacetyl, cyano, nitro, ($C_1$-$C_6$)alkanoyl, ($C_1$-$C_6$)alkylthio, ($C_1$-$C_6$)haloalkylthio, $OR_7$, $SR_7$, $S(O)R_7$, $S(O)_2R_7$ and $N(R_7)_2$;
A is a $C_1$-$C_4$ alkylene group optionally substituted with $C_1$-$C_2$ alkyl or mono- or disubstituted with halogen; and
R' is hydroxy, benzyloxy, di($C_1$-$C_6$)alkylaminoethyloxy, acetoxymethyl, pivaloyloxymethyl, phthalidoyl, ethoxycarbonyloxyethyl, 5-methyl-2-oxo-1,3-dioxol-4-yl methyl, or ($C_1$-$C_6$)alkoxy optionally substituted by N-morpholino or di($C_1$-$C_6$)alkylamino.

In another aspect, the invention provides methods for preparing such compounds.

The compounds of Formula I inhibit aldose reductase. Since aldose reductase is critical to the production of high levels of sorbitol in individuals with diabetes, inhibitors of aldose reductase are useful in preventing and/or treating various complications associated with diabetes. The compounds of the invention are therefore effective for the treatment of diabetic complications as a result of their ability to inhibit aldose reductase.

Thus, in another aspect, the invention provides methods of preventing or alleviating chronic complications arising from diabetes mellitus. These methods comprise administering to a mammal, preferably a human, in need of such treatment an effective amount of a compound of Formula I. Typical complications include diabetic cataracts, retinopathy, nephropathy and neuropathy.

In a further aspect, the invention provides pharmaceutical compositions comprising compounds of Formula I. Pharmaceutical compositions according to the invention contain one or more compounds of Formula I together with a pharmaceutically acceptable adjuvant or carrier.

In still another aspect, the compounds of the invention can be used as standards in assays for determining the affinity and selectivity of compounds for aldose reductase.

The compounds of Formula I also possess antihyperglycemic activity and are therefore useful for the treatment of hyperglycemia. Accordingly, an aspect of the invention is prevention and/or alleviation of complications associated with hyperglycemia with the pharmaceutical compositions of the invention.

The compounds of Formula I lower serum triglyceride levels. While serum triglyceride levels are often elevated in diabetic patients, they are also frequently elevated in non-diabetic patients resulting in various diseases and disorders, e.g., cardiac disease. Because of their ability to reduce serum triglyceride levels, the compositions of the present invention are useful in the treatment, i.e., prevention and/or alleviation, of elevated triglyceride levels in both diabetic and nondiabetic patients.

Thus, the compounds and compositions of the present invention may be used as antihyperlipidemic and/or antihyperglycemic agents. The compounds of Formula I may be given in combination with other glucose or lipid lowering agents as well as other agents that are given specifically to treat the complications of diabetes.

The compounds of Formula I exhibit anti-angiogenic activity. Thus, the compounds and compositions of the invention can be used to treat various diseases that exhibit aberrant vasoproliferation. According to the invention, the compound or composition would be administered to a mammal in need of inhibition of vasoproliferation, i.e., inhibition of angiogenesis. Examples of such diseases are diabetic retinopathy, age-related macular degeneration, retinopathy of prematurity, corneal neovascularization, pterygium, and any neoplasms (cancers) which appear to be angiogenesis dependent. Administration of the compound(s) of this invention is/are not limited to a particular mode, and could be administered systemically or topically to the eye in an appropriate ophthalmic solution. The compounds of Formula I may be administered in combination therapy with other known anti-angiogenic agents.

The compounds of Formula I have also been discovered to promote the healing of wounds in mammals. In preferred aspects, these compounds are useful in promoting wound healing in diabetic mammals. Thus, these compounds may be employed in the treatment of wounds in mammals, preferably humans, more preferably in diabetic humans.

In a preferred aspect, the invention provides pharmaceutical compositions containing compounds of Formula I.

In still another aspect, the invention provides for the use of a compound or compounds of Formula I for the preparation of a pharmaceutical composition for the treatment of any of the disorders or diseases (a) listed above, (b) connected with diabetic complications, hyperglycemia, or hypertriglyceridemia, or (c) where inhibition of vasoproliferation is indicated.

Prolonged administration of an ACE inhibitor at a therapeutically effective dose may be deleterious or give rise to side effects in certain patients, for example, it may lead to significant deterioration of renal function, induce hyperkalemia, neutropenia, angioneurotic oedema, rash or diarrhea or give rise to a dry cough. Administration of an ARI such as those of Formula I may also give rise to deleterious effects or side effects at the dose required to inhibit the enzyme aldose reductase sufficiently to produce a significant beneficial therapeutic effect. The present invention decreases the likelihood of problems associated with administration of indole acetic acids of Formula I or an ACE inhibitor that otherwise may result from administration of one of these agents alone. Furthermore, diabetic complications involve a complex mechanism or number of mechanisms, which initiate a cascade of biochemical alternations that in turn lead to structural changes. These may result in a diverse patient population. The present invention, therefore, provides the additional advantage that it allows tailoring of treatment to the needs of a particular patient population.

Accordingly, the present invention provides a pharmaceutical composition which comprises a compound of Formula I and an ACE inhibitor, together with a pharmaceutically acceptable carrier and/or diluent. In addition, the invention contemplates methods of treating diseases or disorders associated with elevated plasma levels of glucose, including complications associated with diabetes and hypertension and/or, congestive heart failure. These methods comprise administering an effective amount of a compound of Formula I in combination with an ACE inhibitor to a patient in need of such treatment, e.g., a patient suffering from diabetes or hypertension or a patient likely to contract either of those diseases.

In another aspect, this invention provides methods for lowering blood uric acid levels in mammals, e.g., humans.

The compounds of the invention can be used to treat any of the various diseases associated with elevated levels of uric acid, e.g., gout. Thus, in a broad aspect, the invention provides methods for reducing serum uric acid levels. In a related aspect, the invention provides a method of preventing or treating gout. The methods of the invention for lowing blood uric acid levels comprise administering to a mammal in need of blood uric acid lowering an effective amount of a compound of Formula I or a pharmaceutically acceptable salt thereof.

In another aspect, the invention further encompasses methods and intermediates useful for preparing the compounds of the invention.

DETAILED DESCRIPTION OF THE INVENTION

As shown above, the invention provides compounds of Formula I where D is selected from various substituted heteroaryl groups.

Preferred compounds of Formula I include those where R' is hydroxy, or $C_1$-$C_6$ alkoxy. More preferred R' groups are hydroxy, methoxy, and ethoxy. Particularly preferred are compounds where R' is hydroxy or ethoxy.

Other preferred compounds are those where Y is a phenyl group or a benzyl group, where each phenyl portion is optionally substituted with up to three substituents independently selected from halogen, $(C_1$-$C_6)$alkyl, $(C_1$-$C_6)$haloalkyl, nitro, $OR_7$, $SR_7$, $S(O)R_7$, $S(O)_2R_7$ or $N(R_7)_2$ wherein $R_7$ is hydrogen, $(C_1$-$C_6)$alkyl or $(C_1$-$C_6)$haloalkyl.

Still other preferred compounds are those where Y is naphthyl optionally substituted with one or two of halogen, cyano, nitro, trifluoromethyl, perfluoroethyl, trifluoroacetyl, or $(C_1$-$C_6)$alkanoyl, hydroxy, $(C_1$-$C_6)$alkyl, $(C_1$-$C_6)$alkoxy, $(C_1$-$C_6)$alkylthio, trifluoromethoxy, trifluoromethylthio, $(C_1$-$C_6)$alkylsulfinyl, $(C_1$-$C_6)$alkylsulfonyl.

Other preferred compounds of Formula I include those where Y is a heterocyclic 5-membered ring having one nitrogen, oxygen or sulfur, two nitrogens one of which may be replaced by oxygen or sulfur, or three nitrogens one of which may be replaced by oxygen or sulfur, said heterocyclic 5-membered ring substituted by one or two fluoro, chloro, $(C_1$-$C_6)$alkyl or phenyl, or condensed with benzo, or substituted by one of pyridyl, furyl or thienyl, said phenyl or benzo optionally substituted by one of iodo, cyano, nitro, perfluoroethyl, trifluoroacetyl, or $(C_1$-$C_6)$alkanoyl, one or two of fluoro, chloro, bromo, hydroxy, $(C_1$-$C_6)$alkyl, $(C_1$-$C_6)$alkoxy, $(C_1$-$C_6)$alkylthio, trifluoromethoxy, trifluoromethylthio, $(C_1$-$C_6)$alkylsulfinyl, $(C_1$-$C_6)$alkylsulfonyl or trifluoromethyl, or two fluoro or two trifluoromethyl with one hydroxy or one $(C_1$-$C_6)$alkoxy, or one or, preferably, two fluoro and one trifluoromethyl, or three fluoro, said pyridyl, furyl or thienyl optionally substituted in the 3-position by fluoro, chloro, bromo, $(C_1$-$C_6)$alkyl or $(C_1$-$C_6)$alkoxy;

a heterocyclic 6-membered ring having one to three nitrogen atoms, or one or two nitrogen atoms and one oxygen or sulfur, said heterocyclic 6-membered ring substituted by one or two $(C_1$-$C_6)$alkyl or phenyl, or condensed with benzo, or substituted by one of pyridyl, furyl or thienyl, said phenyl or benzo optionally substituted by one of iodo or trifluoromethylthio, or one or two of fluoro, chloro, bromo, $(C_1$-$C_6)$alkyl, $(C_1$-$C_6)$alkoxy, $(C_1$-$C_6)$alkylthio, $(C_1$-$C_6)$alkylsulfinyl, $(C_1$-$C_6)$alkylsulfonyl, or trifluoromethyl, and said pyridyl, furyl or thienyl optionally substituted in the 3-position by fluoro, chloro, $(C_1$-$C_6)$alkyl or $(C_1$-$C_6)$alkoxy;

said benzo-condensed heterocyclic 5-membered or 6-membered rings optionally substituted in the heterocyclic 5-membered or 6-membered ring by one of fluoro, chloro, bromo, methoxy, or trifluoromethyl;

oxazole or thiazole condensed with a 6-membered aromatic group containing one or two nitrogen atoms, with thiophene or with furane, each optionally substituted by one of fluoro, chloro, bromo, trifluoromethyl, methylthio or methylsulfinyl;

imidazolopyridine or triazolopyridine optionally substituted by one of trifluoromethyl, trifluoromethylthio, bromo, or $(C_1$-$C_6)$alkoxy, or two of fluoro or chloro;

thienothiophene or thienofuran optionally substituted by one of fluoro, chloro or trifluoromethyl;

thienotriazole optionally substituted by one of chloro or trifluoromethyl;

naphthothiazole; naphthoxazole; or thienoisothiazole;

Yet other preferred compounds of Formula I are those where Y is a benzothiazolyl, or more preferably, a benzothiazol-2-yl group that is optionally substituted with one, two or three groups.

Preferred compounds of the invention include those where A is $C_1$-$C_3$ optionally substituted as described above, and more preferably, methyl.

Other preferred compounds are those where Z is $(C_1$-$C_6)$ alkylene. Within this aspect, more preferred compounds are those where Ar is a substituted phenyl of Formula II or a substituted benzothiazole of Formula III

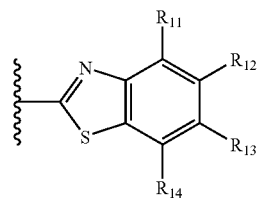

wherein $R_8$, $R_8'$, $R_9$, $R_9'$, $R_{10}$, $R_{11}$, $R_{12}$, $R_{13}$ and $R_{14}$ are independently hydrogen, halogen, $(C_1$-$C_6)$alkyl, halogen, $(C_1$-$C_6)$haloalkyl, $(C_2$-$C_6)$haloacetyl, cyano, nitro, $(C_1$-$C_6)$alkanoyl, $(C_1$-$C_6)$alkylthio, $(C_1$-$C_6)$haloalkylthio, $OR_7$, $SR_7$, $S(O)R_7$, $S(O)_2R_7$ or $N(R_7)_2$ wherein each $R_7$ is independently hydrogen, $C_1$-$C_6$ alkyl, $C_1$-$C_6$ haloalkyl, or $C_1$-$C_6$ haloalkoxy.

More preferably, $R_8$, $R_8'$, $R_9$, $R_9'$, $R_{10}$, $R_{11}$, $R_{12}$, $R_{13}$ and $R_{14}$ are independently hydrogen, hydroxy, $(C_1$-$C_6)$alkoxy, halogen, $(C_1$-$C_6)$alkyl, halogen, $(C_1$-$C_6)$haloalkyl, cyano, nitro, or $N(R_7)_2$ wherein each $R_7$ is independently hydrogen or $C_1$-$C_6$ alkyl.

Other preferred compounds are those where Z is $C_1$-$C_6$ alkylene.

Particularly preferred compounds having Ar groups of Formula II or III include those where $R_8$, $R_8'$, $R_9$, $R_9'$, $R_{10}$, $R_{11}$, $R_{12}$, $R_{13}$ and $R_{14}$ are independently hydrogen, fluorine, chlorine, bromine, trifluoromethyl or nitro.

Another preferred group of compounds is those where Z is $(C_1$-$C_3)$alkylene. This group of compounds, is referred to as compounds of Formula III.A. Within this group, more preferred compounds include those where Ar is

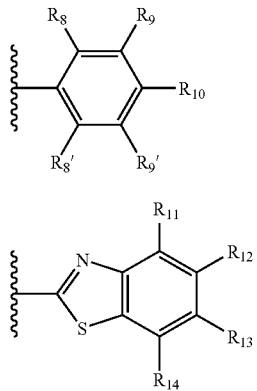

and $R_{11}$, $R_{12}$, $R_{13}$ and $R_{14}$ are independently hydrogen, hydroxy, $(C_1$-$C_6)$alkoxy, halogen, $(C_1$-$C_6)$alkyl, halogen, $(C_1$-$C_6)$haloalkyl, cyano, nitro, or $N(R_7)_2$ wherein each $R_7$ is independently hydrogen or $C_1$-$C_6$ alkyl.

This group of compounds is referred to as compounds of Formula III.A.1.

Preferred compounds of formula III-A.1 include those where D is selected from:

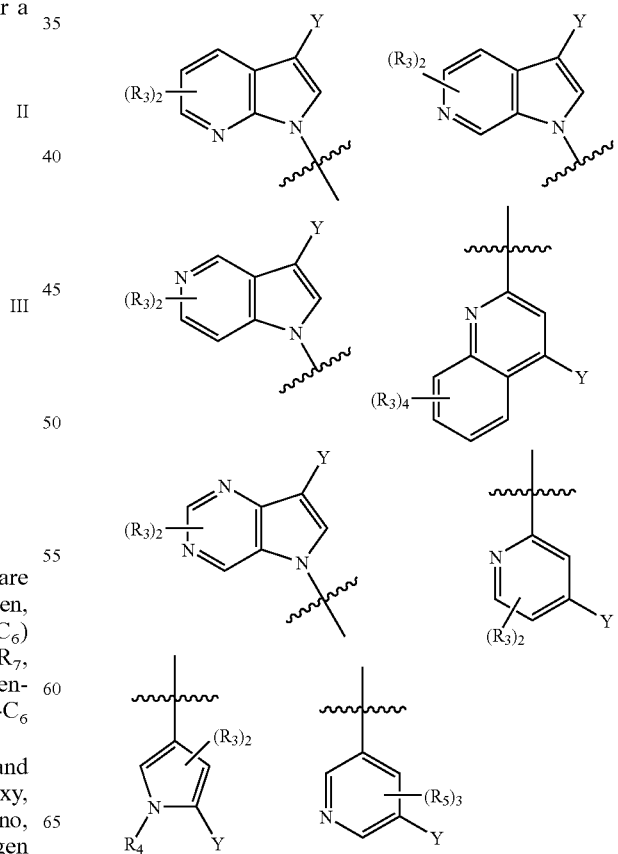

-continued

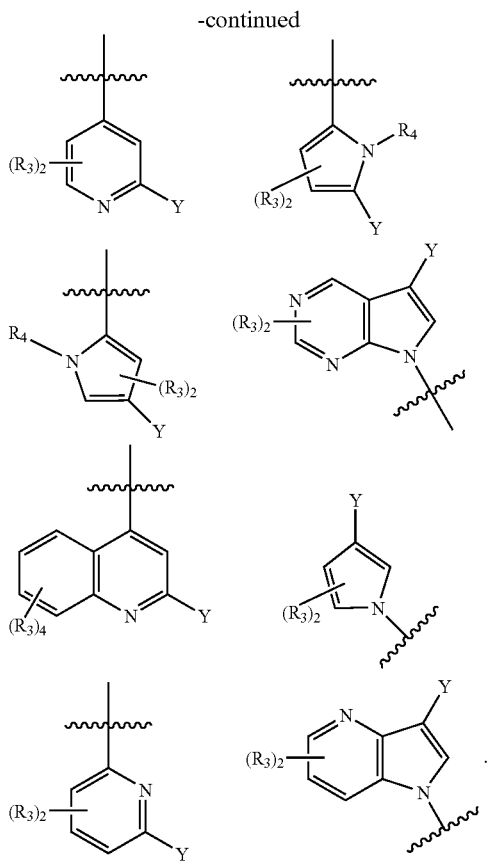

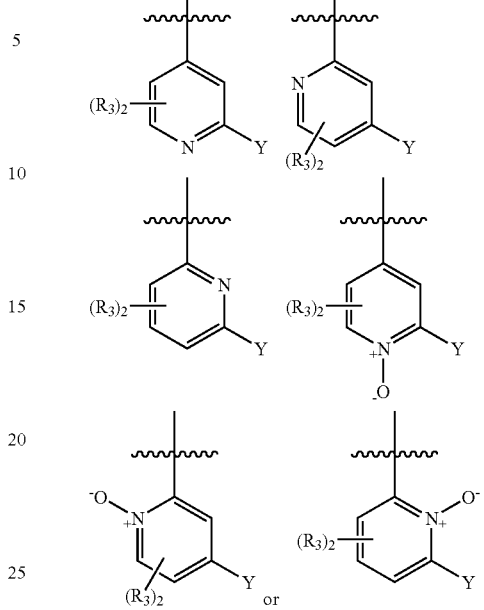

Other preferred compounds of III.A.1 include those where A and Z are both methylene.

Preferred compounds of the invention include those where R' is hydroxy or $C_1$-$C_6$ alkoxy. Particularly preferred compounds of III.A.1 include those where R' is hydroxy or $C_1$-$C_3$ alkoxy.

Within III.A.1, a specific preferred group of compounds, hereinafter compounds of Formula III.A.2, are those where D is

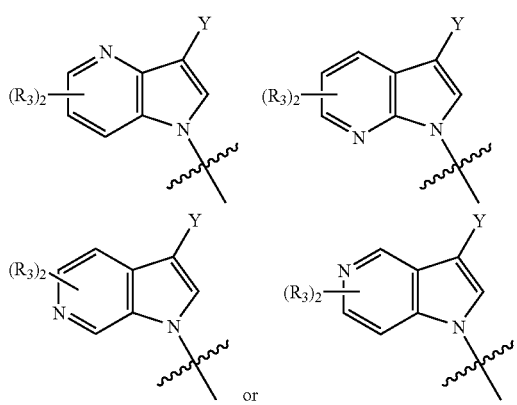

where each $R_3$ is hydrogen, or $C_1$-$C_6$ alkyl.

Also within III.A.1, another specific preferred group of compounds, hereinafter compounds of Formula III.A.3, are those where D is where each $R_3$ is independently hydrogen, $C_1$-$C_6$ alkyl, or phenyl($C_1$-$C_6$)alkyl where the phenyl portion is optionally substituted with one, two or three groups independently selected from halogen, hydroxy, $C_1$-$C_6$ alkyl, amino, ($C_1$-$C_6$)alkylamino, and di($C_1$-$C_6$)alkylamino. Particularly preferred D groups within III.A.3 are the following:

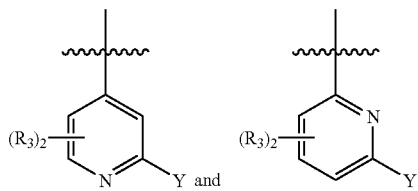

A further specific group of compounds within III.A.1, hereinafter compounds of Formula III.A.4, are those where D is

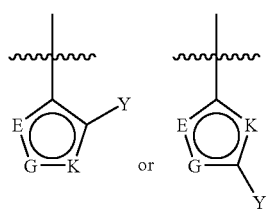

where
E, G, and K represent sulfur or C—$R_3$, provided that one and only one of E, G, and K is sulfur; and
$R_3$ represents hydrogen, $C_1$-$C_6$ alkyl, or phenyl($C_1$-$C_6$)alkyl.

Yet another specific group of compounds within III.A.1, hereinafter compounds of Formula III.A.5, are those where D is

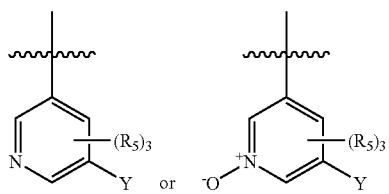 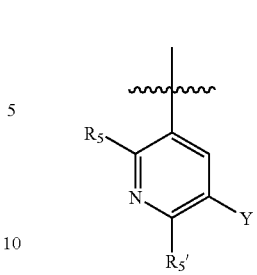

where each $R_5$ is independently hydrogen, $C_1$-$C_6$ alkyl, $C_1$-$C_6$ alkoxy, amino, mono- or di($C_1$-$C_6$)alkylamino, or phenyl($C_1$-$C_6$)alkyl, phenoxy or phenyl where each phenyl portion is optionally mono, di, or trisubstituted with independently selected hydroxy, halogen, $C_1$-$C_6$ alkyl, $C_1$-$C_6$ alkoxy, amino, or mono- or di($C_1$-$C_6$)alkylamino groups. More preferably, D in compounds of III.A.5 is

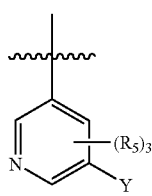

Within Formula III.A.5, a preferred group of compounds includes those where each $R_5$ is independently $C_1$-$C_3$ alkyl or one $R_5$ is phenyl or phenyl alkyl and the other two $R_5$ groups are independently hydrogen or $C_1$-$C_3$ alkyl. Particularly preferred compounds of III.A.5 are those where each $R_5$ is $C_1$-$C_2$ alkyl, preferably methyl.

Another preferred group of specific compounds within III.A.1, hereinafter compounds of Formula III.A.6, includes those where D is

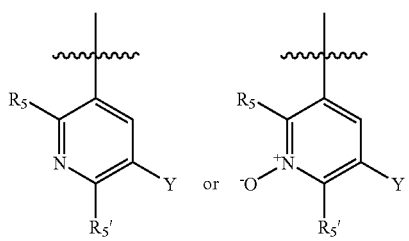

where $R_5$ and $R_5'$ independently represent hydrogen, $C_1$-$C_6$ alkyl, $C_1$-$C_6$ alkoxy, or phenyl($C_1$-$C_6$)alkyl, phenoxy or phenyl where each phenyl portion is optionally substituted with one or two independently selected hydroxy, halogen, $C_1$-$C_6$ alkyl, or $C_1$-$C_6$ alkoxy groups. More preferably, D in compounds of III.A.6 is Particularly preferred groups of compounds of Formula III.A.6 are those where (a) both of $R_5$ and $R_5'$ are independently $C_1$-$C_2$ alkyl, more preferably methyl;

(b) one of $R_5$ and $R_5'$ is hydrogen and the other is $C_1$-$C_2$ alkyl, more preferably methyl;

(c) both of $R_5$ and $R_5'$ are hydrogen;

(d) $R_5$ is phenyl or benzyl and $R_5'$ is hydrogen;

(e) $R_5'$ is phenyl or benzyl and $R_5$ is hydrogen.

A preferred specific group of compounds within III.A.1, hereinafter compounds of Formula III.A.7, are those where D is

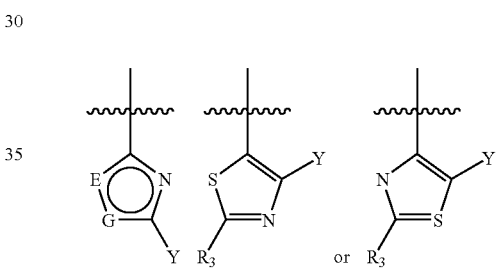

E and G represent sulfur or C—$R_3$, provided that one and only one of E and G is sulfur; and each $R_3$ independently represents hydrogen, $C_1$-$C_6$ alkyl, or phenyl ($C_1$-$C_6$)alkyl.

More preferred compounds of III.A.7 are those where D is

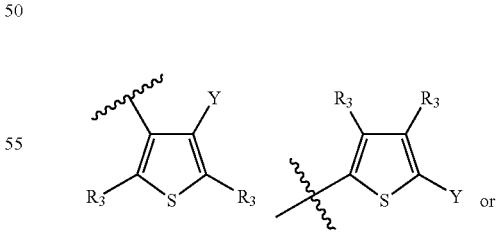

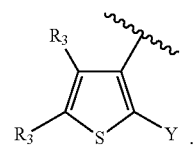

Another more preferred group of compounds within III.A.7 are includes compounds where D is

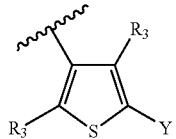

and each $R_3$ is independently hydrogen, $(C_1-C_6)$alkyl or phenyl $(C_1-C_6)$alkyl.

Particularly preferred compounds within III.A.7 include those where D is

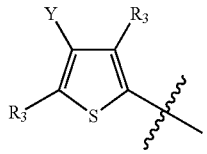

and each $R_3$ is independently hydrogen or $(C_1-C_6)$alkyl.

Preferred compounds of the invention, and particularly those of Formulas III.A.1-.7 are those where $R_{11}$, $R_{12}$, $R_{13}$ and $R_{14}$ are independently hydrogen, hydroxy, $(C_1-C_2)$alkoxy, trifluoromethyl, $(C_1-C_3)$alkyl, fluoro, chloro, bromo, nitro, amino, mono $(C_1-C_2)$alkylamino or di$(C_1-C_2)$alkylamino.

More preferred compounds of the invention, and particularly those of Formulas III.A.1-.7 are those where $R_{11}$, $R_{12}$, $R_{13}$ and $R_{14}$ are independently hydrogen, hydroxy, fluoro, chloro, nitro, or amino.

Particularly preferred compounds of the invention, and specifically those of Formulas III.A.1-.7 are those where three of $R_{11}$, $R_{12}$, $R_{13}$ and $R_{14}$ are fluoro and the other is hydrogen.

Other preferred compounds of the invention, and particularly those of Formulas III.A.1-.7 are those where at least one of $R_{11}$, $R_{12}$, $R_{13}$, and $R_{14}$ is trifluoromethyl.

A preferred group of compounds of the invention, and particularly those of Formulas III.A.1-.7, are those where $R_{12}$ is trifluoromethyl.

Preferred compounds of the invention, and specifically those of Formulas III.A.1-.7 are those where $R_{11}$, $R_{12}$, and $R_{14}$ represent fluorine and $R_{13}$ is hydrogen.

Preferred compounds of the invention include those $R_{11}$, $R_{12}$, and $R_{14}$ represent fluorine and $R_{13}$ is hydrogen.

Other preferred compounds of the invention are those where R' is hydrogen.

More preferred compounds of the invention are those where R' is $C_1-C_6$ alkoxy.

Another preferred group of compounds is those where Z is C(O)NH. This group of compounds is referred to as compounds of Formula III.B. Within this group, more preferred compounds include those where Ar is

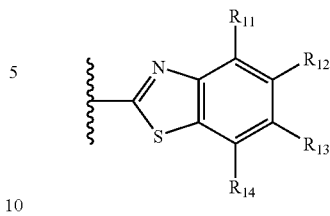

and $R_{11}$, $R_{12}$, $R_{13}$ and $R_{14}$ are independently hydrogen, hydroxy, $(C_1-C_6)$alkoxy, halogen, $(C_1-C_6)$alkyl, halogen, $(C_1-C_6)$haloalkyl, cyano, nitro, or $N(R_7)_2$ wherein each $R_7$ is independently hydrogen or $C_1-C_6$ alkyl.

This group of compounds is referred to as compounds of Formula III.B.1.

Specific compounds of formula III.B.1 include those where D is selected from:

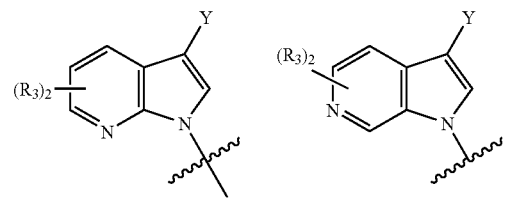

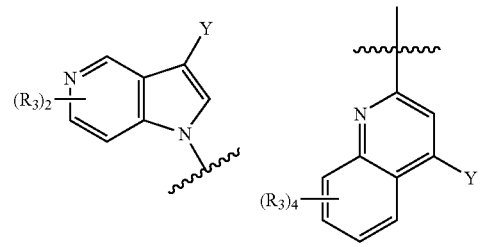

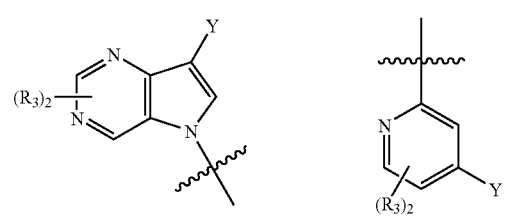

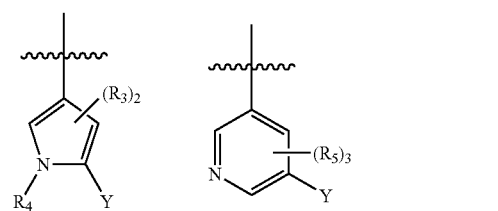

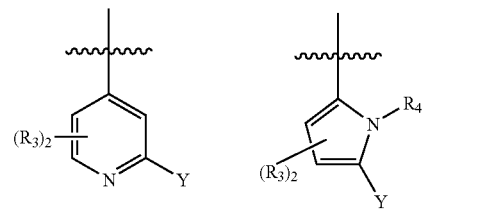

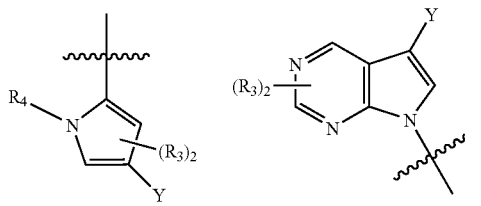

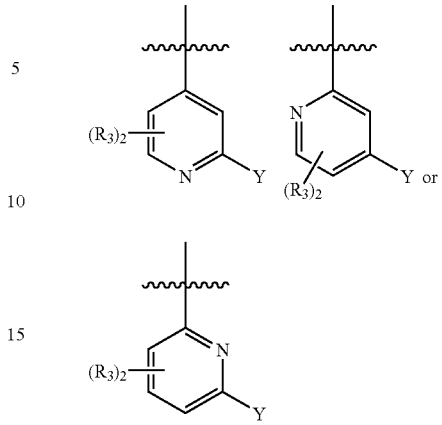

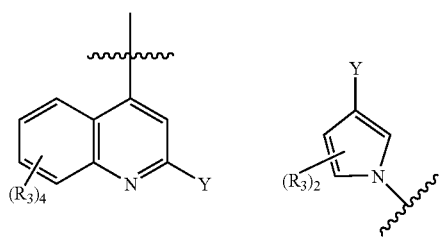

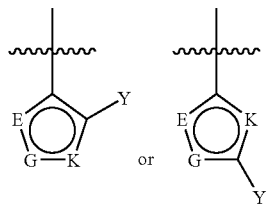

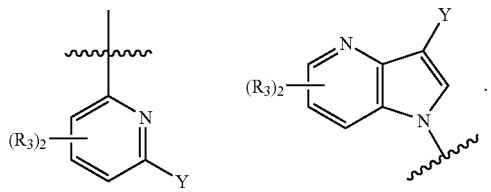

where each $R_3$ is independently hydrogen, $C_1$-$C_6$ alkyl, or phenyl($C_1$-$C_6$)alkyl where the phenyl portion is optionally substituted with one, two or three groups independently selected from halogen, hydroxy, $C_1$-$C_6$ alkyl, amino, ($C_1$-$C_6$)alkylamino, and di($C_1$-$C_6$)alkylamino.

A further specific group of compounds within III.B.1, hereinafter compounds of Formula III.B.4, are those where D is

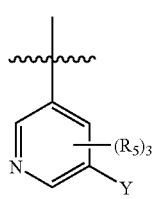

where
E, G, and K represent sulfur or C-$R_3$, provided that one and only one of E, G, and K is sulfur; and
$R_3$ represents hydrogen, $C_1$-$C_6$ alkyl, or phenyl($C_1$-$C_6$)alkyl.

Yet another specific group of compounds within III.B.1, hereinafter compounds of Formula III.B.5, are those where D is Other specific compounds of III.B.1 include those where A and Z are both methylene.

Preferred compounds of the invention include those where R' is hydroxy or $C_1$-$C_6$ alkoxy. Particularly preferred compounds of III.B.1 include those where R' is hydroxy or $C_1$-$C_3$ alkoxy.

Within III.B.1, a specific preferred group of compounds, hereinafter compounds of Formula III.B.2, are those where D is

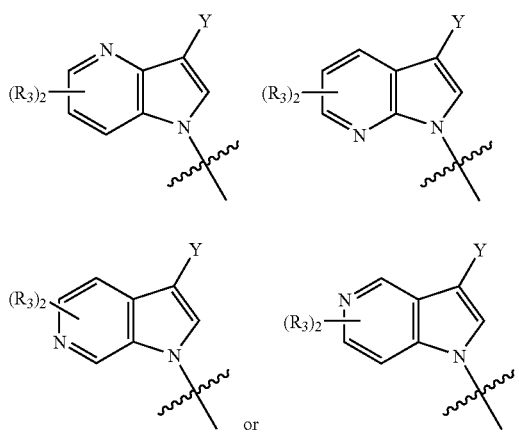

where each $R_3$ is hydrogen, or $C_1$-$C_6$ alkyl.

Also within III.B.1, another specific preferred group of compounds, hereinafter compounds of Formula III.B.3, are those where D is where each $R_5$ is independently hydrogen, $C_1$-$C_6$ alkyl, $C_1$-$C_6$ alkoxy, amino, mono- or di($C_1$-$C_6$)alkylamino, or phenyl($C_1$-$C_6$)alkyl, phenoxy or phenyl where each phenyl portion is optionally mono, di, or trisubstituted with independently selected hydroxy, halogen, $C_1$-$C_6$ alkyl, $C_1$-$C_6$ alkoxy, amino, or mono- or di($C_1$-$C_6$)alkylamino groups.

A preferred group of specific compounds within III.B.1, hereinafter compounds of Formula III.B.6, includes those where D is

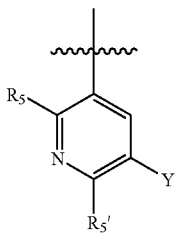

where $R_5$ and $R_5'$ independently represent hydrogen, $C_1$-$C_6$ alkyl, $C_1$-$C_6$ alkoxy, or phenyl($C_1$-$C_6$)alkyl, phenoxy or phenyl where each phenyl portion is optionally substituted with one or two independently selected hydroxy, halogen, $C_1$-$C_6$ alkyl, or $C_1$-$C_6$ alkoxy groups.

A preferred specific group of compounds within III.B.1, hereinafter compounds of Formula III.B.7, are those where D is

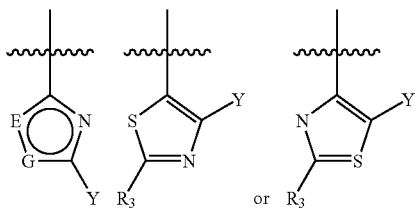

E and G represent sulfur or C—$R_3$, provided that one and only one of E and G is sulfur; and each $R_3$ independently represents hydrogen, $C_1$-$C_6$ alkyl, or phenyl($C_1$-$C_6$)alkyl.

More preferred compounds of III.B.7 are those where D is

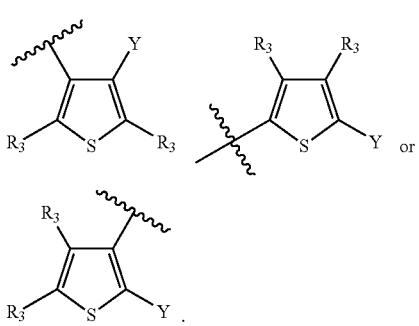

Another more preferred group of compounds within III.B.7 are includes compounds where D is

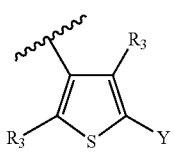

and each $R_3$ is independently hydrogen, ($C_1$-$C_6$)alkyl or phenyl($C_1$-$C_6$)alkyl.

Particularly preferred compounds within III.B.7 include those where D is

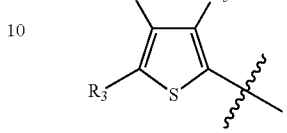

and each $R_3$ is independently hydrogen or ($C_1$-$C_6$)alkyl.

Preferred compounds of the invention, and particularly those of Formulas III.B.1-.7 are those where $R_{11}$, $R_{12}$, $R_{13}$ and $R_{14}$ are independently hydrogen, hydroxy, ($C_1$-$C_2$) alkoxy, trifluoromethyl, ($C_1$-$C_3$)alkyl, fluoro, chloro, bromo, nitro, amino, mono($C_1$-$C_2$)alkylamino or di($C_1$-$C_2$)alkylamino.

More preferred compounds of the invention, and particularly those of Formulas III.B.1-.7 are those where $R_{11}$, $R_{12}$, $R_{13}$ and $R_{14}$ are independently hydrogen, hydroxy, fluoro, chloro, nitro, or amino.

Particularly preferred compounds of the invention, and specifically those of Formulas III.B.1-.7 are those where three of $R_{11}$, $R_{12}$, $R_{13}$ and $R_{14}$ are fluoro and the other is hydrogen.

Other preferred compounds of the invention, and particularly those of Formulas III.B.1-.7 are those where at least one of $R_{11}$, $R_{12}$, $R_{13}$, and $R_{14}$ is trifluoromethyl.

A preferred group of compounds of the invention, and particularly those of Formulas III.B.1-.7, are those where $R_{12}$ is trifluoromethyl.

Preferred compounds of the invention, and specifically those of Formulas III.B.1-.7 are those where $R_{11}$, $R_{12}$, and $R_{14}$ represent fluorine and $R_{13}$ is hydrogen.

Another preferred group of compounds is those where Z is a bond. This group of compounds is referred to as compounds of Formula III.C. Within this group, more preferred compounds include those where Ar is

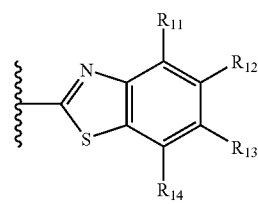

and $R_{11}$, $R_{12}$, $R_{13}$ and $R_{14}$ are independently hydrogen, hydroxy, ($C_1$-$C_6$)alkoxy, halogen, ($C_1$-$C_6$)alkyl, halogen, ($C_1$-$C_6$)haloalkyl, cyano, nitro, or N($R_7$)$_2$ wherein each $R_7$ is independently hydrogen or $C_1$-$C_6$ alkyl.

This group of compounds is referred to as compounds of Formula III.C.1.

Specific compounds of formula III.C.1 include those where D is selected from:

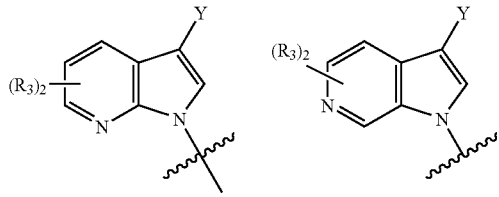
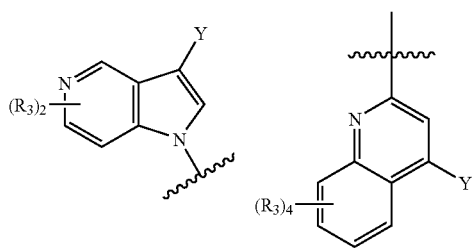
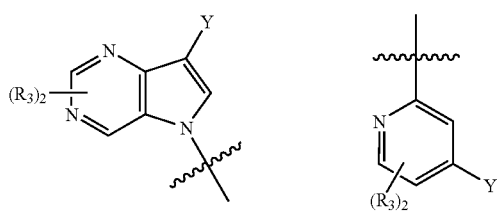
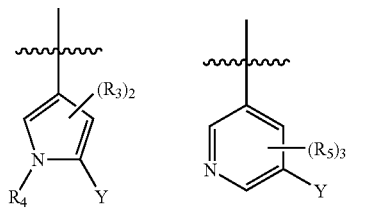
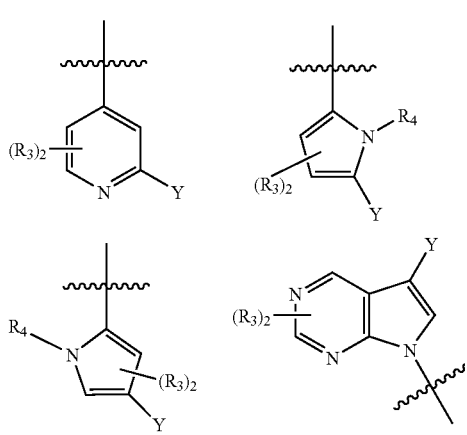
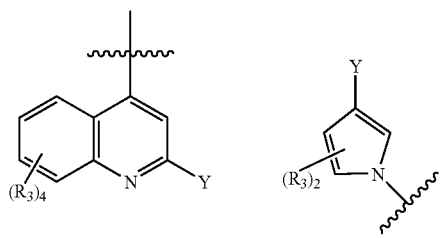

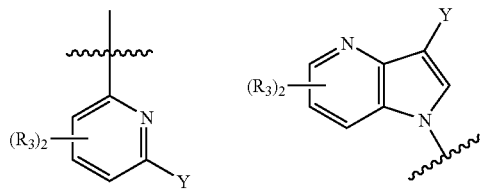

Other specific compounds of III.C.1 include those where A and Z are both methylene.

Preferred compounds of the invention include those where R' is hydroxy or $C_1$-$C_6$ alkoxy. Particularly preferred compounds of III.C.1 include those where R' is hydroxy or $C_1$-$C_3$ alkoxy.

Within III.C.1, a specific preferred group of compounds, hereinafter compounds of Formula III.C.2, are those where D is

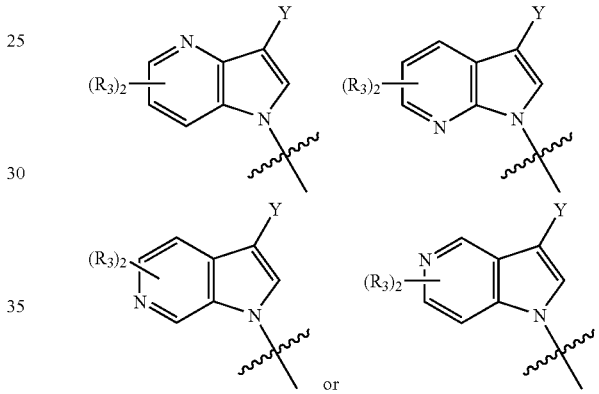

where each $R_3$ is hydrogen, or $C_1$-$C_6$ alkyl.

Also within III.C.1, another specific preferred group of compounds, hereinafter compounds of Formula III.C.3, are those where D is

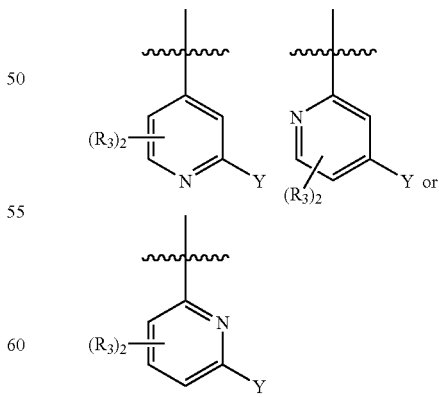

where each $R_3$ is independently hydrogen, $C_1$-$C_6$ alkyl, or phenyl($C_1$-$C_6$)alkyl where the phenyl portion is optionally substituted with one, two or three groups independently selected from halogen, hydroxy, $C_1$-$C_6$ alkyl, amino, ($C_1$-$C_6$)alkylamino, and di($C_1$-$C_6$)alkylamino.

A further specific group of compounds within III.C.1, hereinafter compounds of Formula III.C.4, are those where D is

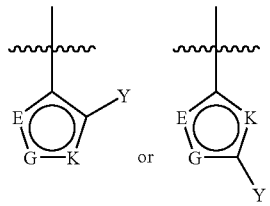

where

E, G, and K represent sulfur or C—$R_3$, provided that one and only one of E, G, and K is sulfur; and $R_3$ represents hydrogen, $C_1$-$C_6$ alkyl, or phenyl($C_1$-$C_6$)alkyl.

Yet another specific group of compounds within III.C.1, hereinafter compounds of Formula III.C.5, are those where D is

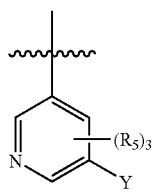

where each $R_5$ is independently hydrogen, $C_1$-$C_6$ alkyl, $C_1$-$C_6$ alkoxy, amino, mono- or di($C_1$-$C_6$)alkylamino, or phenyl($C_1$-$C_6$)alkyl, phenoxy or phenyl where each phenyl portion is optionally mono, di, or trisubstituted with independently selected hydroxy, halogen, $C_1$-$C_6$ alkyl, $C_1$-$C_6$ alkoxy, amino, or mono- or di($C_1$-$C_6$)alkylamino groups.

A preferred group of specific compounds within III.C.1, hereinafter compounds of Formula III.C.6, includes those where D is

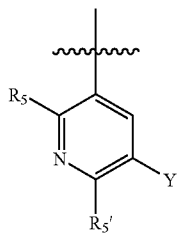

where $R_5$ and $R_5'$ independently represent hydrogen, $C_1$-$C_6$ alkyl, $C_1$-$C_6$ alkoxy, or phenyl($C_1$-$C_6$)alkyl, phenoxy or phenyl where each phenyl portion is optionally substituted with one or two independently selected hydroxy, halogen, $C_1$-$C_6$ alkyl, or $C_1$-$C_6$ alkoxy groups.

A preferred specific group of compounds within III.C.1 hereinafter compounds of Formula III.C.7, are those where D is

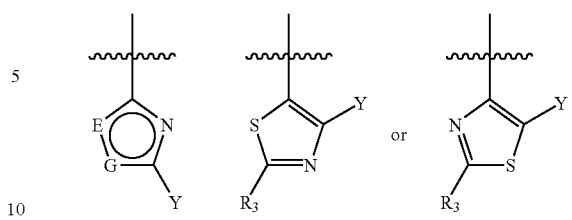

E and G represent sulfur or C—$R_3$, provided that one and only one of E and G is sulfur; and each $R_3$ independently represents hydrogen, $C_1$-$C_6$ alkyl, or phenyl($C_1$-$C_6$)alkyl.

More preferred compounds of III.C.7 are those where D is

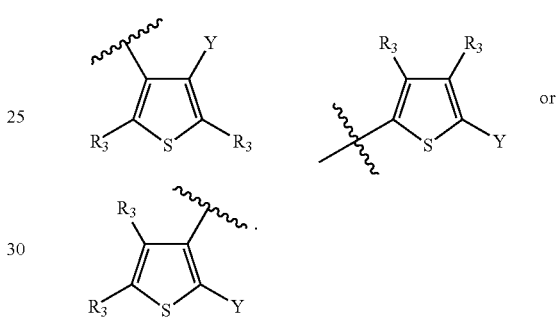

Another more preferred group of compounds within III.C.7 are includes compounds where D is

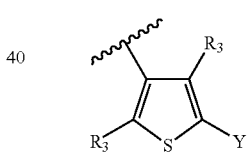

and each $R_3$ is independently hydrogen, ($C_1$-$C_6$)alkyl or phenyl($C_1$-$C_6$)alkyl.

Particularly preferred compounds within III.C.7 include those where D is

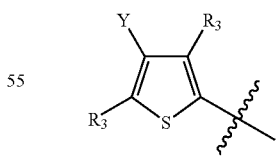

and each $R_3$ is independently hydrogen or ($C_1$-$C_6$)alkyl.

Preferred compounds of the invention, and particularly those of Formulas III.C.1-.7 are those where $R_{11}$, $R_{12}$, $R_{13}$ and $R_{14}$ are independently hydrogen, hydroxy, ($C_1$-$C_2$) alkoxy, trifluoromethyl, ($C_1$-$C_3$)alkyl, fluoro, chloro, bromo, nitro, amino, mono($C_1$-$C_2$)alkylamino or di($C_1$-$C_2$)alkylamino.

More preferred compounds of the invention, and particularly those of Formulas III.C.1-.7 are those where $R_{11}$, $R_{12}$, $R_{13}$ and $R_{14}$ are independently hydrogen, hydroxy, fluoro, chloro, nitro, or amino.

Particularly preferred compounds of the invention, and specifically those of Formulas III.C.1-.7 are those where three of $R_{11}$, $R_{12}$, $R_{13}$ and $R_{14}$ are fluoro and the other is hydrogen.

Other preferred compounds of the invention, and particularly those of Formulas III.C.1-.7 are those where at least one of $R_{11}$, $R_{12}$, $R_{13}$, and $R_{14}$ is trifluoromethyl.

A preferred group of compounds of the invention, and particularly those of Formulas III.C.1-.7, are those where $R_{12}$ is trifluoromethyl.

Preferred compounds of the invention, and specifically those of Formulas III.C.1-.7 are those where $R_{11}$, $R_{12}$, and $R_{14}$ represent fluorine and $R_{13}$ is hydrogen.

Another preferred group of compounds is those where Z is a oxygen. This group of compounds is referred to as compounds of Formula III.D. Within this group, more preferred compounds include those where Ar is

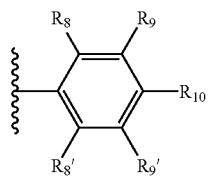

II and $R_8$, $R_8'$, $R_9$, $R_9'$ and $R_{10}$ are independently hydrogen, hydroxy, $(C_1\text{-}C_6)$alkoxy, halogen, $(C_1\text{-}C_6)$alkyl, halogen, $(C_1\text{-}C_6)$haloalkyl, cyano, nitro, or $N(R_7)_2$ wherein each $R_7$ is independently hydrogen or $C_1\text{-}C_6$ alkyl.

This group of compounds is referred to as compounds of Formula III.D.1.

Specific compounds of formula III.D.1 include those where D is selected from:

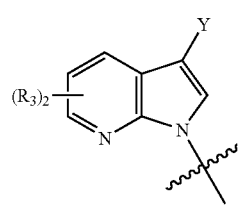

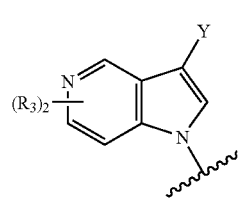

-continued

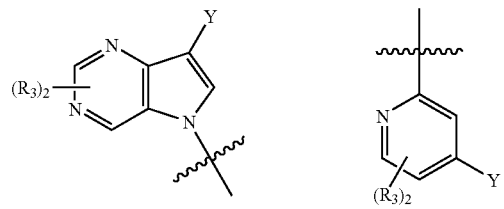

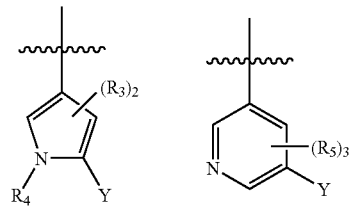

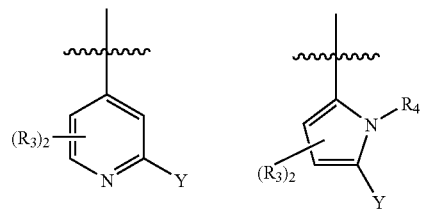

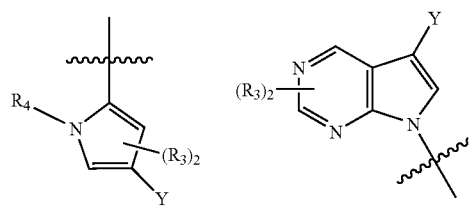

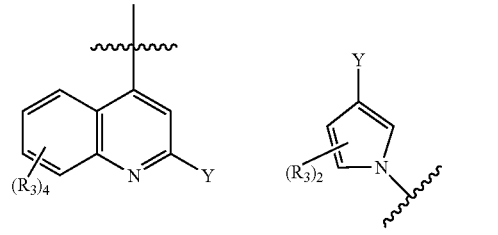

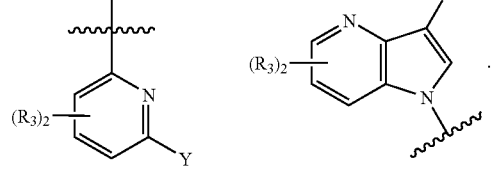

Other specific compounds of III.D.1 include those where A and Z are both methylene.

Preferred compounds of the invention include those where R' is hydroxy or $C_1\text{-}C_6$ alkoxy. Particularly preferred compounds of III.D.1 include those where R' is hydroxy or $C_1\text{-}C_3$ alkoxy.

Within III.D.1, a specific preferred group of compounds, hereinafter compounds of Formula III.D.2, are those where D is

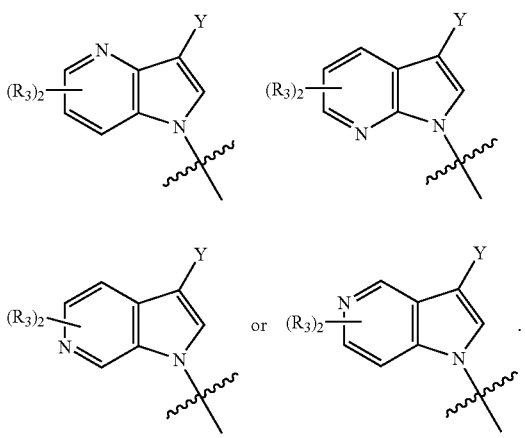

where each R₃ is hydrogen, or $C_1$-$C_6$ alkyl.

Also within III.D.1, another specific preferred group of compounds, hereinafter compounds of Formula III.D.3, are those where D is

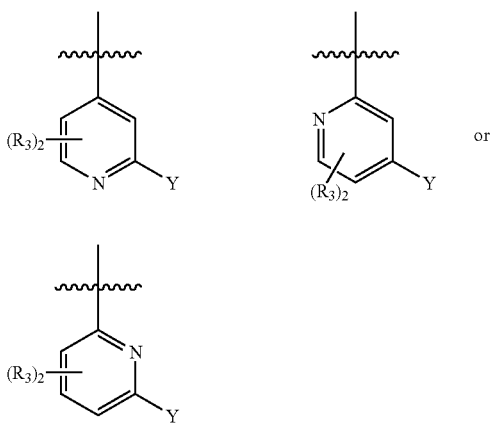

where each $R_3$ is independently hydrogen, $C_1$-$C_6$ alkyl, or phenyl($C_1$-$C_6$)alkyl where the phenyl portion is optionally substituted with one, two or three groups independently selected from halogen, hydroxy, $C_1$-$C_6$ alkyl, amino, ($C_1$-$C_6$)alkylamino, and di($C_1$-$C_6$)alkylamino.

A further specific group of compounds within III.D.1, hereinafter compounds of Formula III.D.4, are those where D is

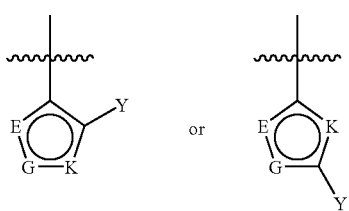

where

E, G, and K represent sulfur or C—$R_3$, provided that one and only one of E, G, and K is sulfur; and $R_3$ represents hydrogen, $C_1$-$C_6$ alkyl, or phenyl($C_1$-$C_6$)alkyl.

Yet another specific group of compounds within III.D.1, hereinafter compounds of Formula III.D.5, are those where D is

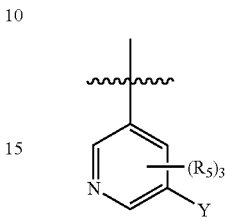

where each $R_5$ is independently hydrogen, $C_1$-$C_6$ alkyl, $C_1$-$C_6$ alkoxy, amino, mono- or di($C_1$-$C_6$)alkylamino, or phenyl($C_1$-$C_6$)alkyl, phenoxy or phenyl where each phenyl portion is optionally mono, di, or trisubstituted with independently selected hydroxy, halogen, $C_1$-$C_6$ alkyl, $C_1$-$C_6$ alkoxy, amino, or mono- or di($C_1$-$C_6$)alkylamino groups.

A preferred group of specific compounds within III.D.1, hereinafter compounds of Formula III.D.6, includes those where D is

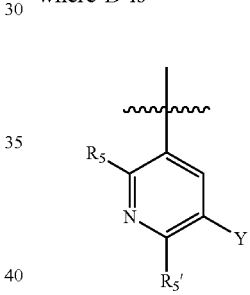

where $R_5$ and $R_5'$ independently represent hydrogen, $C_1$-$C_6$ alkyl, $C_1$-$C_6$ alkoxy, or phenyl($C_1$-$C_6$)alkyl, phenoxy or phenyl where each phenyl portion is optionally substituted with one or two independently selected hydroxy, halogen, $C_1$-$C_6$ alkyl, or $C_1$-$C_6$ alkoxy groups.

A preferred specific group of compounds within III.D.1, hereinafter compounds of Formula III.D.7, are those where D is

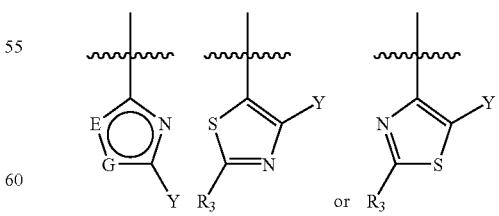

E and G represent sulfur or C—$R_3$, provided that one and only one of E and G is sulfur; and each $R_3$ independently represents hydrogen, $C_1$-$C_6$ alkyl, or phenyl($C_1$-$C_6$)alkyl.

More preferred compounds of III.D.7 are those where D is

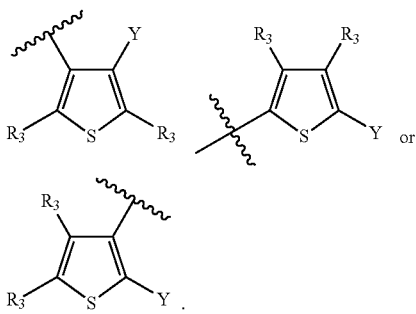

Another more preferred group of compounds within III.D.7 are includes compounds where D is

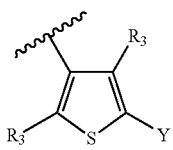

and each $R_3$ is independently hydrogen, $(C_1-C_6)$alkyl or phenyl$(C_1-C_6)$alkyl.

Particularly preferred compounds within III.D.7 include those where D is

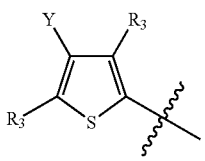

and each $R_3$ is independently hydrogen or $(C_1-C_6)$alkyl.

Preferred compounds of the invention, and particularly those of Formulas III.D.1-.7 are those where $R_8$, $R_8'$, $R_9$, $R_9'$ and $R_{10}$ are independently hydrogen, hydroxy, $(C_1-C_2)$ alkoxy, trifluoromethyl, $(C_1-C_3)$alkyl, fluoro, chloro, bromo, nitro, amino, mono$(C_1-C_2)$alkylamino or di$(C_1-C_2)$alkylamino.

More preferred compounds of the invention, and particularly those of Formulas III.D.1-.7 are those where $R_8$, $R_8'$, $R_9$, $R_9'$ and $R_{10}$ are independently hydrogen, hydroxy, fluoro, chloro, nitro, or amino.

Particularly preferred compounds of the invention, and specifically those of Formulas III.D.1-.7 are those where three of $R_8$, $R_8'$, $R_9$, $R_9'$ and $R_{10}$ are fluoro and the other is hydrogen.

Other particularly preferred compounds of the invention, and particularly those of Formulas III.D.1-.7 are those where at least one of $R_8$, $R_8'$, $R_9$, $R_9'$ and $R_{10}$ is trifluoromethyl.

A preferred group of compounds of the invention, and particularly those of Formulas III.D.1-.7 are those where $R_{10}$ is trifluoromethyl.

Preferred compounds of the invention, and specifically those of Formulas III.D.1-.7 are those where $R_8$, $R_9'$ and $R_{10}$ represent fluorine.

As noted above, the invention provides intermediates useful in preparing the compounds of the invention. Thus, the invention provides intermediate compounds of formulas A-1 to A-6, and A-8:

A-1

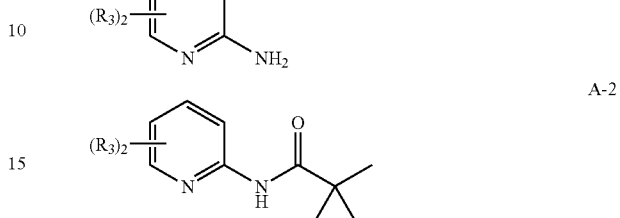
A-2

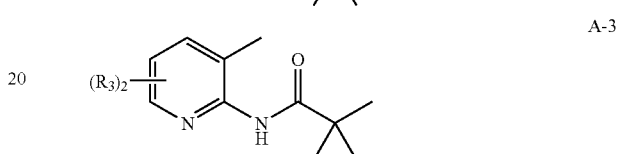
A-3

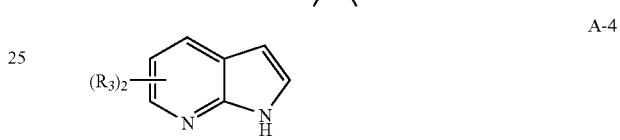
A-4

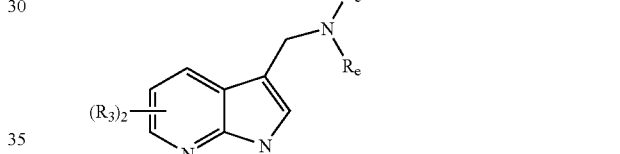
A-5

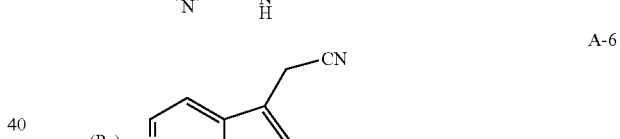
A-6

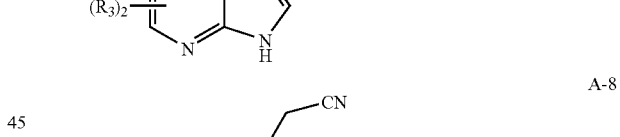
A-8

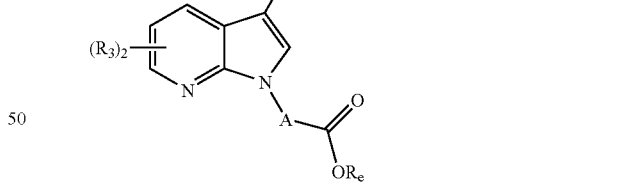

where each Re is independently $C_1-C_6$ alkyl

The invention also provides intermediate compounds of formulas B-3, B-4, and B-6.

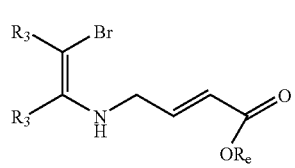
B-3 where Re is $C_1$-$C_6$ alkyl

The invention also provides intermediate compounds of formulas C-2, C-3, C-4, and C-6.

where Hal is chloro or bromo.

The invention also provides intermediate compounds of formulas D-5 and D-6.

where each $R_e$ is independently $C_1$-$C_6$ alkyl.

The invention also provides intermediate compounds of formulas E-1 and E-2.

where each $R_e$ is independently $C_1$-$C_6$ alkyl.

The invention also provides intermediate compounds of formulas F-2, F-3, F-4, F-5, F-6, and F-8.

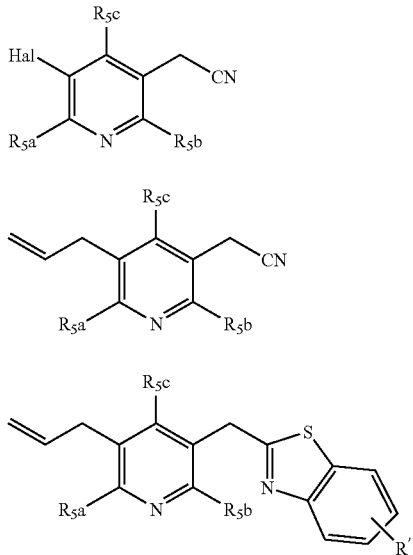

F-5

F-6

F-8 where is Hal is independently chloro or bromo.

The invention also provides intermediate compounds of formulas G-2, G-3, and G-4.

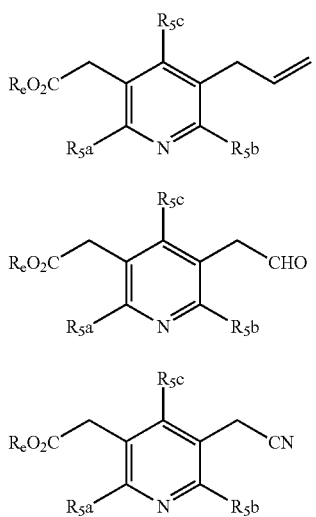

G-2

G-3

G-4 where each $R_e$ is $C_1$-$C_6$ alkyl

The invention also provides intermediate compounds of formulas H-2, H-3, and H-4.

H-2

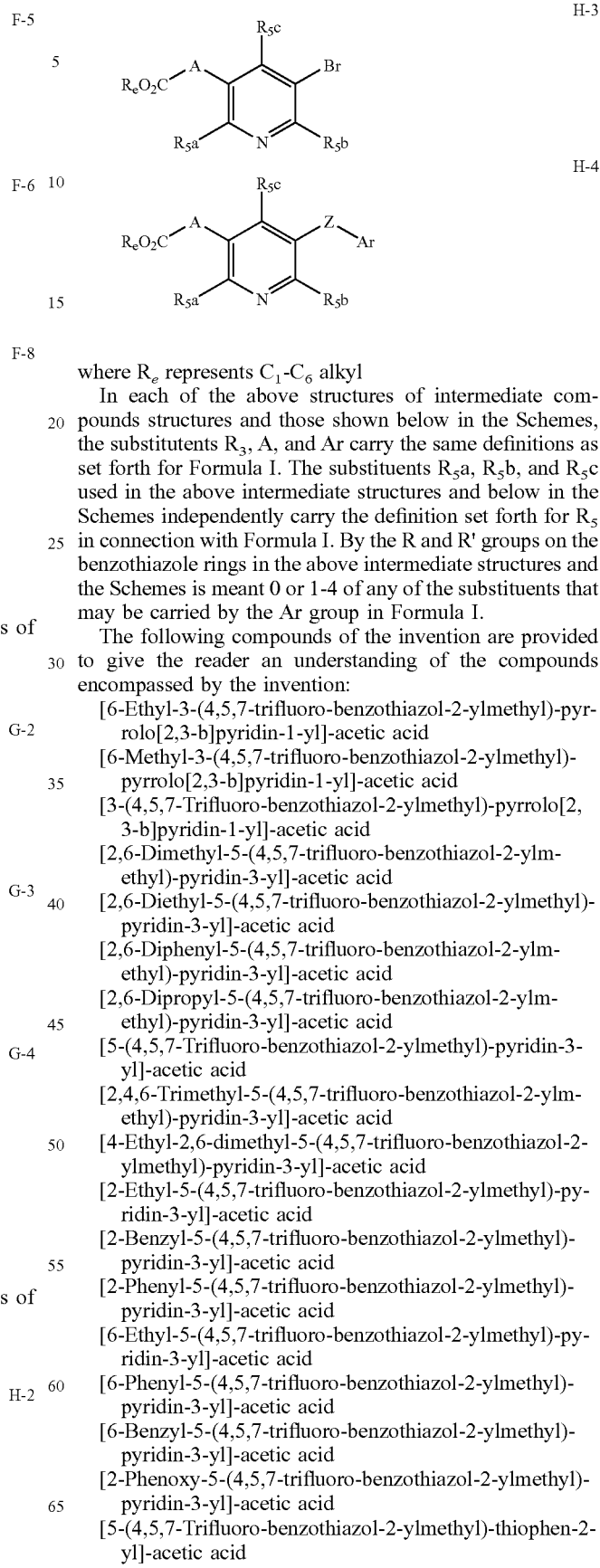

H-3

H-4 where $R_e$ represents $C_1$-$C_6$ alkyl

In each of the above structures of intermediate compounds structures and those shown below in the Schemes, the substitutents $R_3$, A, and Ar carry the same definitions as set forth for Formula I. The substituents $R_5a$, $R_5b$, and $R_5c$ used in the above intermediate structures and below in the Schemes independently carry the definition set forth for $R_5$ in connection with Formula I. By the R and R' groups on the benzothiazole rings in the above intermediate structures and the Schemes is meant 0 or 1-4 of any of the substituents that may be carried by the Ar group in Formula I.

The following compounds of the invention are provided to give the reader an understanding of the compounds encompassed by the invention:

[6-Ethyl-3-(4,5,7-trifluoro-benzothiazol-2-ylmethyl)-pyrrolo[2,3-b]pyridin-1-yl]-acetic acid
[6-Methyl-3-(4,5,7-trifluoro-benzothiazol-2-ylmethyl)-pyrrolo[2,3-b]pyridin-1-yl]-acetic acid
[3-(4,5,7-Trifluoro-benzothiazol-2-ylmethyl)-pyrrolo[2,3-b]pyridin-1-yl]-acetic acid
[2,6-Dimethyl-5-(4,5,7-trifluoro-benzothiazol-2-ylmethyl)-pyridin-3-yl]-acetic acid
[2,6-Diethyl-5-(4,5,7-trifluoro-benzothiazol-2-ylmethyl)-pyridin-3-yl]-acetic acid
[2,6-Diphenyl-5-(4,5,7-trifluoro-benzothiazol-2-ylmethyl)-pyridin-3-yl]-acetic acid
[2,6-Dipropyl-5-(4,5,7-trifluoro-benzothiazol-2-ylmethyl)-pyridin-3-yl]-acetic acid
[5-(4,5,7-Trifluoro-benzothiazol-2-ylmethyl)-pyridin-3-yl]-acetic acid
[2,4,6-Trimethyl-5-(4,5,7-trifluoro-benzothiazol-2-ylmethyl)-pyridin-3-yl]-acetic acid
[4-Ethyl-2,6-dimethyl-5-(4,5,7-trifluoro-benzothiazol-2-ylmethyl)-pyridin-3-yl]-acetic acid
[2-Ethyl-5-(4,5,7-trifluoro-benzothiazol-2-ylmethyl)-pyridin-3-yl]-acetic acid
[2-Benzyl-5-(4,5,7-trifluoro-benzothiazol-2-ylmethyl)-pyridin-3-yl]-acetic acid
[2-Phenyl-5-(4,5,7-trifluoro-benzothiazol-2-ylmethyl)-pyridin-3-yl]-acetic acid
[6-Ethyl-5-(4,5,7-trifluoro-benzothiazol-2-ylmethyl)-pyridin-3-yl]-acetic acid
[6-Phenyl-5-(4,5,7-trifluoro-benzothiazol-2-ylmethyl)-pyridin-3-yl]-acetic acid
[6-Benzyl-5-(4,5,7-trifluoro-benzothiazol-2-ylmethyl)-pyridin-3-yl]-acetic acid
[2-Phenoxy-5-(4,5,7-trifluoro-benzothiazol-2-ylmethyl)-pyridin-3-yl]-acetic acid
[5-(4,5,7-Trifluoro-benzothiazol-2-ylmethyl)-thiophen-2-yl]-acetic acid

[3-Methyl-4-(4,5,7-trifluoro-benzothiazol-2-ylmethyl)-thiophen-2-yl]-acetic acid
[4-(4,5,7-Trifluoro-benzothiazol-2-ylmethyl)-thiophen-2-yl]-acetic acid
[2-(4,5,7-Trifluoro-benzothiazol-2-ylmethyl)-thiophen-3-yl]-acetic acid
[4-Methyl-5-(4,5,7-trifluoro-benzothiazol-2-ylmethyl)-thiophen-3-yl]-acetic acid
[5-(4,5,7-Trifluoro-benzothiazol-2-ylmethyl)-thiophen-3-yl]-acetic acid
[2,5-Dimethyl-4-(4,5,7-trifluoro-benzothiazol-2-ylmethyl)-thiophen-3-yl]-acetic acid
[2-(4,5,7-Trifluoro-benzothiazol-2-ylmethyl)-thiazol-4-yl]-acetic acid The above compounds, further described in the Examples and other description of the invention below, are illustrative but are not meant to limit in any way the scope of the contemplated compounds according to the present invention.

The compounds of Formula I are administered to a patient or subject in need of treatment either alone or in combination with other compounds having similar or different biological activities. In addition, the pharamceutical compositions comprising an ACE inhibitor and a compound of Formula I may also be used in combination with other compounds. For example, the compounds and compositions of the invention may be administered in a combination therapy, i.e., either simultaneously in single or separate dosage forms or in separate dosage forms within hours or days of each other. Examples of such combination therapies include administering the compositions and compounds of Formula I with other agents used to treat hyperglycemia, hyperlipidemia, and diabetic complications.

Suitable compounds for use in combination therapy include

For Hyperglycemia:
  Insulin
  Metformin
  Troglitazone
  Pioglitazone
  Rosiglitazone
  Darglitazone
  Sulfonylureass such as glipizide and glimepiride
  Repaglinide
  alpha-glucosidase inhibitors such as acarbose, miglitol For Diabetic Complications:
  ACE inhibitors: Captopril, enalapril, lisinopril, omaprilat
  Angiotensin II receptor antagonists (AT1-receptor) such as candesartan, losartan, irbesartan, and valsartan
  MMP inhibitors
  Protein kinase C inhibitors For Antihyperlipidemia:
  Statins such as Atorvastatin, simvastatin, pravastatin, fluvastatin, lovastatin, cerivastatin
  Fibrates such as Fenofibrate, bezafibrate, ciprofibrate, gemfibrozil Unless otherwise indicated to the contrary, when a group such as phenyl or amino is said to be substituted with, e.g., two or three substituents, it is understood that the substituents are the same or different. By way of example, "di($C_1$-$C_6$)alkylamino" embraces N-ethyl-N-methylamino, N,N-diethylamino, N,N-dimethylamino, N-propyl-N-ethylamino, etc. As a further non-limiting example, "phenyl optionally substituted with up to three of halogen, hydroxy, ($C_1$-$C_6$) alkyl, ($C_1$-$C_6$)alkoxy, nitro, amino, ($C_1$-$C_6$)alkylamino, or di($C_1$-$C_6$)alkylamino" embraces phenyl, 2-fluoro-4-hydroxyphenyl, 2-amino-3-butyl-5-nitrophenyl, 3-bromo-4-propoxyphenyl, 2-ethylamino-4-fluoro-3-hydroxyphenyl, etc. Further, it is understood that all substituents are attached to the parent moiety at a substitutable position. Those skilled in the art will readily recognize substitutable positions on, for example, ($C_1$-$C_6$)alkyl, phenyl, pyridyl, and benzothiazolyl groups.

Where the term "alkyl" is used, either alone or within other terms such as "haloalkyl" and "alkylsulfonyl", it embraces linear, i.e., straight, and branched chain groups having one to about twelve carbon atoms. Preferred alkyl groups are "lower alkyl" groups having one to about ten carbon atoms. More preferred are lower alkyl groups having one to about six carbon atoms. Examples of alkyl include, but are not limited to, methyl, ethyl, n-propyl, iso-propyl, n-butyl, sec-butyl, tert-butyl, n-pentyl, and sec-pentyl and the like. Preferred alkyl groups are $C_1$-$C_6$ alkyl groups. Especially preferred alkyl groups are methyl, ethyl, propyl, butyl, 3-pentyl. The term $C_1$-$C_6$ alkyl as used herein includes alkyl groups having from 1 to 6 carbon atoms. Preferred examples are methyl and ethyl.

"Alkylsulfonyl" embraces alkyl groups attached to a sulfonyl group, where alkyl is defined as above, i.e., a group of the formula —$SO_a$(alkyl). More preferred alkylsulfonyl groups are "lower alkylsulfonyl" groups having one to six carbon atoms. Examples of such lower alkylsulfonyl groups include methylsulfonyl, ethylsulfonyl and propylsulfonyl.

The term "alkylsulfinyl" embraces groups containing a linear or branched alkyl group, of one to ten carbon atoms, attached to a divalent —S(=O)— atom.

The terms "N-alkylamino" and "N,N-dialkylamino" denote amino groups which have been substituted with one alkyl group and with two alkyl groups, respectively. More preferred alkylamino groups are "lower alkylamino" groups having one or two alkyl groups of one to six carbon atoms, attached to a nitrogen atom. Suitable "alkylamino" may be mono or dialkylamino such as N-methylamino, N-ethylamino, N,N-dimethylamino, N,N-diethylamino or the like.

The term "alkylthio" embraces groups containing a linear or branched alkyl group, of one to ten carbon atoms, attached to a divalent sulfur atom. An example of "alkylthio" is methylthio, ($CH_3$—S—).

The term "cycloalkyl" embraces groups having three to ten carbon atoms. More preferred cycloalkyl groups are "lower cycloalkyl" groups having three to seven carbon atoms, i.e., $C_3$-$C_7$ cycloalkyl. Examples include groups such as cyclopropyl, cyclobutyl, cyclopentyl, cyclohexyl and cycloheptyl.

In the term "$C_3$-$C_7$ cycloalkylalkyl", the $C_{3-7}$ cycloalkyl group is attached to the parent molecular moiety through the alkyl, preferably a $C_1$-$C_6$, more preferably a $C_1$-$C_4$ alkyl, group. This term encompasses, but is not limited to, cyclopropylmethyl, and cyclohexylmethyl.

By "carboxamido" as used herein is meant groups of the formula —C(O)NR$^a$R$^b$ where R$^a$ and R$^b$ are the same or different and represent hydrogen or alkyl. Preferred carboxamido groups are those where both of R$^a$ and R$^b$ are hydrogen.

The term "alkenyl" embraces unsaturated straight and branched chain groups having two to about ten carbon atoms. Such groups contain at least one carbon-carbon double bond which may occur at any stable point along the chain. Examples of alkenyl groups include, but are not limited to such groups as ethenyl and propenyl.

The term "alkynyl" embraces straight and branched chain groups having two to about ten carbon atoms and at least one carbon-carbon triple bond. The carbon-carbon triple bond may occur at any stable point along the chain. Examples of alkynyl groups include, but are not limited to such groups as ethynyl and propynyl.

"Alkoxy" represents an alkyl group as defined above attached to the parent molecular moiety through an oxygen bridge. Examples of alkoxy include, but are not limited to, methoxy, ethoxy, n-propoxy, iso-propoxy, n-butoxy, 2-butoxy, tert-butoxy, n-pentoxy, 2-pentoxy, 3-pentoxy, isopentoxy, neopentoxy, n-hexoxy, 2-hexoxy, 3-hexoxy, and 3-methylpentoxy. More preferred alkoxy groups include methoxy, ethoxy, isopropoxy, and isobutoxy.

As used herein, "alkanoyl" and "acyl" refer to an alkyl group as defined above attached through a carbonyl bridge, i.e., —CO(alkyl). Examples include acetyl, propionyl, and butyryl.

The term "aryl" is used to indicate aromatic groups that contain only carbon atoms in the ring structure. Thus, the term "aryl" refers to an aromatic hydrocarbon ring system containing at least one aromatic ring. The aromatic ring may optionally be fused or otherwise attached to other aromatic hydrocarbon rings or non-aromatic hydrocarbon rings. Examples of aryl groups are, for example, phenyl, naphthyl, 1,2,3,4-tetrahydronaphthalene, indanyl, and biphenyl. Preferred aryl groups include phenyl, naphthyl, including 1-naphthyl and 2-naphthyl, and acenaphthyl. More preferred aryl groups include phenyl and napthyl. The aryl groups herein are unsubstituted or, as specified, substituted in one or more substitutable positions with various groups. Thus, such aryl groups are optionally substituted with, for example,one, two, three, or four of $C_1$-$C_6$ alkyl, $C_1$-$C_6$ alkoxy, halogen, hydroxy, cyano, nitro, amino, ($C_1$-$C_6$)alkylamino, di($C_1$-$C_6$) alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, or ($C_1$-$C_6$)alkylamino ($C_1$-$C_6$)alkyl.

The term "haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1). Examples of haloalkyl include, but are not limited to, trifluoromethyl, trichloromethyl, pentafluoroethyl, and pentachloroethyl. Preferred haloalkyl groups are halo($C_1$-$C_6$)alkyl groups; particularly preferred are trifluoromethyl, perfluoropropyl, and difluoromethyl.

By "haloalkoxy" as used herein is meant represents a haloalkyl group, as defined above, attached through an oxygen bridge to a parent group. Preferred haloalkoxy groups are halo($C_1$-$C_6$)alkoxy groups. Examples of haloalkoxy groups are trifluoromethoxy, 2,2-difluoroethoxy, 2,2,3-trifluoropropoxy and perfluoroisopropoxy. The term "halogen" indicates fluorine, chlorine, bromine, and iodine.

The term "heteroaryl" includes aromatic 5 to 6 membered heteromonocyclyl groups containing 1 to 4 nitrogen atoms, for example, pyrrolyl, pyrrolinyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; aromatic condensed heterocyclyl groups containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b]pyridazinyl, etc.], etc.; aromatic 5 to 6-membered heteromonocyclic groups containing an oxygen atom, for example, pyranyl, 2-furyl, 3-furyl, etc.; condensed aromatic heterocyclyl groups containing an oxygen atom, for example, benzofuranyl [e.g., benzofur-2-yl, benzofur-3-yl, etc.] and benzopyranyl [e.g., benzopyran-2-yl, benzopyran-3-yl, etc.]; aromatic 5 to 6-membered heteromonocyclic groups containing a sulfur atom, for example, 2-thienyl, 3-thienyl, etc.; aromatic 5- to 6-membered heteromonocyclic groups containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.] etc.; aromatic condensed heterocyclyl groups containing 1 to 2 oxygen atoms and 1 to 3 nitrogen atoms [e.g. benzoxazolyl, benzoxadiazolyl, etc.]; aromatic 5 to 6-membered heteromonocyclic groups containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.] etc.; aromatic condensed heteroaryl groups containing 1 to 2 sulfur atoms and 1 to 3 nitrogen atoms [e.g., benzothiazolyl, benzothiadiazolyl, etc.] and the like. The term also embraces groups where the heteroaryl radicals are fused with aryl groups or saturated or partially saturated rings. Examples of such fused bicyclic radicals include benzofuran, benzothiophene, 4,5,6,7-tetrahydro-benzo[b]thiophene, 5,6,7,8-tetrahydro-4H-chromene, 4,5,6,7-tetrahydro-1H-indole, 5,6,7,8-tetrahydroquinoline, and the like.

As used herein, the term "heterocycloalkyl" is intended to mean a stable 5- to 7-membered monocyclic or 7- to 10-membered bicyclic ring system which contains at least one non-aromatic ring wherein said ring consists of carbon atoms and from 1 to 4 heteroatoms independently selected from the group consisting of N, 0 and S. The heterocycloalkyl ring or heterocycloalkyl bicyclic ring system may be fused to a benzene ring. A nitrogen in the heterocycle may optionally be quaternized. It is preferred that when the total number of S and 0 atoms in the heterocycloalkyl group exceeds 1, then these heteroatoms are not adjacent to one another. It is also preferred that the total number of S and 0 atoms in the heterocycloalkyl is not more than 1. Examples of heterocycloalkyl groups include but are not limited to tetrahydroquinolinyl, tetrahydroisoquinolinyl, pyrrolyl, piperazinyl, piperidinyl, tetrahydrofuranyl, morpholinyl, azetidinyl, 2H-pyrrolyl.

Sulfur and nitrogen atoms in nitrogen and sulfur-containing groups, e.g., the D groups, of the compounds of the invention may be oxidized to provide the corresponding N-oxide, sulfoxide and sulfone containing compounds. Accordingly, the invention encompasses all such compounds.

The compounds of the invention may have one or more asymmetric centers. Such compounds may be present in one or more stereoisomeric forms. These compounds can be, for example, racemates, optically active forms, or enantiomerically enriched mixtures of stereoisomers. Where desired, the single enantiomers, i.e., optically active forms, can be obtained by known procedures, e.g., by asymmetric synthesis, by synthesis from optically active starting materials, or by resolution of the racemates. Resolution of the racemates can be accomplished by conventional methods such as, for example, crystallization in the presence of a resolving agent; dramatizations with an enantiomerically pure or enriched resolving reagent followed by isolation of the desired isomer; or chromatography, using, for example a chiral HPLC column.

Non-toxic pharmaceutically acceptable salts include, but are not limited to salts of inorganic acids such as hydrochloric, sulfuric, phosphoric, diphosphoric, hydrobromic, and nitric or salts of organic acids such as formic, citric, malic, maleic, fumaric, tartaric, succinic, acetic, lactic, methanesulfonic, p-toluenesulfonic, 2-hydroxyethylsulfonic, salicylic and stearic. Similarly, pharmaceutically acceptable cations include, but are not limited to sodium, potassium, calcium, aluminum, lithium and ammonium. Those skilled in the art will recognize a wide variety of non-toxic pharmaceutically acceptable addition salts. The present invention also encompasses prodrugs of the compounds of Formula I.

The present invention also encompasses the acylated prodrugs of the compounds of Formula I. Those skilled in the art will recognize various synthetic methodologies, which may be employed to prepare non-toxic pharmaceutically acceptable addition salts and acylated prodrugs of the compounds encompassed by Formula I.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

With respect to treatment of, for example, gout, administration of the compound(s) of this invention is/are not limited to a particular mode, and could be administered systemically or topically to the eye in an appropriate ophthalmic solution. The compounds of the invention may be administered in combination therapy with other known hypouremic agents. Also, the compounds of the invention may be administered with compounds useful in the treatment of myeloid leukemia, myeloid dysplasia, pernicious anemia, psoriasis, diabetes mellitus and renal disease.

Dosage levels on the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 1000 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

The compounds of the present invention may be prepared by use of known chemical reactions and procedures. General methods for synthesizing the compounds are presented below. It is understood that the nature of the substituents required for the desired target compound often determines the preferred method of synthesis. All variable groups of these methods are as described in the generic description if they are not specifically defined below. More detailed procedures for particular examples are presented below in the experimental section.

Methods of Preparation

Compounds of the invention where D in Formula I is a 7-azaindole moiety with an substituent ($R_3$) at the 4, 5 or 6-position, Z is a methylene and Ar is a substituted benzothiazole can be conveniently prepared from the corresponding substituted 2-aminopyridine using general Scheme A set forth below. In this method, the desired 2-aminopyridine A-1 is acylated with pivaloyl chloride and triethylamine to provide pyridine A-2. Subsequent treatment with tert-butyllithium (2 equiv.) and alkylation with methyl iodide provides the methylpyridine derivative A-3. Formation of the dianion with tert-butyllithium (2 equiv.) followed by quenching with a formyl cation equivelent such as N,N-dimethylformamide and treatment, with aqueous acid provides the desired substituted azaindole A-4. The 3-acetonitrile derivative A-6 is typically prepared via the grammine A-5. The azaindole moiety in a weak acid solution, for example, acetic acid in ethanol, is treated with aqueous formaldehyde and dimethyl amine in an alcohol solvent. The 3-(dimethylamino)methyl indole product can then be treated with sodium or potassium cyanide in N,N-dimethylformamide at elevated temperatures to provide the 3-acetonitrile substituted indole intermediate.

Treatment of a nitrile A-6 with a strong base such as, for example, sodium hydride, butyl lithium or sodium tert-butoxide, in a polar aprotic solvent such as acetonitrile, tetrahydrofuran or N,N-dimethylformamide followed by an treatment with an alkylating agent, e.g., ethyl or tert-butyl bromoacetate, provides the desired N-alkylated product A-8. Alternativly, phase transfer catalysis can be used in a biphasic solvent system. A general review of such alkylations can be found in Sundberg, R. J. *Indoles*; Chapter 11, Academic Press Inc., San Diego, Calif., 1996. Condensation with a suitable 2-amino thiophenol hydrochloride salt A-9 provides benzothiazole intermediate A-10. These reactions are most often carried out in an alcohol solvents at elevated temperatures; however, other solvents like N,N-dimethylformamide and N-methylpyrrolidone can be used or the reactions can be carried out in the absence of solvents altogether. The scope of the reaction conditions useful for this transformation have been described previously (U.S. Pat. No. 5,700,819). General methods for the preparation of various substituted 2-amino thiophenols are also well known (*J. Med. Chem.* 1991, 34, 108 and *Chem. Pharm. Bull.* 1994, 42, 1264). In general, the best method of synthesis is determined by such factors as availability of starting materials and ease of synthesis. Deprotection of the alkanoic acid moiety A-10 can be carried out by methods common to those skilled in the art to result in target compounds A-11. The method used in the deprotection depends on the type of protecting group. A description of such protecting groups and methods for deprotecting them may be found in: *Protective Groups in Organic Synthesis*, Second Edition, T. W. Green and P. G. M. Wuts, John Wiley and Sons, Ney York, 1991. When a methyl or ethyl ester is used, an aqueous sodium hydroxide solution in ethanol or dimethoxyethane is conveniently employed for its removal.

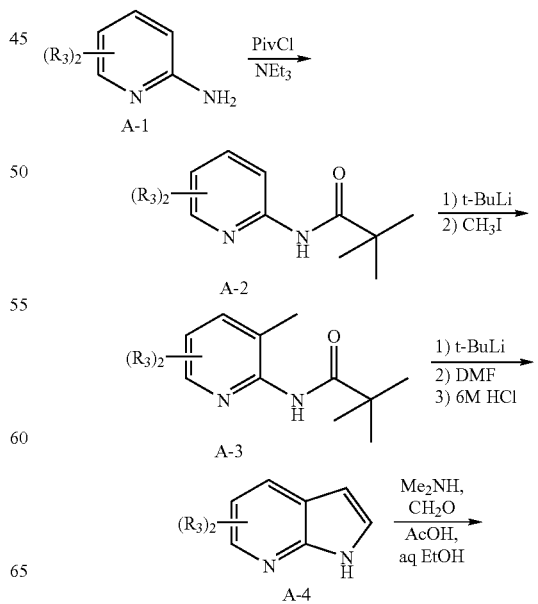

Scheme A

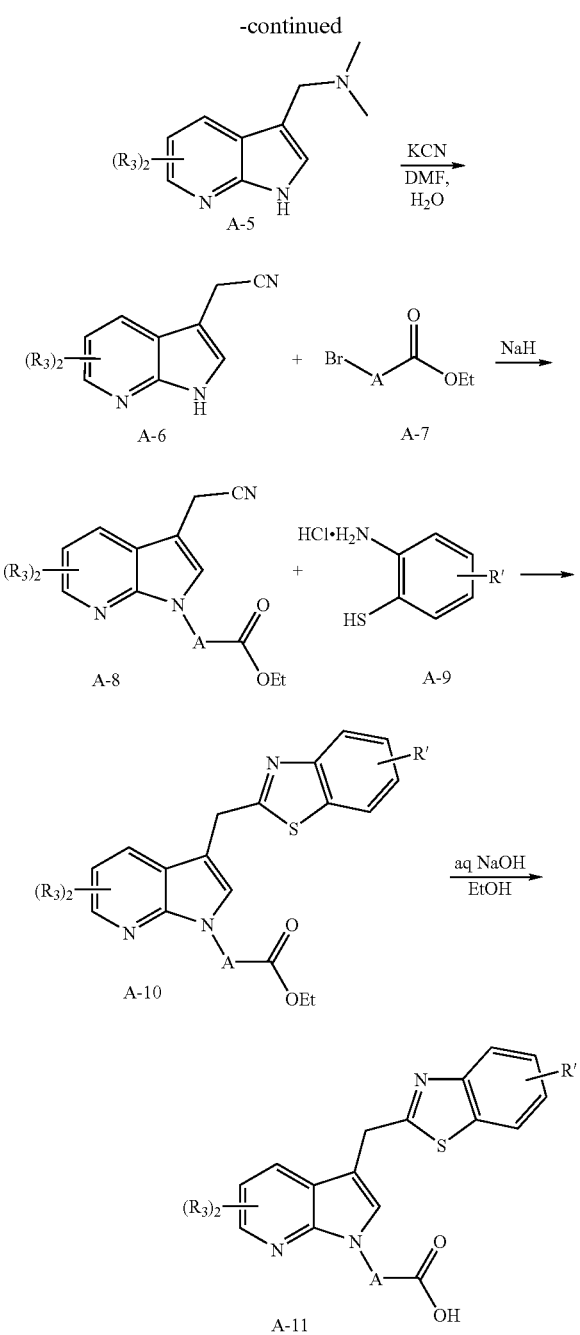

Other examples where A-4 is a substituted 4,5 or 6-azaindole can be prepared using the same method except the 4,5 or 6-azaindole is used in place of the substituted 7-azaindole A-4. Synthetic methods for the preparation of these azaindole intermediates can be found in the literature (Hands, et al. *Synthesis* 1996, 7, 877; Sakamoto, et al. *Heterocycles* 1992, 12, 2379; Macor, et al. *Heterocycles* 1990, 31, 805; Mahadevan, et al. *J. Heterocycl. Chem.* 1992, 29, 359; Dormoy, et al. *Tetrahedron* 1993, 49, 2885; Meade, et al. *J. Heterocycl. Chem.* 1996, 33, 303; Takao, et al. *Chem. Phar. Bull.* 1987, 35, 1823).

In general, compounds of the invention where D in Formula I is a pyrrole substituted with A attached on the ring nitrogen, Y attached at the 3-position and group(s) $R_3$ at the 4 and/or 5-positions can be prepared using general method B. In this method, the substituted 2-aminovinyl bromide or iodide B-1 is treated with bromide B-2 using an amine base like triethylamine in a halogenated solvent to give the alkylated product B-3. Subsequent palladium catylized cyclization gives the 3-aceticacid or ester substituted pyrrole B-4. Treatment with a strong base such as, for example, sodium hydride, butyl lithium or sodium tert-butoxide, in a polar aprotic solvent such as acetonitrile followed by an treatment with an alkylating agent, such as tert-butyl bromoacetate, provides the desired N-alkylated product B-6. Condensation with a suitable 2-amino thiophenol hydrochloride salt A-9 provides benzothiazole intermediate B-7. These reactions are most often carried out in an alcohol solvents at elevated temperatures or in the absence of solvents altogether. Deprotection of the ester intermediate provides the target compound B-8.

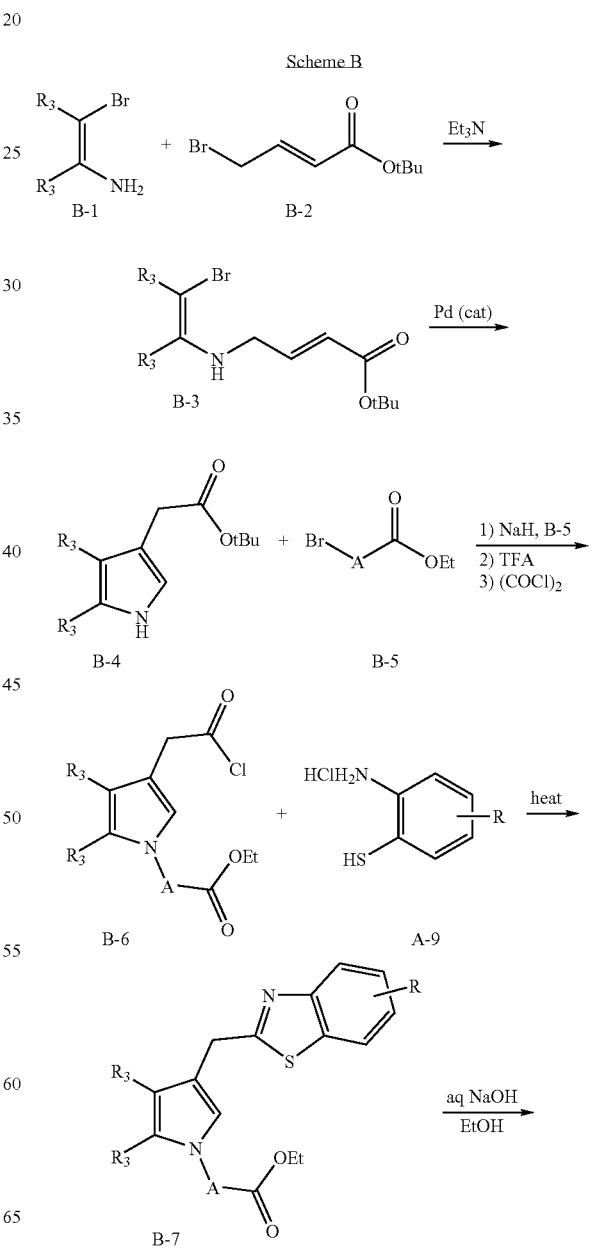

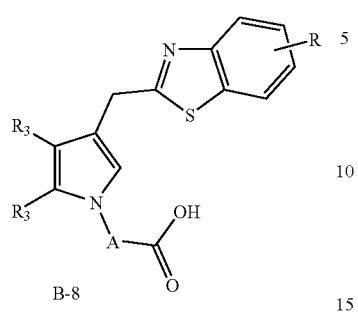

B-8

The compounds of the invention where D in Formula I is pyridine, Ar is benzothiazoyl and where $R_{5a}$ and $R_{5b}$ and $R_{5c}$ represent positions 2, 6 and 4 on the pyridine ring respectively can be conveniently prepared from a substituted pyridine using general Scheme C set forth below:

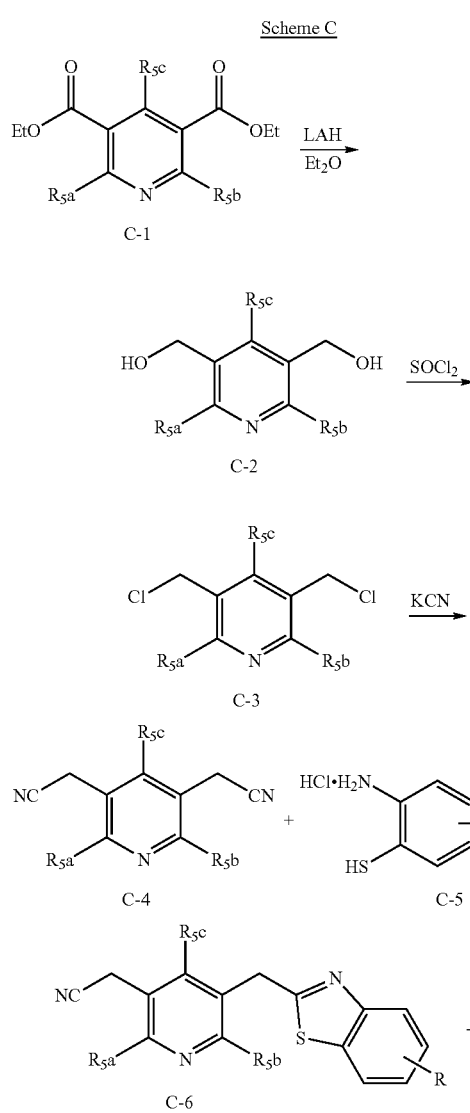

Scheme C

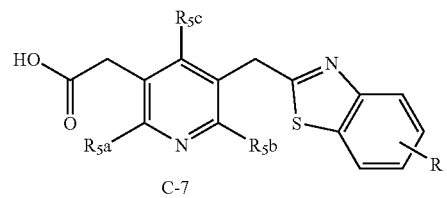

C-7

In this method, treatment of pyridine diester or diacid C-1 with a hydride reducing agent such as lithium aluminum hydride (LAH) in a suitable solvent such as Et$_2$O or THF provides the pyridine diol C-2. Subjecting the diol to thionyl chloride, neat or in a suitable polar aprotic solvent such as THF or DMF forms pyridine dichloride C-3. Subsequent treatment with a cyanide salt such as potassium cyanide or sodium cyanide in DMF/H$_2$O to provides bis-nitrile C-4. Alternatively pyridine bis-nitrile C-4 may be obtained from pyridine diol C-2 using the Mitsunobu method (Tsunoda, T.; Uemoto, K.; Nagino, C.; Kawamura, M.; Kaku, H.; Ito, S. *Tetrahedron Lett.* 1999, 40, 7355). Condensation of C-4 with a suitable 2-amino thiophenol hydrochloride salt provides benzothiazole intermediate C-6. These reactions are most often carried out in alcohol solvents at elevated temperatures or in the absence of solvents altogether. The scope of the reaction conditions useful for this transformation have been described previously (U.S. Pat. No. 5,700,819). General methods for the preparation of various substituted 2-amino thiophenols are also well known (*J. Med. Chem.* 1991, 34, 108 and *Chem. Pharm. Bull.* 1994, 42, 1264).

Treatment of nitrile intermediate C-6 with aqueous hydrochloric acid (HCl) provides the target compound.

If not commercially available, pyridine bis-esters B-8 can be prepared substantially using the Hantzsch dihydropyridine method as described below in Scheme D. A description of the scope of such methods can be found in: Sausins, A.; Duburs, G. *Heterocycles* 1988, 27, 269 and Stout, D. M.; Meyers, A. I. *Chem. Rev.* 1982, 82, 223.

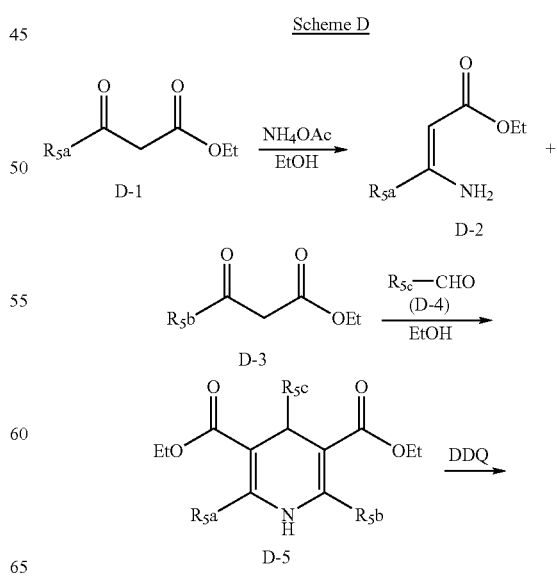

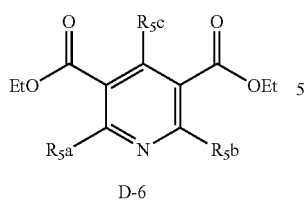

D-6

In Method D, enamine ester D-2, prepared from β-ketoester D-1 (commercially available or prepared according to the procedures described: Li, An-Hu; Moro, S.; Melman, N.; Ji, Xiao-duo; Jacobson, K. A. *J. Med. Chem.* 1998, 41, 3186) and ammonium acetate in a polar solvent such as ethanol, and β-ketoester D-3 are mixed with aldehyde $R_{5c}$—CHO (D-4) in a suitable protic solvent such as EtOH to produce dihydropyridine D-5. Oxidation to the pyridine D-6 may be accomplished using a wide variety of methods. One convienet method utilizes 2,3-dichloro-5,6-dicyano benzoquinone(DDQ). Other oxidation procedures include the use of $MnO_2$, $KMnO_4$, $HNO_3$ or PCC used either as a reagent or adsorbed onto clay or silica. A description of these methods can be found in Vanden Eynde, J.-J.; D'orazio, R.; Van Haverbeke, Y. *Tetrahedron* 1994, 50, 2479 and Sausins, A.; Duburs, G. *Heterocycles* 1988, 27, 291. Examples where $R_{5c}$ is hydrogen can be prepared by using method D where $R_{5c}$ is antipyrine (4-(2,3-dimethyl-1-phenyl-3-pyrazolin-5-one)) or 2-pyrrole and the dihydropyridine intermediate D-5 is treated with aqueous HCl to provide the target pyridine product D-6. A description of these procedures can be found in Vanden Eynde, J -J.; Mayence, A.; Maquestiau, A.; Anders, E. *Heterocycles* 1994, 37, 815; Sausins, A.; Duburs, G. *Heterocycles* 1988, 27, 269; Stout, D. M.; Meyers, A. I. *Chem. Rev.* 1982, 82, 223.

Alternatively, the substituted pyridine bis-ester intermediates, may be prepared from 4-oxo-pyran dicarboxylic acid esters, E-1 as illustrated in Scheme E. The starting substituted pyrans may be prepared from a variety of methods. One convenient method has been described by Yamato (Yamato, M.; Kusunoki, Y. *Chem. Pharm. Bull.* 1981, 29, 1214.). Treatment of the substituted pyran E-1 with ammonia or aqueous ammonia (Cliffton, M. D.; Looker, J. H.; Prokop, R. L. *J. Org. Chem.* 1979, 44, 3408.) provides 4-hydroxy pyridine E-2. Subsequent functionalization of the $R_{5c}$ substituent from the phenol can be carried out using a variety of known methods. For example, conversion to 4-halopyrines has been described by Chambers (*J. Org. Chem.* 1979, 44, 3408; Chambers, R. D.; Hutchinson, J.; Musgrave, W. K. R. *J. Chem. Soc.* 1964, 3573 and U.S. Pat. No. 4,797,149). Ethers may be formed at the 4 position by treating hydroxy pyridine, E-2, with a base such as potassium carbonate and an alkyl halide. Such reactions are described by Hegde (Hegde, S. G. *J. Org. Chem.* 1991, 56, 5726.).

Scheme E

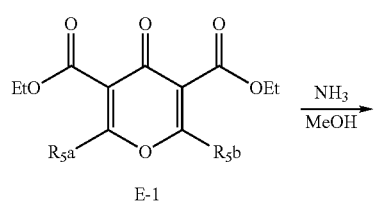

E-1

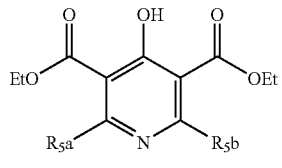

E-2

Compounds of formula I, where D is a substituted pyridine, $R_{5a}$ is a substituted alkyl, aryl, aminoalkyl or ether and Ar is benzothiazoyl can be conveniently prepared from nicotinic acid derivative F-1 using general Scheme F set forth below:

Scheme F

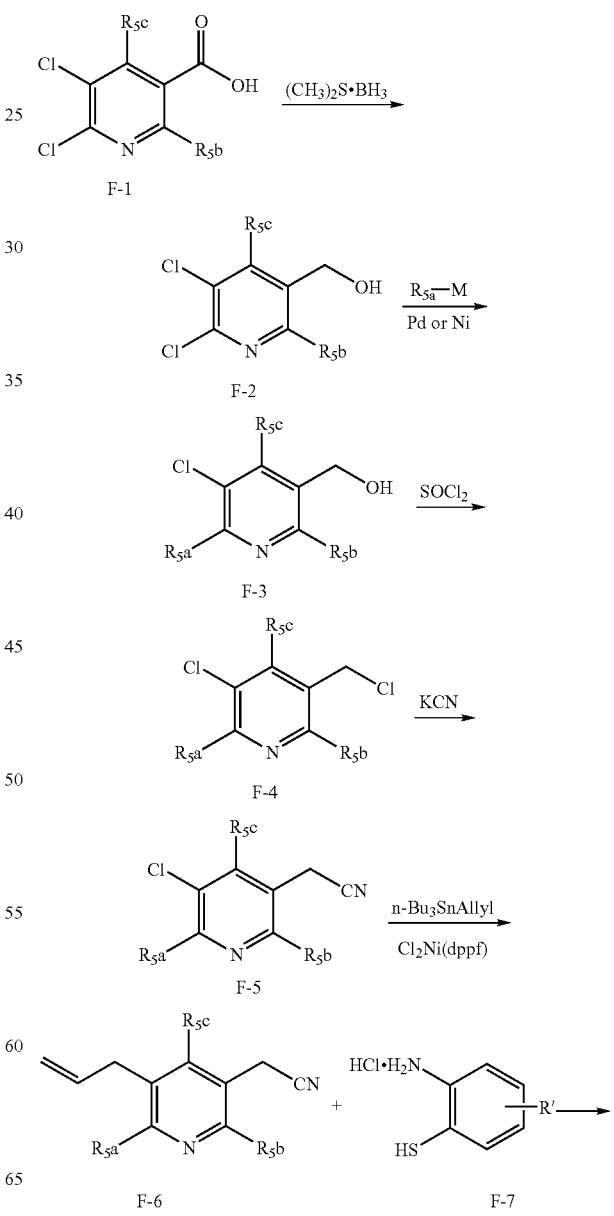

-continued

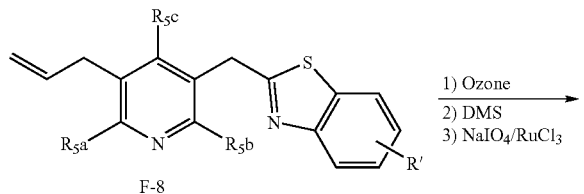
F-8

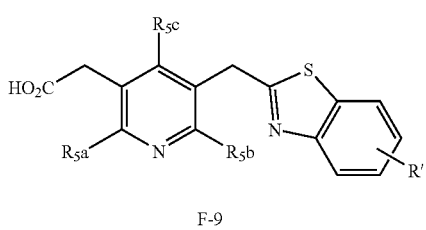
F-9

Nicotinic acid derivatives F-1, either commercially availible or prepared using known methods, can be reduced with a reducing reagent like borane-methyl sulfide to give alcohol F-2. The $R_{5a}$ substituent can be introduced using a variety of methods depending on the particular group. In general, metal coupling reactions using magnesium, lithium, boron, zinc or tin are convienent. For some examples, protecting groups may be required and the specific order of steps or reagents used may need to be modified to optimize the process (Lohse, O.; Thevenin, P.; Waldvogel, E. *Syn. Lett.* 1999, 45). Subsequent treatment with thionyl chloride in THF provides chloride F-4 which can be converted to nitrile F-5 by treatment with a cyanide salt such as sodium or potassium cyanide. Transition metal catalyzed cross-coupling with allyl-tri-n-butyltin using catalytic 1,1-bis (diphenylphosphino)ferrocenedichloronickel(II)dichloride ($Cl_2Ni(dppf)$) in an oxygen free polar solvent such as acetonitrile or DMF. Provides allyl intermediate F-6. Condensation with 2-amino thiophenol hydrochloride salt F-7 using conditions previously described provides the benzothiazole F-8. A two step oxidation starting with a reductive ozonolysis followed by a ruthenium/periodate mixture provides the target carboxylic acid F-9.

Similarly, other compounds of formula D, where D is a substituted pyridine, $R_{5b}$ is a substituted alkyl, aryl, aminoalkyl or ether and Ar is benzothiazoyl can be conveniently prepared using general Scheme G set forth below using nicotinic acid derivatives as previously described in general Scheme F:

Scheme G

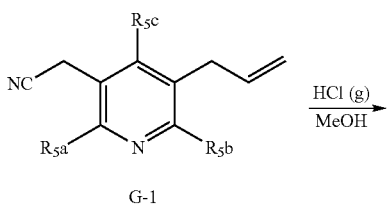
G-1

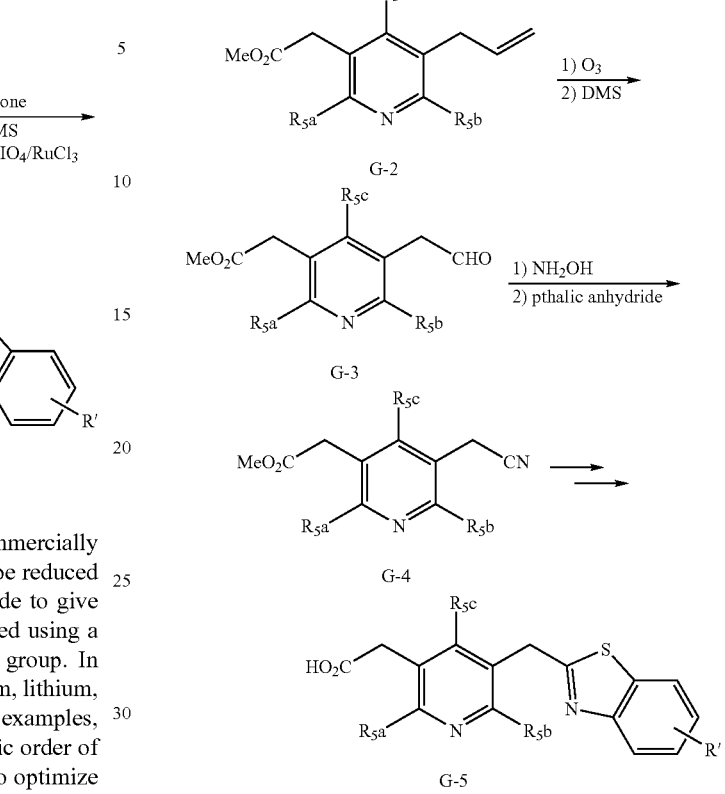

In this general method, esterification of nitrile G-1 using known methods such as hydrochloric acid in methanol provides ester G-2. Oxidative cleavage with ozone followed by treatment with dimethyl sulfide (DMS) provides aldehyde G-3. Subsequent conversion to nitrile G-4 is conveniently carried out by a two step procedure using hydroxyl amine and pthalic anhydride (Wang, E. C.; Lin, G. J., *Tetrahedron lett.* 1998, 39, 4047). Intermediate G-4 is readily converted to target compounds G-5 using general methods already described.

An additional method for preparing certain compounds of Formula I, where D is a substituted pyridine, can be prepared using general method H set forth below. In this method, a substituted Nicotinic acid or ester H-1, prepared using known methods (Tingoli, et al. *J. Org. Chem.* 1993, 58, 6097; Kao, et al. *J. Het. Chem.* 1991, 28, 1315; Bohlmann, *Chem. Ber.* 1957, 90, 2265; Singh, et al. *Tetrahedron* 1998, 54, 935; Inoue, *Synthesis* 1997, 1, 113; Yamauchi, et al. *J. Heterocycl Chem,* 1997, 34, 93; Krapcho, et al. *J. Heterocycl Chem* 1997, 34, 27; Okada, et al. *Heterocycles* 1997, 46, 129) is brominated with NBS (N-bromosuccinamide) or bromine to give bromide H-2. Alternatively, bromide H-2 can be prepared directly using the general procedure of Doehner (U.S. Pat. No. 4,925,944, 1990). The carboxcyclic acid or ester moiety can then be homologated or modified in some way using known methods to provide ester intermediate H-3. It is understood that the specific steps used will depend on the desired A-group. Subsequent introduction of the sidechain, Z-Ar is conveniently carried out using a transition metal catalyzed coupling reaction where a palladium or Nickel catalyst is used to couple a boron, tin, magnesium or zinc sidechain intermediate to give the coupled product H-4. If Z is a methylene and Ar is a heterocycle readily available from a nitrile, then bromide H-3 can be coupled with the desired cyanoacetate and subsequently decarboxylated (Hartwig, et al. *J. am. Chem. Soc.* 2001, 123, 4641). Finally, hydrolysis of the ester provides the target compounds H-5.

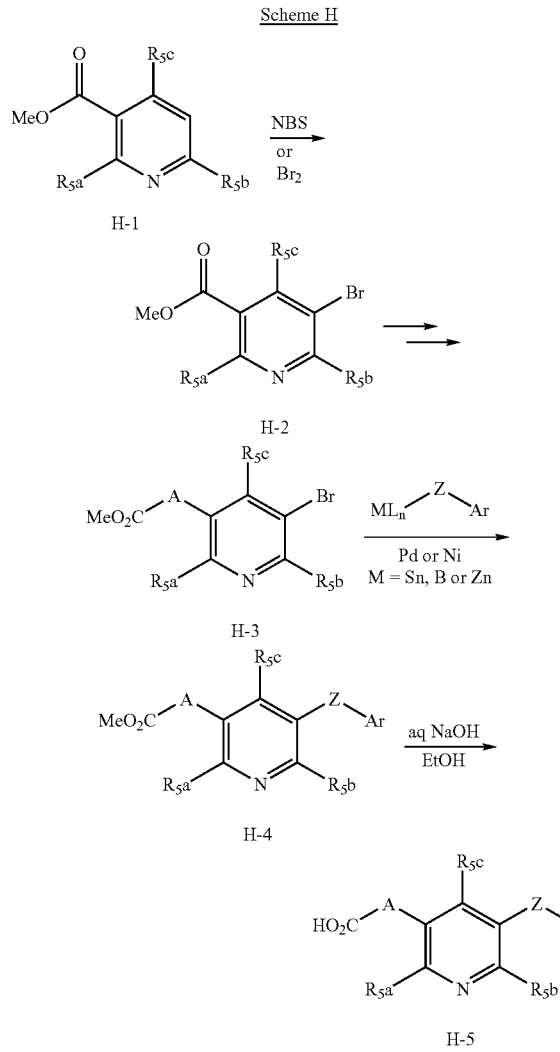

Those having skill in the art will recognize that the starting materials and reaction conditions may be varied, the sequence of the reactions altered, and additional steps employed to produce compounds encompassed by the present invention, as demonstrated by the following examples. In some cases, protection of certain reactive functionalities may be necessary to achieve some of the above transformations. In general, the need for such protecting groups as well as the conditions necessary to attach and remove such groups will be apparent to those skilled in the art of organic synthesis.

The disclosures of all articles and references mentioned in this application, including patents, are incorporated herein by reference.

The preparation of the compounds of the present invention is illustrated further by the following examples, which are not to be construed as limiting the invention in scope or spirit to the specific procedures and compounds described in them.

EXAMPLE 1

Preparation of [6-Ethyl-3-(4,5,7-trifluoro-benzothiazol-2-ylmethyl)-pyrrolo[2,3-b]pyridin-1-yl]-acetic acid

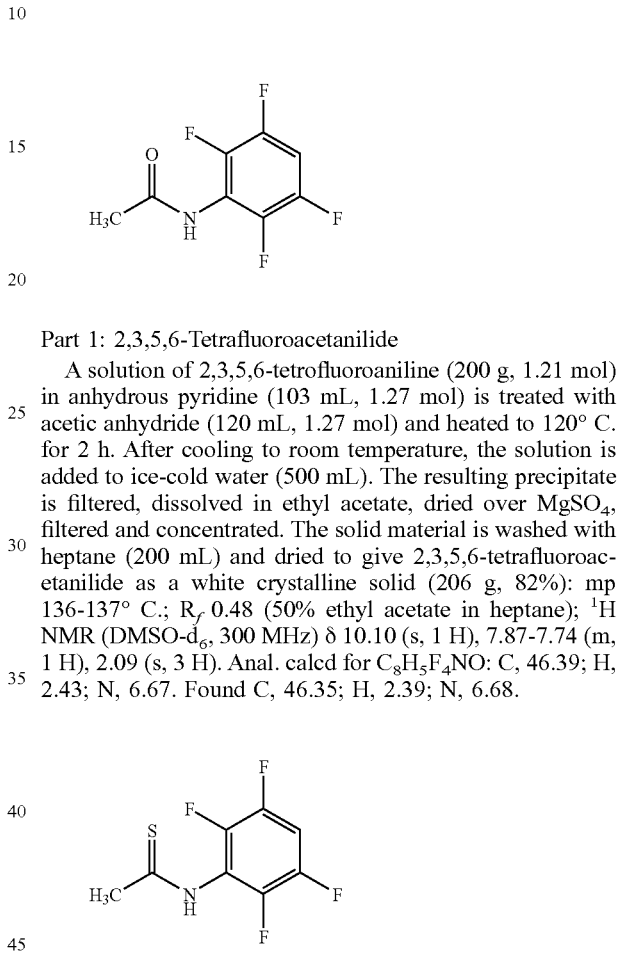

Part 1: 2,3,5,6-Tetrafluoroacetanilide

A solution of 2,3,5,6-tetrofluoroaniline (200 g, 1.21 mol) in anhydrous pyridine (103 mL, 1.27 mol) is treated with acetic anhydride (120 mL, 1.27 mol) and heated to 120° C. for 2 h. After cooling to room temperature, the solution is added to ice-cold water (500 mL). The resulting precipitate is filtered, dissolved in ethyl acetate, dried over MgSO$_4$, filtered and concentrated. The solid material is washed with heptane (200 mL) and dried to give 2,3,5,6-tetrafluoroacetanilide as a white crystalline solid (206 g, 82%): mp 136-137° C.; R$_f$ 0.48 (50% ethyl acetate in heptane); $^1$H NMR (DMSO-d$_6$, 300 MHz) δ 10.10 (s, 1 H), 7.87-7.74 (m, 1 H), 2.09 (s, 3 H). Anal. calcd for C$_8$H$_5$F$_4$NO: C, 46.39; H, 2.43; N, 6.67. Found C, 46.35; H, 2.39; N, 6.68.

Part 2: 2,3,5,6-Tetrafluorothioacetanilide

A flame-dried, 4-necked 5,000 mL round-bottomed flask is charged with phosphorous pentasulfide (198 g, 0.45 mol) and diluted with anhydrous benzene (3,000 mL, 0.34 M). 2,3,5,6-tetrafluoroacetanilide (185 g, 0.89 mol) is added in one portion and the bright yellow suspension is heated to a gentle reflux for 3 h. The solution is cooled to 0° C. and filtered. The insoluble material is washed with ether (2×250 mL) and the combined filtrate is extracted with 10% aq NaOH (750 mL, 500 mL). After cooling the aqueous layer to 0° C., it is carefully acidified with conc. HCl (pH 2-3). The precipitated product is collected by filtration and washed with water (500 mL). The yellow-orange material is disolved in ethyl acetate (1,000 mL), dried over MgSO$_4$ and activated charcoal (3 g), filtered through a short pad of silica (50 g), and concentrated. The resulting solid is triturated with heptane (500 mL) and filtered to give 2,3,5,6-tetrafluorothioacetanilide (174.9 g, 88%): mp: 103-104° C.; R$_f$ 0.67 (50% ethyl acetate in heptane); $^1$H NMR (DMSO-d$_6$, 300 MHz) δ 11.20 (s, 1 H), 8.00-7.88 (m, 1 H), 2.66 (s, 3 H).

Anal. calcd for C$_8$H$_5$F$_4$NS: C, 43.05; H, 2.26; N, 6.28. Found C, 43.10; H, 2.23; N, 6.19.

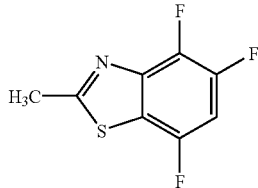

Part 3: 4,5,7-Trifluoro-2-methylbenzothiazole

A flame-dried 5,000 mL round-bottomed flask equipped with over-head stirrer is charged with sodium hydride (15.9 g, 0.66 mol) and diluted with anhydrous toluene (3,000 mL, 0.2 M). The suspension is cooled to 0° C., and treated with 2,3,5,6-tetrafluorothioacetanilide (134 g, 0.60 mol) in one portion. The solution is warmed to room temperature over 1 h, then heated to a gentle reflux. After 30 min, N,N-dimethylformamide (400 mL) is carefully added and the mixture is stirred for an additional 2 h. The solution is cooled to 0° C. and added to ice-water (2,000 mL). The solution is extracted with ethyl acetate (1,500 mL) and washed with saturated aq NaCl (1,000 mL). The organic layer is concentrated to dryness, diluted with heptane and successively washed with water (300 mL) and saturated aq NaCl (1,000 mL). The organic layer is dried over MgSO$_4$, filtered and concentrated to give 4,5,7-trifluoro-2-methylbenzothiazole (116.8 g, 96%) as a light brown solid: mp: 91-92° C.; R$_f$ 0.56 (30% ethyl acetate in heptane); $^1$H NMR (DMSO-d$_6$, 300 MHz) δ 7.76-7.67 (m, 1H), 2.87 (s, 3 H);. Anal. calcd for C$_8$H$_4$F$_3$NS: C, 47.29; H, 1.98; N, 6.82; S, 15.78. Found C, 47.56; H, 2.07; N, 6.82; S, 15.59.

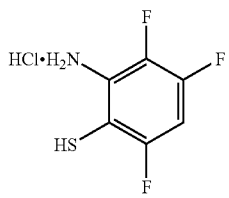

Part 4: 2-Amino-3,4,6-trifluorothiophenol Hydrochloride

A solution of 4,5,7-trifluoro-2-methylbenzothiazole (25.0 g, 123 mmol) in ethylene glycol (310 mL, 0.4 M) and 30% aq NaOH (310 mL, 0.4 M) is degassed using a nitrogen stream and subsequently heated to a gentle reflux (125° C.) for 3 h. The solution is cooled to 0° C. and acidified to pH 3-4 using conc. HCl (appox. 200 mL). The solution is extracted with ether (750 mL) and washed with water (200 mL). The organic layer is dried over Na$_2$SO$_4$, filtered and treated with 2,2-di-tert-butyl-4-methylphenol (0.135 g, 0.5 mol %). After concentrating to dryness, the crude product is dissolved in anhyd methanol (200 mL) and treated with an HCl solution in 1,4-dioxane (37 mL, 4 N, 148 mmol). The resulting mixture is concentrated to dryness, triturated with isopropylether (100 mL) and filtered to give 2-amino-3,4, 6-trifluorothiophenol hydrochloride (19.3 g, 73%) as a light brown solid that is used without further purification. mp. 121-124 C; R$_f$ 0.43 (30% ethyl acetate in heptane); Anal. calcd for C$_6$H$_5$ClF$_3$NS: C, 33.42; H, 2.34; N, 6.50; S, 14.87. Found C, 33.45; H, 2.27; N, 6.48; S, 14.96.

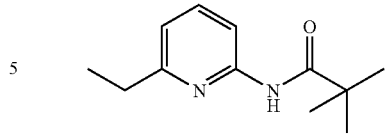

Part 5: N-(6-Ethyl-pyridin-2-yl)-2,2-dimethyl-propionamide

A solution of 6-ethyl-pyridin-2-ylamine (20 g, 0.164 mol) and triethylamine (29.6 mL, 0.213 mol) in dichloromethane (200 mL, 0.8 M) is cooled to 0° C. and carefully treated with pivaloyl chloride (26.2 mL, 0.213 mol). After stirring for 2 h, the solution is quenched with aq NaHCO$_3$, extracted with dichloromethane and concentrated. The resulting oil is filtered through a plug of silica gel using ethyl acetate. The filtrate is concentrated and triterated with heptane to give N-(6-ethyl-pyridin-2-yl)-2,2-dimethyl-propionamide (18.3 g, 54%) as a white crystalline solid. mp 59-62° C.; R$_f$ 0.31 (25% ethyl acetate in hexanes); $^1$H NMR (DMSO-d$_6$, 300 MHz) δ 9.56 (s, 1 H), 7.85 (d, J=8.4 Hz, 1 H), 7.63 (t, J=7.8 Hz, 1 H), 6.93 (d, J=7.5 Hz, 1 H), 2.65 (q, J=7.8 Hz, 2 H), 1.20 (s, 9 H), 1.18 (t, 7.8 Hz, 3 H); LRMS calcd for C$_{12}$H$_{18}$N$_2$O: 206.2; found 206.0 (M)$^+$. Anal. Calcd for C$_{12}$H$_{18}$N$_2$O: C, 69.87; H, 8.80; N, 13.58. Found C, 69.60; H, 8.67; N, 13.42.

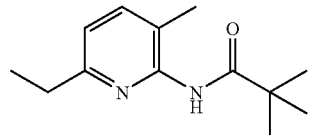

Part 6: N-(6-Ethyl-3-methyl-pyridin-2-yl)-2,2-dimethyl-propionamide

A solution of N-(6-ethyl-pyridin-2-yl)-2,2-dimethyl-propionamide (24.0 g, 0.116 mol) in diethyl ether (600 mL, 0.2 M) is cooled to −78° C. and treated with tert-butyllithium (144 mL 1.7 M in pentane). After the addition is complete the solution is warmed to −20° C. for 2 h, treated with a solution of methyliodide (23 mL, 0.372 mol) in diethylether (10 mL) and warmed to room temperature. After stirring overnight the reaction is diluted with water, extracted with diethyl ether and dried over MgSO$_4$. The resulting solution is filtered through a short pad of silica gel, concentrated and recrystallized from heptane to give N-(6-ethyl-3-methyl-pyridin-2-yl)-2,2-dimethyl-propionamide (17.6 g, 69%) as an off-white crystalline solid. mp 72-75° C.; R$_f$ 0.43 (50% ethyl acetate in hexanes); $^1$H NMR (DMSO-d$_6$, 300 MHz) δ 9.48 (s, 1H), 7.53 (d, J=7.8 Hz, 1 H), 7.48 (d, J=7.5 Hz, 1 H), 2.65 (q, J=7.5 Hz, 2 H), 2.02 (s, 3 H), 1.20 (s, 9 H), 1.18 (t, J=7.5 Hz, 3 H); LRMS calcd for C$_{13}$H$_{20}$N$_2$O: 220.3; found 220.0 (M)$^+$. Anal. Calcd for C$_{13}$H$_{20}$N$_2$O : C, 70.87; H, 9.15; N, 12.72. Found C, 70.70; H, 9.18; N, 12.74.

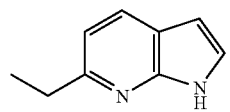

Part 7: 6-Ethyl-1H-pyrrolo[2,3-b]pyridine

A solution of N-(6-ethyl-3-methyl-pyridin-2-yl)-2,2-dimethyl-propionamide (17.6 g, 0.080 mol) in diethyl ether (400 mL) is cooled to −78° C. and treated with tert-butyllithium (99 mL 1.7 M in pentane). After stirring for 1 h, the solution is warmed to −30° C. for 4 h and treated with N,N-dimethylformamide (19.8 mL, 0.26 mol). After stirring an additional 10 min, the suppension is carefully added to 6 N HCl, pre-cooled to −20° C., at a rate such that the temperature warms to about 0° C. After the addition is complete, the aqueous layer is subsequently washed with ethyl acetate and heated to a gentle reflux for 36 h. The resulting solution is cooled to 0° C. and basified with aq 6 N NaOH to pH 10-12. The solution is then extracted with dichloromethane, dried over $MgSO_4$ and concentrated. The resulting pale orange solid is passed through a plug of silica gel with 30% ethyl acetate in hexanes and recrystaliztion from heptane to give 6-ethyl-1H-pyrrolo[2,3-b]pyridine (6.76 g, 58%) as an off-white solid. mp 117-120° C.; $R_f$ 0.57 (50% ethyl acetate in hexanes); $^1H$ NMR (DMSO-$d_6$, 300 MHz) δ 11.46 (s, 1 H), 7.80 (d, J=8.1 Hz, 1 H), 7.33 (d, J=2.7 Hz, 1 H), 6.90 (d, J=8.1 Hz, 1 H), 6.34 (d, J=3.0 Hz, 1 H), 2.76 (q, J=7.5 Hz, 2 H), 1.23 (t, J=7.5 Hz, 3 H); LRMS calcd for $C_9H_{10}N$: 146.0; found 146.0 $(M)^+$. Anal. Calcd for $C_9H_{10}N$: C, 73.94; H, 6.89; N, 19.16. Found C, 73.93; H, 6.91; N, 19.23.

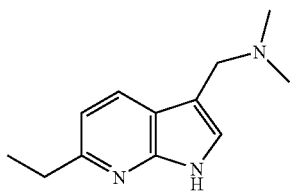

Part 8: 6-Ethyl-1H-pyrrolo[2,3-b]pyridin-3-ylmethyl)-dimethyl-amine

A solution of 40 wt. % aq dimethylamine (9.8 mL, 58 mmol) and acetic acid (2.3 mL, 53 mmol) is cooled to 0° C. and treated with 37 wt. % aq formaldehyde (3.9 mL, 53 mmol) and stirred for 30 min. 6-ethyl-1H-pyrrolo[2,3-b]pyridine (6.7 g, 46 mmol) in ethanol (20 mL) is added and the resulting slurry is stirred for 30 min and subsequently heated to 100° C. for 16 h. After cooling to room temperature, the solution is diluted with water, basified to pH 11 and extracted with dichloromethane. The organic extracts are dried over $MgSO_4$, filtered and concentrated to give a pale yellow solid. Purification by flash column chromatography (20% methanol in chloroform) provided 6-ethyl-1H-pyrrolo[2,3-b]pyridin-3-ylmethyl)-dimethyl-amine (8.22 g, 88%) as a off-white crystalline solid. mp 93-95° C.; $R_f$ 0.30 (50% methanol in chloroform); $^1H$ NMR (DMSO-$d_6$, 300 MHz) δ 11.24 (s, 1 H), 7.84 (d, J=8.1 Hz, 1 H), 7.19 (s, 1 H), 6.88 (d, J=8.1 Hz, 1 H), 3.46 (s, 2 H), 2.75 (q, J=7.5 Hz, 3 H), 2.09 (s, 3 H), 1.23 (t, J=7.5 Hz, 3 H); LRMS calcd for $C_{12}H_{17}N_3$: 203.3; found 203.0 $(M)^+$. Anal. Calcd for $C_{12}H_{17}N_3$: C, 70.90; H, 8.43; N, 20.67. Found C, 70.99; H, 8.44; N, 20.70.

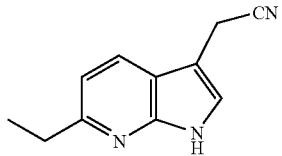

Part 9: 6-Ethyl-1H-pyrrolo[2,3-b]pyridin-3-yl)-acetonitrile

A solution of 6-ethyl-1H-pyrrolo[2,3-b]pyridin-3-ylmethyl)-dimethyl-amine (6.7 g, 33 mmol) in N,N-dimethylformamide (20 mL) is mixed with a second solution of potassium cyanide (2.5 g, 47 mmol) in water (16 mL). Acetic acid (2 mL) is added to the mixture in a dropwise manner and the resulting yellow solution is heated to 110° C. for 3 h. After cooling to room temperature, the solution is diluted with sat'd aq $K_2CO_3$ and extracted with ethyl acetate. The organic extracts are dried over $MgSO_4$, filtered and concentrated to give a pale yellow solid. Purification by flash column chromatography (50% ethyl acetate in hexanes) provided 6-ethyl-1H-pyrrolo[2,3-b]pyridin-3-yl)-acetonitrile (5.69 g, 93%) as an off-white solid. mp 163-170° C.; $R_f$ 0.30 (50% ethyl acetate in hexanes); $^1H$ NMR (DMSO-$d_6$, 300 MHz) δ 11.56 (s, 1 H), 7.89 (d, J=8.1 Hz, 1 H), 7.34 (s, 1H), 6.98 (d, J=8.1 Hz, 1H), 4.01 (s, 2H), 2.77 (q, J=7.5 Hz, 2H), 1.23 (t, J=7.5 Hz, 3H); LRMS calcd for $C_{11}H_{11}N_3$: 185.2; found 185.0 $(M)^+$.

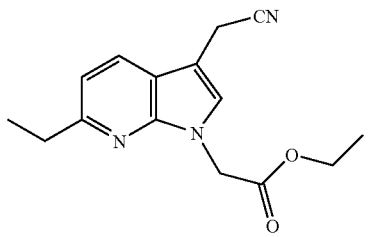

Part 10: 3-Cyanomethyl-6-ethyl-pyrrolo[2,3-b]pyridin-1-yl)-acetic acid ethyl ester A solution of 6-ethyl-1H-pyrrolo[2,3-b]pyridin-3-yl)-acetonitrile (1.5 g, 8.1 mmol) in THF (15 mL) and acetonitrile (15 mL) is cooled to 0° C. and treated with sodium hydride (95%, 0.34 g, 8.1 mmol). After stirring for 1 h, ethyl bromoacetate (1.2 mL, 10.5 mmol) in THF (10 mL) is added and the mixture is warmed to room temperature and stirred for 7 h. The solution is diluted with sat'd aq $NH_4Cl$, the layers are separated and the aqueous layer is extracted with ethyl acetate (3×). The combined organic extracts are concentrated to a thick oil. Purification by flash column chromatography (20-30% ethyl acetate in hexanes) provided 3-cyanomethyl-6-ethyl-pyrrolo[2,3-b]pyridin-1-yl)-acetic acid ethyl ester (1.2 g, 55%) as a yellow solid. mp 52-54° C.; $R_f$ 0.19 (25% ethyl acetate in hexanes) $^1H$ NMR (DMSO-$d_6$, 300 MHz) δ 7.93 (d, J=8.1 Hz, 1 H), 7.44 (s, 1 H); 7.05 (d, J=8.1 Hz, 1 H), 5.06 (s, 2 H), 4.12 (q, J=7.2 Hz, 2 H), 4.06 (s, 2 H), 2.77 (q, J=7.5 Hz, 2 H), 1.21 (t, J=7.5 Hz, 3 H), 1.18 (t, J=7.2 Hz, 3 H); LRMS calcd for $C_{15}H_{17}N_3O_2$: 271.3; found 271.0 $(M)^+$. Anal. Calcd for $C_{15}H_{17}N_3O_2$: C, 66.44; H, 6.32; N, 15.49. Found C, 66.55; H, 6.30; N, 15.51.

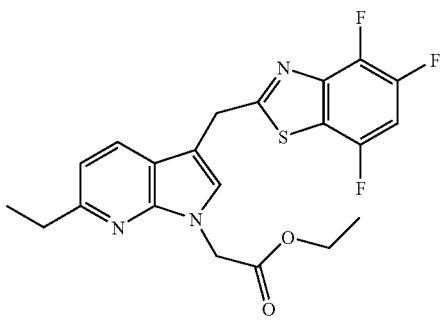

Part 11: [6-Ethyl-3-(4,5,7-trifluoro-benzothiazol-2-ylmethyl)-pyrrolo[2,3-b]pyridin-1-y]-acetic acid ethyl ester A solution of 3-cyanomethyl-6-ethyl-pyrrolo[2,3-b]pyridin-1-yl)-acetic acid ethyl ester (0.50 g, 1.9 mmol), 2-amino-3,4,6-trifluorothiophenol hydrochloride (0.54 g, 2.53 mmol) and BHT (10 mg) in a sealed reaction vessel is heated to 120° C. for 9 h. After cooling to room temperatue, the resulting slurry is adsorbed onto silica gel and purified by flash column chromatography (20-30% ethyl acetate in hexanes) to give [6-ethyl-3-(4,5,7-trifluoro-benzothiazol-2-ylmethyl)-pyrrolo[2,3-b]pyridin-1-yl]-acetic acid ethyl ester (0.7 g, 86%). mp 114-115° C.; $R_f$ 0.24 (25% ethyl acetate in hexanes) $^1$H NMR (DMSO-d$_6$, 300 MHz) δ 7.87 (d, J=7.8 Hz, 1 H), 7.74-7.66 (m, 1 H), 7.54 (s, 1 H), 6.99 (d, J=8.1 Hz, 1 H), 5.08 (s, 2 H), 4.65 (s, 2 H), 4.12 (q, J=7.2 Hz, 2 H), 2.76 (q, J=7.5 Hz, 2 H), 1.23-1.15 (m, 6 H); LRMS calcd for $C_{21}H_{18}F_3N_3O_2S$: 433.1; found 433.0 (M)$^+$. Anal. Calcd for $C_{21}H_{18}F_3N_3O_2S$: C, 58.19; H, 4.19; N, 9.69; S, 7.40. Found C, 58.01; H, 4.13; N, 9.53; S, 7.37.

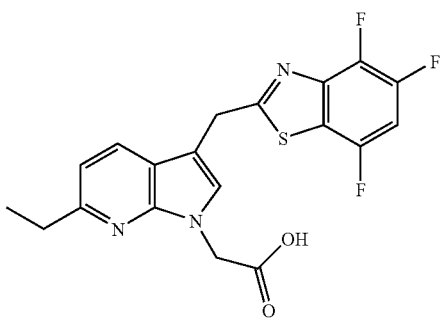

Part 12: [6-Ethyl-3-(4,5,7-trifluoro-benzothiazol-2-ylmethyl)-pyrrolo[2,3-b]pyridin-1-yl]-acetic A solution of [6-ethyl-3-(4,5,7-trifluoro-benzothiazol-2-ylmethyl)-pyrrolo[2,3-b]pyridin-1-yl]-acetic acid ethyl ester (0.474 g, 1.10 mmol) and BHT (2 mg) in 1,2-dimethoxyethane (10 mL, 1 M) is cooled to 0° C. and treated with 1 N NaOH (5 mL, 5 mmol). After stirring 30 min, the soln is acidified to pH 3-4 with 1 N HCl and extracted with ethyl acetate (3×). The combined organic layers are washed with saturated aq NaCl, dried over MgSO4 and filtered through a layered pad of celite, charcoal and florisil to give [6-ethyl-3-(4,5,7-trifluoro-benzothiazol-2-ylmethyl)-pyrrolo[2,3-b]pyridin-1-yl]-acetic acid (0.25 g, 56%). mp 155-157° C.; $R_f$ 0.63 (50% methanol in chloroform) 1H NMR (DMSO-d6, 300 MHz) δ 12.98 (br s, 1 H), 7.87 (d, J=8.1 Hz, 1 H), 7.73-7.64 (m, 1 H), 7.53 (s, 1 H), 6.98 (d, J=8.1 Hz, 1 H), 4.99 (s, 2 H), 4.64 (s, 2 H), 2.76 (q, J=7.8 Hz, 2 H), 1.21 (t, J=7.8 Hz, 3 H); LRMS calcd for $C_{19}H_{14}F_3N_3O_2S$: 405.4; found 405.0 (M)+. Anal. Calcd for $C_{19}H_{14}F_3N_3O_2S$: C, 56.29; H, 3.48; N, 10.37; S, 7.91. Found C, 56.12; H, 3.40; N, 10.27; S, 7.91.

EXAMPLE 2

Preparation of [6-methyl-3-(4,5,7-trifluoro-benzothiazol-2-ylmethyl)-pyrrolo[2,3-b]pyridin-1-yl]-acetic acid

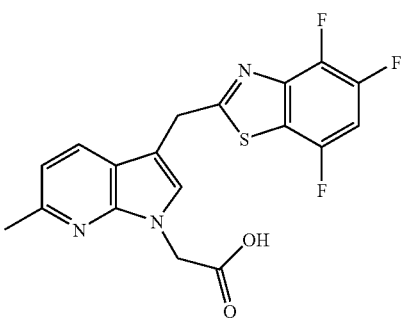

[6-Methyl-3-(4,5,7-trifluoro-benzothiazol-2-ylmethyl)-pyrrolo[2,3-b]pyridin-1-yl]-acetic acid is prepared in a manner analogous to that set forth in Example 1, except 6-methyl-pyridin-2-ylamine is used in place of 6-ethyl-pyridin-2-ylamine in part 5: mp 230° C. (dec); $R_f$ 0.50 (50% methanol in chloroform); $^1$H NMR (DMSO-d6, 300 MHz) δ 13.01 (br s, 1 H), 7.84 (d, J=8.0 Hz, 1 H), 7.83-7.64 (m, 1 H), 7.51 (s, 1 H), 6.96 (d, J=8.0 Hz, 1 H), 4.98 (s, 2 H), 4.63 (s, 2 H), 2.49 (s, 3 H); LRMS calcd for $C_{18}H_{12}F_3N_3O_2S$: 391; found 391 (M)+. Anal. Calcd for $C_{18}H_{12}F_3N_3O_2S$: C, 55.24; H, 3.09; N, 10.74; S, 8.19. Found C, 55.24; H, 3.25; N, 10.58; S, 8.11.

EXAMPLE 3

Preparation of [3-(4,5,7-trifluoro-benzothiazol-2-ylmethyl)-pyrrolo[2,3-b]pyridin-1-yl]-acetic acid

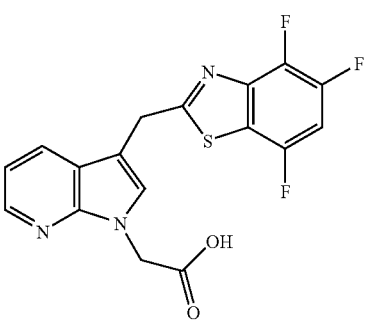

[3-(4,5,7-trifluoro-benzothiazol-2-ylmethyl)-pyrrolo[2,3-b]pyridin-1-yl]-acetic acid is prepared in a manner analogous to that set forth in Example 1 (parts 1-4, 8-12), except 7-azaindole is used in place of 6-ethyl-1H-pyrrolo[2,3-b]pyridine in part 8; 1 H NMR (DMSO-d6, 300 MHz) δ 8.24 (dd, J1=4.7 Hz, J2=1.6 Hz, 1 H), 8.00 (dd, J1=7.8 Hz, J2=1.6

Hz, 1 H), 7.71-7.69 (m, 1 H), 7.64 (s, 1 H), 7.11 (dd, J1=7.8 Hz, J2=4.7 Hz, 1 H), 5.03 (s, 2 H), 4.69 (s, 2 H); LRMS calcd for $C_{17}H_{10}F_3N_3O_2S$: 377; found 378 (M+).

EXAMPLE 4

Preparation of 2,6-Dimethyl-5-(4,5,7-trifluoro-benzothiazole-2-ylmethyl)-pyridin-3-yl-acetic acid hydrochloride

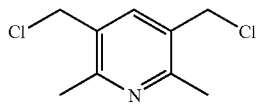

Part 1: 3,5-Bis-chloromethyl-2,6-dimethyl-pyridine:

To a ice-cooled mixture of lithium aluminum hydride (95%) (6.7 g, 168 mmol) in anhydrous diethyl ether (750 mL) is added a solution of 2,6-dimethyl-pyridine-3,5-dicarboxylic acid diethyl ester (31.5 g, 125 mmol) in diethyl ether (250 mL) via cannula under a stream of nitrogen. After the addition is complete, the reaction mixture is warmed to 40° C. for 0.5 h. After cooling to 0° C., water (50 mL) is added slowly under a stream of nitrogen. The resulting solids are filtered, washed with diethyl ether (250 mL), suspended in methanol (700 mL) and warmed to a gentle reflux (1 h). The remaining aluminum salts are filtered hot and washed with hot methanol (200 mL). The filtrate is concentrated and dried in vacuo to afford 5-hydroxymethyl-2,6-dimethyl-pyridin-3-yl-methanol as a white solid and is used in the subsequent step without further purification: $R_f$ 0.16 (10% methanol in chloroform); $^1$H NMR (DMSO-$d_6$, 300 MHz) δ 7.62 (s, 1 H), 4.45 (s, 4 H), 2.34 (s, 6 H); ESI-LCMS m/z calcd for $C_9H_{13}NO_2$: 167.1; found 168.0 (M+1)+.

5-Hydroxymethyl-2,6-dimethyl-pyridin-3-yl-methanol (125 mmol) is treated with thionyl chloride (50 mL, 685 mmol) and stirred at room temperature for 3 h. The excess SOCl$_2$ is removed under reduced pressure. Water (300 mL) is added and the mixture is neutralized with solid Na$_2$CO$_3$. The precipitated product is filtered, washed with H$_2$O (200 mL) and dried in vacuo to provide 3,5-bis-chloromethyl-2,6-dimethyl-pyridine as a white solid (19.9 g, 78%): mp 108-109° C.; $R_f$ 0.46 (50% n-heptane in ethyl acetate); $^1$H NMR (CDCl$_3$, 300 MHz) δ 7.54 (s, 1 H), 4.58 (s, 4 H), 2.61 (s, 6H); ESI-LCMS m/z calcd for $C_9H_{11}Cl_2N$: 203.0; found 204.0 (M+1)+.

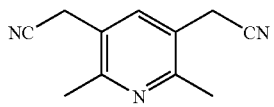

Part 2: 5-Cyanomethyl-2,6-dimethyl-pyridin-3-yl-acetonitrile

A solution of 3,5-bis-chloromethyl-2,6-dimethyl-pyridine (18.0 g, 88.2 mmol) in dimethylformamide (110 mL, 0.8 M) is cooled to 0° C. and treated with a solution of potassium cyanide (12.4 g, 190 mmol) in water (35 mL). The cooling bath is removed, and after 4 h, ice-cooled H$_2$O (600 mL) is added. The resulting solids are filtered, washed with ice-cooled water (100 mL) and recrystallized from H$_2$O to provide 5-cyanomethyl-2,6-dimethyl-pyridin-3-yl-acetonitrile as light brown flakes (10.9 g, 67%): mp 65-67° C.; $R_f$ 0.23 (20% n-heptane in ethyl acetate); $^1$H NMR (CDCl$_3$, 300 MHz) δ 7.61 (s, 1 H), 3.69 (s, 4 H), 2.56 (s, 6 H); ESI-LCMS m/z calcd for $C_{11}H_{11}N_3$: 185.1; found 186.0 (M+1)+. Anal. Calcd for $C_{11}H_{11}N_3$.0.15H$_2$O: C, 70.30; H, 6.06; N, 22.36. Found: C, 70.44; H, 6.01; N, 22.13.

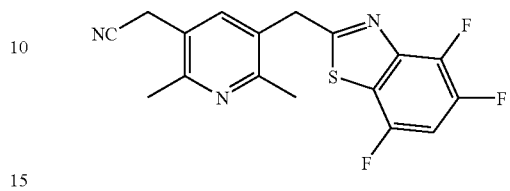

Part 3: 2,6-Dimethyl-5-(4,5,7-trifluorobenzothiazole-2-ylmethyl)-pyridin-3-yl-acetonitrile In a teflon screwcap glass pressure vessel a solution of 5-cyanomethyl-2,6-dimethyl-pyridin-3-yl-acetonitrile (1.5 g, 8.1 mmol), 2-amino-3,4,6-trifluoro-benzenethiol hydrochloride (2.6 g, 12.2 mmol), 2,6-di-tert-butyl-4-methylphenol (BHT) (20 mg) and acetic acid (0.56 mL, 9.8 mmol) in 2,2,2-trifluoroethanol (10 mL, 0.8 M, degassed with nitrogen) is warmed to 90° C. and stirred overnight. The mixture is cooled to room temperature, added to saturated aq sodium bicarbonate (30 mL), extracted with ethyl acetate (2×30 mL) and dried over sodium sulfate. Purification by medium-pressure liquid chromatography (MPLC) on silica (10-90% ethyl acetate in heptane) afford 2,6-dimethyl-5-(4,5,7-trifluorobenzothiazole-2-yl-methyl)-pyridin-3-yl-acetonitrile as a white solid (1.1 g, 38%); $R_f$ 0.37 (20% ethyl acetate in heptane); $^1$H NMR (DMSO-$d_6$, 300 MHz) δ 7.71 (ddd, J=10.3, 8.5, 5.4 Hz, 1H), 7.67 (s, 1 H), 4.61 (s, 2 H), 4.03 (s, 2 H), 2.44 (s, 3 H), 2.43 (s, 3 H). ESI-LCMS m/z calcd for $C_{17}H_{12}F_3N_3S$: 347.1; found 348.0 (M+1)+.

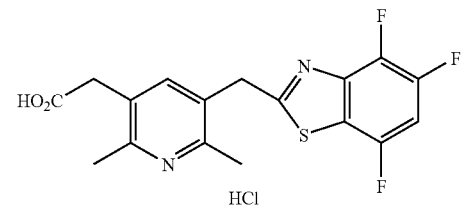

Part 4: 2,6-Dimethyl-5-(4,5,7-trifluoro-benzothiazole-2-yl-methyl)-pyridin-3-yl-acetic acid hydrochloride A solution of 2,6-dimethyl-5-(4,5,7-trifluorobenzothiazole-2-yl-methyl)-pyridin-3-yl-acetonitrile (0.50 g, 1.43 mmol) in 50% hydrochloric acid (HCl) (8 ml, 0.2 M) under nitrogen is warmed (90° C. bath) and stirred overnight. The reaction mixture is added to H$_2$O (20 mL) and brought to pH 5 with NaHCO$_3$. The solids are filtered and the aqueous extracted with ethyl acetate (5×30 mL). The solid and extracts are combined and purified by reverse-phase HPLC (acetonitrile/water, 0.05% HCl)to give 2,6-Dimethyl-5-(4,5, 7-trifluoro-benzothiazole-2-ylmethyl)-pyridin-3-yl-acetic acid as a white solid (0.40 g, 75%): mp 211° C. dec $^1$H NMR (DMSO-$d_6$, 300 MHz) δ 8.29 (s, 1 H), 7.85-7.74 (m, 1 H), 4.80 (s, 2 H), 3.86 (s, 2 H), 2.73 (s, 3 H), 2.67 (s, 3 H). ESI-LCMS m/z calcd for $C_{17}H_{13}F_3N_2O_2S$: 366.1; found 367.0 (M+1)+. Anal. Calcd for $C_{17}H_{14}ClF_3N_2O_2S$: C, 50.69; H, 3.50; N, 6.95; Cl, 8.80; S, 7.96. Found: C, 50.48; H, 3.63; N, 6.89; Cl, 8.97; S, 7.84.

EXAMPLE 5

Preparation of [2,6-Diethyl-5-(4,5,7-trifluoro-benzothiazol-2-ylmethyl)-pyridin-3-yl]acetic acid hydrochloride

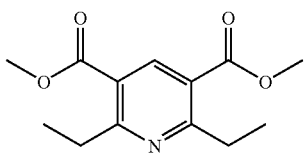

Part 1: 2,6-Diethyl-pyridine-3,5-dicarboxylic acid dimethyl Ester

A mixture of methyl-3-oxo-pentanoate (3.15 g, 24.2 mmol), methyl-3-amino-pentenoate (3.15 g, 24.3 mmol) and 4-antipyrinecarboxaldehyde (5.00 g, 23.1 mmol) in 2,2,2-trifluroethanol (4 mL) in a teflon screwcap glass pressure vessel is heated to 100° C. with stirring overnight. After cooling to room temperature, the contents of the vessel are transferred to a flask containing methanol (10 mL) and concentrated hydrochloric acid (4.0 mL, 48 mmoL), and the mixture is stirred at 90° C. for 6 h. The contents are poured into 50% aq NaHCO3 (100 mL), extracted with ethyl acetate (2×50 mL) and dried over $Na_2SO_4$. The crude material is purified by medium-pressure liquid chromatography (MPLC) on silica (5-50% ethyl acetate in heptane) to afford the product as a white solid (2.1 g, 36%); $R_f$ 0.55 (30% ethyl acetate in heptane); $^1$H NMR (CDCl$_3$, 300 MHz) δ 8.64 (s, 1 H), 3.93 (s, 6 H), 3.20 (q, J=7.5 Hz, 4 H), 1.31 (t, J=7.5 Hz, 6 H); ESI-LCMS m/z calcd for $C_{13}H_{17}NO_4$: 251.1; found 252.0 (M+1)+.

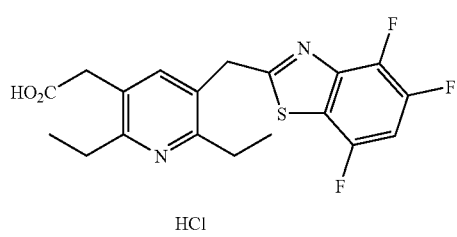

Part 2: [2,6-Diethyl-5-(4,5,7-trifluoro-benzothiazol-2-ylmethyl)-pyridin-3-yl]acetic acid hydrochloride 2,6-Diethyl-5-(4,5,7-trifluoro-benzothiazol-2-ylmethyl)-pyridin-3-yl]acetic acid hydrochloride is prepared in a manner analogous to that set forth in Example 4, except 2,6-diethyl-pyridine-3,5-dicarboxylic acid dimethyl ester is used instead of 2,6-dimethyl-pyridine-3,5-dicarboxylic acid dimethyl ester in part 1: mp 143-145° C.; $R_f$ 0.05 (10% methanol in chloroform); $^1$H NMR (DMSO-d$_6$, 300 MHz) δ 7.76-7.73 (m, 1 H), 7.71 (s, 1 H), 4.55 (s, 2 H), 3.55 (s, 2 H), 2.76 (m, 4 H), 1.20-1.11 (m, 6 H); ESI-LC/MS m/z calcd for $C_{19}H_{17}F_3N_2O_2S$: 394.4; found 395.0 (M+1)+. Anal. Calcd for $C_{19}H_{17}F_3N_2O_2S$·HCl: C, 52.96; H, 4.21; N, 6.50. Found C, 53.44; H, 4.12; N, 6.43.

EXAMPLE 6

Preparation of [2,6-Diphenyl-5-(4,5,7-trifluoro-benzothiazol-2-ylmethyl)-pyridin-3-yl]acetic acid hydrochloride

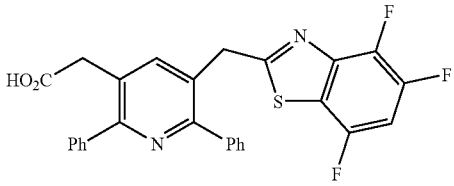

2,6-Diphenyl-5-(4,5,7-trifluoro-benzothiazol-2-ylmethyl)-pyridin-3-yl]acetic acid is prepared in a manner analogous to that set forth in Example 4, except 2,6-diphenyl-pyridine-3,5-dicarboxylic acid dimethyl ester is used instead of 2,6-dimethyl-pyridine-3,5-dicarboxylic acid dimethyl ester in part 1: mp 84-86° C.; $R_f$ 0.25 (10% methanol in chloroform); $^1$H NMR (DMSO-d$_6$, 300 MHz) δ 7.91 (s, 1 H), 7.76-7.69 (m, 1 H), 7.56-7.51 (m, 4 H), 7.46-7.38 (m, 6 H), 4.65 (s, 2 H), 3.68 (s, 2 H); ESI-LC/MS m/z calcd for $C_{27}H_{17}F_3N_2O_2S$: 490.5; found 491.0 (M+1)+.

EXAMPLE 7

Preparation of [2,6-Dipropyl-5-(4,5,7-trifluoro-benzothiazol-2-ylmethyl)-pyridin-3-yl]acetic acid hydrochloride

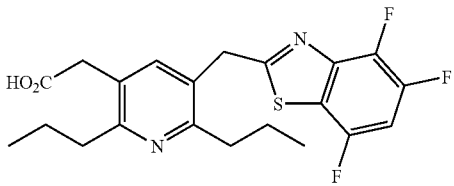

2,6-Dipropyl-5-(4,5,7-trifluoro-benzothiazol-2-ylmethyl)-pyridin-3-yl]acetic acid is prepared in a manner analogous to that set forth in Example 4, except 2,6-dipropyl-pyridine-3,5-dicarboxylic acid dimethyl ester is used instead of 2,6-dimethyl-pyridine-3,5-dicarboxylic acid dimethyl ester in part 1: mp 98-100° C.; $R_f$ 0.50 (10% methanol in chloroform); $^1$H NMR (DMSO-d$_6$, 300 MHz) δ 7.76-7.68 (m, 1 H), 7.46 (s, 1 H), 4.51 (s, 2 H), 3.45 (s, 2 H), 2.68-2.60 (m, 4 H), 1.67-154 (m, 4 H), 0.89-0.80 (m, 6H); ESI-LC/MS m/z calcd for $C_{27}H_{17}F_3N_2O_2S$: 422.5; found 423.0 (M+1)+.

EXAMPLE 8

Preparation of 5-(4,5,7-trifluoro-benzothiazol-2-ylmethyl)-pyridin-3-yl-acetic acid hydrochloride

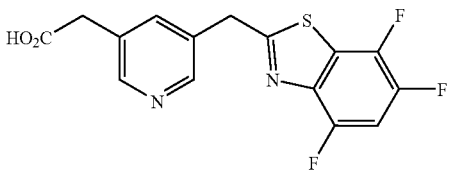

5-(4,5,7-Trifluoro-benzothiazol-2-ylmethyl)-pyridin-3-yl-acetic acid is prepared in a manner analogous to that set forth in example 4, except pyridine-3,5-dicarboxylic acid dimethyl ester is used instead of 2,6-dimethyl-pyridine-3,5-dicarboxylic acid dimethyl ester in part 1. mp 196-197° C.; $R_f$ 0.31 (25% methanol in dichloromethane; $^1$H NMR (DMSO-$d_6$, 300 MHz) δ 8.54 (d, J=2.1 Hz, 1 H), 8.41 (d, J=2.1 Hz, 1 H), 7.80-7.69 (m, 2 H), 4.62 (s, 2 H), 3.65 (s, 2 H); ESI-LCMS m/z calcd for $C_{15}H_9F_3N_2O_2S$: 338.0; found 339.0 (M+1)$^+$. Anal. Calcd for $C_{15}H_9F_3N_2O_2S.0.3H_2O$: C, 52.42; H, 2.82; N, 8.15, S, 9.33. Found C, 52.30; H, 2.62; N, 8.10; S, 9.32.

EXAMPLE 9

Preparation of 2,4,6-trimethyl-5-(4,5,7-trifluoro-benzothiazol-2-ylmethyl)-pyridin-3-yl-acetic acid hydrochloride

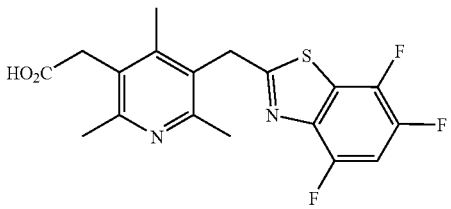

2,4,6-Trimethyl-5-(4,5,7-trifluoro-benzothiazol-2-ylmethyl)-pyridin-3-yl-acetic acid hydrochloride is prepared in a manner analogous to that set forth in example 4, except 2,4,6-trimethyl-pyridine-3,5-dicarboxylic acid dimethyl ester is used instead of 2,6-dimethyl-pyridine-3,5-dicarboxylic acid dimethyl ester in part 1: mp 216-217° C.; $R_f$ 0.08 (10% methanol in dichloromethane); $^1$H NMR (DMSO-$d_6$, 300 MHz) δ 7.78 (ddd, $J_1$=11.2, $J_2$=9.4, $J_3$=5.8 Hz, 1 H), 4.84 (s, 2 H), 3.89 (s, 2 H), 2.76 (s, 3 H), 2.70 (s, 3 H), 2.44 (s, 3 H), ESI-LCMS m/z calcd for $C_{18}H_{15}F_3N_2O_2S$: 380.1; found 381.0 (M+1)$^+$. Anal. Calcd for $C_{18}H_{15}F_3N_2O_2S.0.8HCl$: C, 52.79; H, 3.89; N, 6.84, S, 7.83. Found C; 52.50; H; 3.86; N, 6.78; S, 7.92.

EXAMPLE 10

Preparation of 2,6-dimethyl-4-ethyl-5-(4,5,7-trifluoro-benzothiazol-2-ylmethyl)-pyridin-3-yl-acetic acid hydrochloride

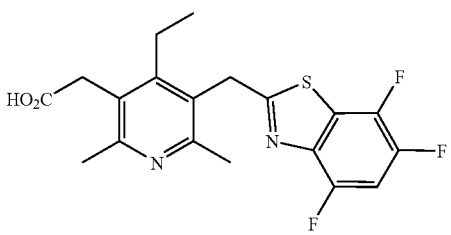

2,6-dimethyl-4-ethyl-5-(4,5,7-trifluoro-benzothiazol-2-ylmethyl)-pyridin-3-yl-acetic acid is prepared in a manner analogous to that set forth in example 4, except 2,6-dimethyl-4-ethyl-pyridine-3,5-dicarboxylic acid dimethyl ester is used instead of 2,6-dimethyl-pyridine-3,5-dicarboxylic acid dimethyl ester in part 1: mp 193-195° C.; $R_f$ 0.09 (10% methanol in dichloromethane); $^1$H NMR (DMSO-$d_6$, 300 MHz) δ 7.74 (ddd, $J_1$=11.7, $J_2$=9.2, $J_3$=5.7 Hz, 1 H), 4.63 (s, 2 H), 3.71 (s, 2 H), 2.76 (q, J=7.6 Hz, 2 H), 2.53 (s, 3 H), 2.44 (s, 3 H), 0.99 (t, J=7.4 Hz, 3 H); ESI-LCMS m/z calcd for $C_{19}H_{17}F_3N_2O_2S$: 394.1; found 395.0 (M+1)$^+$. Anal. Calcd for $C_{19}H_{17}F_3N_2O_2S.0.5H_2O$: C, 56.57; H, 4.50; N, 6.94; S, 7.95. Found C, 56.68; H, 4.39; N, 6.89; S, 8.04.

EXAMPLE 11

Preparation of 2-ethyl-5-(4,5,7-trifluoro-benzothiazol-2-ylmethyl)-pyridin-3-yl-acetic acid hydrochloride

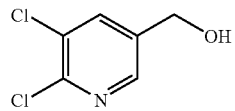

Part 1: 5,6-dichloro-pyridin-3-yl-methanol

A slurry of 5,6-dichloronicotinic acid (25.3 g, 132 mmol) in THF (30 mL, 4.4 M) is cooled to 0° C. and carefully treated with 2 M borane dimethyl sulfide/THF (100 mL, 200 mmol) via syringe under a stream of nitrogen. After 1 h, the cooling bath is removed. After stirring overnight the colution is re-cooled to 0° C. and carefully quenched with water (20 mL). The reaction volume is reduced in vacuo, 50% NaHCO$_3$ (150 mL) is added and the mixture is extracted with ethyl acetate (2×150 mL). The organic layer is washed with saturated aq NaCl (100 mL) and dried over Na$_2$SO$_4$. The product is purified by MPLC (30-90% ethyl acetate in n-heptane) to provide 5,6-dichloro-pyridin-3-yl-methanol as a white solid (19.1 g, 81%): $R_f$ 0.57 (25% ethyl acetate in n-heptane), $^1$H NMR (CDCl$_3$, 300 MHz) δ 8.27 (d, J=2.3 Hz, 1 H), 7.84 (d, J=2.3 Hz, 1 H), 4.74 (s, 2 H); ESI-LCMS m/z calcd for $C_6H_5Cl_2NO$: 177.0; found 178.0 (M+1)$^+$.

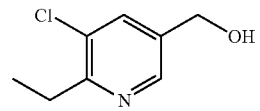

Part 2: 5-chloro-6-ethyl-pyridin-3-yl-methanol

To solution of 5,6-dichloronicotinic acid (21.46 g, 112 mmol) and 1,2-bis(diphenylphosphino)ethane dichloronickel(II) ((Ni(dppe)Cl$_2$) (2.00 g, 3.6 mmol) in THF (60 mL, 1.9 M) is cooled to 0° C. and treated with ethyl magnesium chloride (2.8 M, 107 mL, 300 mmol) slowly via syringe with stirring under nitrogen. The reaction mixture is warmed to 55° C. for 3 h, cooled to 0° C. and acidified to pH 5 with 2 M HCl (100 mL). After concentrating in vacuo, the solution is reconstituted and extracted with ethyl acetate (2×200 mL), dried over Na$_2$SO$_4$, filtered and concentrated. The solvent removed in vacuo to provide crude 5-chloro-6-ethyl-nicotinic acid as a light brown glass (ESI-LCMS m/z calcd for $C_8H_8ClNO_2$: 185.0; found 186.0 (M+1)$^+$, which is used without further purification.

The crude product in diethyl ether (250 mL) is added to an ice-cooled mixture of lithium aluminum hydride (95%, 6.7 g, 168 mmol) in anhydrous diethyl ether (750 mL) via cannula under a stream of nitrogen. After the addition is complete, the reaction mixture is warmed to 40° C. for 0.5 h then cooled to 0° C. Water is added slowly and the resulting solids are filtered, washed with diethyl ether (250 mL), suspended in methanol (700 mL) and warmed to a gentle reflux (1 h). The remaining aluminum salts are filtered hot and washed with hot methanol (200 mL). The resulting product is purified by MPLC (10-30% ethyl acetate in n-heptane to provide 5-chloro-6-ethyl-pyridin-3-yl-methanol as a yellow oil (3.26 g, 17%): $R_f$ 0.21 (30% ethyl acetate in n-heptane, $^1$H NMR (CDCl$_3$, 300 MHz) δ 8.38 (s, 1 H), 7.69 (s, 1 H), 4.70 (s, 2 H), 2.96 (q, J=7.4 Hz, 2 H), 1.29 (t, J=7.4 Hz, 3 H). ESI-LCMS m/z calcd for $C_8H_{10}ClNO$: 171.0; found 172.0 (M+1)$^+$.

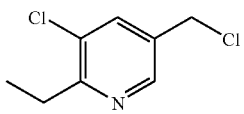

Part 3: 3-chloro-5-chloromethyl-2-ethyl-pyridine

5-Chloro-6-ethyl-pyridin-3-yl-methanol (4.00 g, 23.3 mmol) is treated with thionyl chloride (50 mL, 685 mmol) and stirred at room temperature for 3 h. The excess SOCl$_2$ is removed under reduced pressure. Water (300 mL) is added and the mixture is neutralized with solid Na$_2$CO$_3$. The precipitated product is filtered, washed with H$_2$O (200 mL) and dried in vacuo to provide 3-chloro-5-chloromethyl-2-ethyl-pyridine as a light brown oil (4.3 g, 97%): $R_f$ 0.54 (30% ethyl acetate in n-heptane), $^1$H NMR (CDCl$_3$, 300 MHz) δ 8.42 (d, J=1.9 Hz 1 H), 7.70 (d, J=1.9 Hz, 1 H), 4.55 (s, 2 H), 2.97 (q, J=7.4 Hz, 2 H), 1.30 (t, J=7.4 Hz, 3 H). ESI-LCMS m/z calcd for $C_8H_9Cl_2N$: 189.0; found 190.0 (M+1)$^+$.

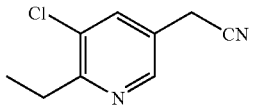

Part 4: 5-Chloro-6-ethyl-pyridin-3-yl-acetonitrile

A solution of 3-chloro-5-chloromethyl-2-ethyl-pyridine (4.03 g, 21 mmol) in dimethylformamide (26 mL, 0.8 M) is cooled to 0° C. and treated with a solution of potassium cyanide (1.48 g, 22.7 mmol) in water (10 mL). After 4 h, the solution is diluted with 50% aq NaCl and extracted with ethyl acetate. The organic extracts are washed with sat'd aq lithium chloride and purified by MPLC (30-90% ethyl acetate in heptane) to give 5-chloro-6-ethyl-pyridin-3-yl-acetonitrile as a light brown oil (3.42 g, 90%): Rf 0.29 (30% ethyl acetate in n-heptane), $^1$H NMR (CDCl$_3$, 300 MHz) δ 8.38 (br s, 1 H), 7.67 (br s, 1 H), 3.74 (s, 2 H), 2.97 (q, J=7.5 Hz, 2 H), 1.30 (t, J=7.5 Hz, 3 H) ESI-LCMS m/z calcd for $C_9H_9ClN_2$: 180.0; found 181.0 (M+1)$^+$.

Part 5: 5-allyl-6-ethyl-pyridin-3-yl-acetonitrile

A solution of 5-chloro-6-ethyl-pyridin-3-yl-acetonitrile (3.00 g, 16.6 mmol) and allyl-tri-n-butyltin (5.4 mL, 17.4 mmol) in acetonitrile (30 mL, 0.5 M) and dimethylsulfoxide (2 mL), is degassed and treated with 1,1'-bis(diphenylphosphino)ferrocene-dicloronickel(II) (Ni(dppf)Cl$_2$) (0.38 g, 0.55 mmol). The mixture is warmed to 85° C. for 2 h. After cooling to room temperature the solution is diluted with 10% aq potassium fluoride (30 mL) and ethyl acetate (30 mL). The solids are filtered and rinsed with ethyl acetate (30 mL). The organic layer is washed with saturated aq NaCl (80 mL) and dried over Na$_2$SO$_4$. The product is purified by MPLC (25-90% ethyl acetate in n-heptane) to provide 5-allyl-6-ethyl-pyridin-3-yl-acetonitrile as a yellow oil (2.43 g, 79%): $R_f$ 0.28 (50% ethyl acetate in n-heptane), $^1$H NMR (CDCl$_3$, 300 MHz) δ 8.36 (s, 1 H), 7.44 (s, 1 H), 6.00-5.84 (m, 1 H), 5.15 (d, J=10.3 Hz, 1 H), 5.03 (d, J=17.2 Hz, 1 H), 3.71 (s, 2 H), 3.42 (d, J=6.0 Hz, 2 H), 2.83 (q, J=7.6 Hz, 2 H), 1.28 (t, J=7.6 Hz, 3 H). ESI-LCMS m/z calcd for $C_{12}H_{14}N_2$: 186.1; found 187.0 (M+1)$^+$.

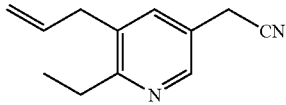

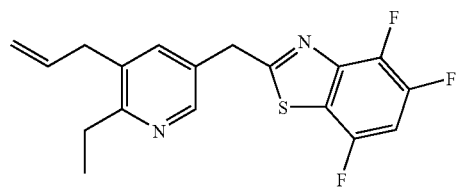

Part 6: 2-(5-allyl-6-ethyl-pyridin-3-ylmethyl)-4,5,7-trifluoro-benzothiazole

In a teflon screwcap glass pressure vessel a solution of 5-allyl-6-ethyl-pyridin-3-yl-acetonitrile (0.70 g, 3.76 mmol), 2-amino-3,4,6-trifluoro-benzenethiol hydrochloride (1.2 g, 5.64 mmol), 2,6-di-tert-butyl-4-methylphenol (BHT) (20 mg) and acetic acid (0.25 mL, 4.51 mmol) in 2,2,2-trifluoroethanol (5 mL, 0.8 M, degassed with nitrogen) is warmed to 90° C. and stirred overnight. The mixture is cooled to room temperature, added to saturated aq sodium bicarbonate (15 mL), extracted with ethyl acetate (2×15 mL) and dried over sodium sulfate. Purification by medium-pressure liquid chromatography (MPLC) on silica (20-40% ethyl acetate in heptane) provided 2-(5-allyl-6-ethyl-pyridin-3-ylmethyl)-4,5,7-trifluoro-benzothiazole as a yellow oil (1.14 g, 87%): $R_f$ 0.38 (30% ethyl acetate in n-heptane), $^1$H NMR (CDCl$_3$, 300 MHz) δ 8.45 (d, J=2.1 Hz, 1 H), 7.44 (d, J=2.1 Hz, 1 H), 7.01 (ddd, J$_1$=10.5 Hz, J$_2$=8.7 Hz, J$_3$=5.6 Hz, 1 H), 5.91 (ddt, J$_1$=17.0 Hz, J$_2$=10.3 Hz, J$_3$=6.3 Hz, 1 H), 5.13 (dd, J$_1$=10.3 Hz, J$_2$=1.5 Hz, 1 H), 5.01 (dd, J$_1$=17.0 Hz, J$_2$=1.5 Hz, 1 H), 3.40 (d, J=6.3 Hz, 2 H), 2.83 (q, J=7.5 Hz, 2 H), 1.29 (t, J=7.5 Hz, 3 H); ESI-LCMS m/z calcd for $C_{18}H_{15}F_3N_2S$: 348.1; found 349.0 (M+1)$^+$.

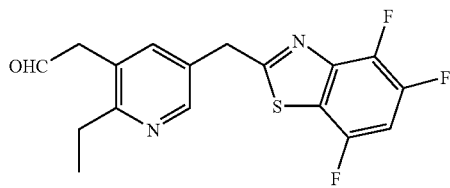

Part 7: 2-ethyl-5-(4,5,7-trifluoro-benzothiazol-2-ylmethyl)-pyridin-3-yl)-acetaldehyde A solution of 2-(5-allyl-6-ethyl-pyridin-3-ylmethyl)-4,5,7-trifluoro-benzothiazole (0.50 g, 1.44 mmol) in 50% methanol in dichloromethane (5 mL, 0.2 M) is cooled to −78° C. and treated with ozone. After the solution became blue (30 min), it is purged with nitrogen and treated with dimethyl sulfide (0.14 mL, 1.9 mmol). After stirring overnight the solvent is removed in vacuo and the product is purified by flash chromatography (50% ethyl acetate in n-heptane) to provide 2-ethyl-5-(4,5,7-trifluoro-benzothiazol-2-ylmethyl)-pyridin-3-yl)-acetaldehyde as a yellow oil (0.43 g, 87%): $R_f$ 0.27 (30% ethyl acetate in n-heptane), $^1$H NMR (CDCl$_3$, 300 MHz) δ 9.77 (s, 1 H), 8.55 (s, 1 H), 7.48 (s, 1 H), 7.08-6.97 (m, 1 H), 4.45 (s, 2 H), 3.77 (s, 2 H), 2.78 (q, J=7.5 Hz, 2 H), 1.28 (t, J=7.5 Hz, 3H); ESI-LCMS m/z calcd for $C_{17}H_{13}F_3N_2OS\cdot CH_3OH$: 382.1; found 383.0 (M+1)$^+$.

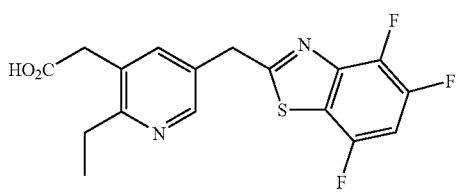

Part 8: 2-Ethyl-5-(4,5,7-trifluoro-benzothiazol-2-ylmethyl)-pyridin-3-yl-acetic acid hydrochloride A solution of 2-ethyl-5-(4,5,7-trifluoro-benzothiazol-2-ylmethyl)-pyridin-3-yl)-acetaldehyde (0.35 g, 1.0 mmol) in acetonitrile and ethyl acetate (1:1, 9 mL, 0.1 M) is cooled to 0° C., and treated with sodium periodate (0.44 g, 2.06 mmol) in H$_2$O (6 mL) and ruthenium(III) chloride hydrate (12 mg, 0.04 mmol). The cooling bath is removed and after 1 h. Water (20 mL) is added and the brown mixture is extracted with ethyl acetate (3×20 mL) and dried over Na$_2$SO$_4$. The product is purified by flash chromatography (5-10% methanol in dichloromethane) to provide 2-ethyl-5-(4,5,7-trifluoro-benzothiazol-2-ylmethyl)-pyridin-3-yl-acetic acid hydrochloride as a yellow glass (0.17 g, 42%): $R_f$ 0.19 (10% methanol in dichloromethane), $^1$H NMR (DMSO-d$_6$, 300 MHz) δ 8.78 (s, 1 H), 8.27 (s, 1 H), 7.79 (ddd, J$_1$=11.1 Hz, J$_2$=9.3 Hz, J$_3$=5.7 Hz, 1 H), 4.77 (s, 2 H), 3.88 (s, 2 H), 2.93 (q, J=7.5 Hz, 2 H), 1.24 (t, J=7.5 Hz, 3 H); ESI-LCMS m/z calcd for $C_{17}H_{13}F_3N_2O_2S$: 366.1; found 367.0 (M+1)$^+$. Anal. Calcd for $C_{17}H_{13}F_3N_2O_2S\cdot HCl$: C, 50.69; H, 3.50; N, 6.95; S, 7.96. Found: C, 50.45; H, 3.53; N, 7.18; S, 7.72.

EXAMPLE 12

Preparation of 2-benzyl-5-(4,5,7-trifluoro-benzothiazol-2-ylmethyl)-pyridin-3-yl-acetic acid hydrochloride

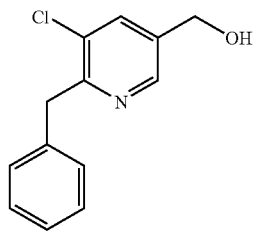

Part 1: 6-benzyl-5-chloro-pyridin-3-yl-methanol

A solution of 5,6-dichloro-pyridin-3-yl-methanol (5.0 g, 28.1 mmol) and tetrabenzyltin (14.0 g, 29 mmol) in DMF (40 mL, 0.7 M) is degassed under nitrogen and treated with PdP(Ph$_3$)$_4$ (1.3 g, 1.2 mmol). The solution is warmed to 125° C. for 48 h, cooled to room temperature and treated with 50% aq KF (100 mL) and stirred for 40 min. Water (50 mL) is added and the solids are filtered and washed with ethyl acetate (150 mL). The organic phase is washed with H$_2$O (100 mL), saturated aq LiCl (50 mL) and dried over Na$_2$SO$_4$. The product is purified by MPLC (30-90% ethyl acetate in n-heptane) to provide 6-benzyl-5-chloro-pyridin-3-yl-methanol as a white solid (4.25 g, 64%): $R_f$ 0.27 (30% ethyl acetate in n-heptane), $^1$H NMR (CDCl$_3$, 300 MHz) δ 8.42 (s, 1 H), 7.71 (s, 1 H), 7.42-7.16 (m, 5 H), 4.69 (s, 2 H), 4.31 (s, 2 H); ESI-LCMS m/z calcd for $C_{13}H_{12}ClNO$: 233.1; found 234.0 (M+1)$^+$.

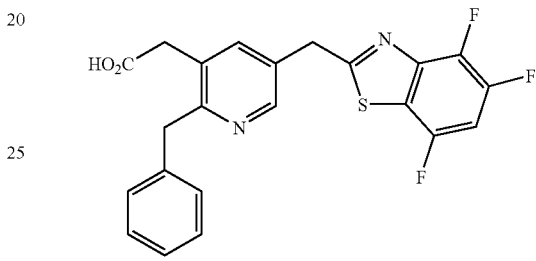

Part 2: 2-benzyl-5-(4,5,7-trifluoro-benzothiazol-2-ylmethyl)-pyridin-3-yl-acetic acid hydrochloride 2-Benzyl-5-(4,5,7-trifluoro-benzothiazol-2-ylmethyl)-pyridin-3-yl-acetic acid hydrochloride is prepared in a manner analogous to that set forth in example 11, except 6-benzyl-5-chloro-pyridin-3-yl-methanol is used instead of 6-ethyl-5-chloro-pyridin-3-yl-methanol in part 2: mp 175° C. dec; $R_f$ 0.30 (10% methanol in dichloromethane), $^1$H NMR (DMSO-d$_6$, 300 MHz) δ 8.74 (s, 1 H), 8.11 (s, 1 H), 7.78 (ddd, J$_1$=11.1 Hz, J$_2$=9.2 Hz, J$_3$=5.8 Hz, 1 H), 7.32-7.14 (m, 5 H), 4.73 (s, 2 H), 4.29 (s, 2 H), 3.75 (s, 2 H); ESI-LCMS m/z calcd for $C_{22}H_{15}F_3N_2O_2S$: 428.1; found 429.0 (M+1)$^+$. Anal. Calcd for: $C_{22}H_{15}F_3N_2O_2S\cdot HCl\cdot 0.2H_2O$: C, 56.40; H, 3.53; N, 5.98; S, 6.84. Found: C, 56.32; H, 3.64; N, 5.99; S, 6.88.

EXAMPLE 13

Preparation of 2-phenyl-5-(4,5,7-trifluoro-benzothiazol-2-ylmethyl)-pyridin-3-yl-acetic acid hydrochloride

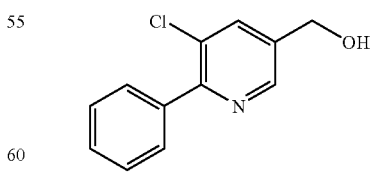

Part 1: 5-chloro-6-phenyl-pyridin-3-yl-methanol

A solution of 5,6-dichloro-pyridin-3-yl-methanol (10.0 g, 56.2 mmol), phenylboronic acid (7.5 g, 61.5 mmol), K$_2$CO$_3$ (20.0 g, 145 mmol) in H$_2$O (140 mL) and dimethoxyethane (140 mL, 0.4 M), is degassed and treated with tetrakis (triphenylphosphine)palladium(0) (1.4 g, 1.2 mmol) and warmed to a gentle reflux under nitrogen for 4 h. After cooling to room temperature, ethyl acetate (100 mL) is added and the solids are filtered and washed with ethyl acetate (20 ml). The filtrate is extracted with ethyl acetate (100 mL) and the organic layer is washed with $H_2O$ (200 mL), saturated aq NaCl (200 mL) and dried over $Na_2SO_4$. The product is purified by MPLC (30-90% ethyl acetate in n-heptane) to provide 5-chloro-6-phenyl-pyridin-3-yl-methanol as a light yellow solid (12.0 g, 97%): $R_f$ 0.24 (30% ethyl acetate in n-heptane), $^1$H NMR (CDCl$_3$, 300 MHz) δ 8.47 (br s, 1 H), 7.78 (br s, 1 H), 7.70-7.65 (m, 2 H), 7.50-7.40 (m, 3 H), 4.67 (s, 2 H); ESI-LCMS m/z calcd for $C_{12}H_{10}ClNO$: 219.0; found 220.0 (M+1)$^+$.

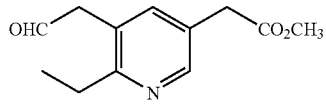

Part 2: 2-Phenyl-5-(4,5,7-trifluoro-benzothiazol-2-ylmethyl)-pyridin-3-yl-acetic acid hydrochloride 2-Phenyl-5-(4,5,7-trifluoro-benzothiazol-2-ylmethyl)-pyridin-3-yl-acetic acid hydrochloride is prepared in a manner analogous to that set forth in example 11, except 6-phenyl-5-chloro-pyridin-3-yl-methanol is used instead of 6-ethyl-5-chloro-pyridin-3-yl-methanol in part 2: mp 110° C. dec; $R_f$ 0.34 (10% methanol in dichloromethane), $^1$H NMR (DMSO-d$_6$, 300 MHz) δ 8.82 (s, 1 H), 8.23 (s, 1 H), 7.84-7.74 (m, 1 H), 7.53 (br s, 5 H), 4.80 (s, 2 H), 3.72 (s, 2 H); ESI-LCMS m/z calcd for $C_{21}H_{13}F_3N_2O_2S$: 414.1; found 415.0 (M+1)$^+$. Anal. Calcd for $C_{21}H_{13}F_3N_2O_2S\cdot HCl\cdot 0.3H_2O\cdot 0.2CH_3CN$: C, 55.34; H, 3.30; N, 6.63; S, 6.90. Found: C, 55.10; H, 3.27; N, 6.71; S, 6.81.

EXAMPLE 14

Preparation of 6-ethyl-5-(4,5,7-trifluoro-benzothiazol-2-ylmethyl)-pyridin-3-yl-acetic acid hydrochloride

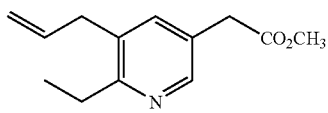

Part 1: 5-Allyl-6-ethyl-pyridin-3-yl-acetic acid methyl ester

A solution of 5-allyl-6-ethyl-pyridin-3-yl-acetonitrile (1.30 g, 6.98 mmol) and 4.0 M HCl/dioxane (6.9 mL, 28 mmol) in anhydrous methanol (16 mL, 0.4 M) is warmed to a gentle reflux and stirred overnight under nitrogen. After cooling, the mixture is added to saturated aq NaHCO$_3$ (30 mL), extracted with ethyl acetate (2×30 mL) and dried over Na$_2$SO$_4$. The product is purified by MPLC (25-90% ethyl acetate in n-heptane) to provide 5-allyl-6-ethyl-pyridin-3-yl-acetic acid methyl ester as a clear oil (1.21 g, 79%): $R_f$ 0.39 (50% ethyl acetate in n-heptane), $^1$H NMR (CDCl$_3$, 300 MHz) δ 8.32 (d, J=2.2 Hz, 1 H), 7.38 (d, J=2.2 Hz, 1 H), 5.93 (ddt, J$_1$=16.8 Hz, J$_2$=10.2 Hz, J$_3$=6.2 Hz, 1 H), 5.12 (dd, J$_1$=10.2 Hz, J$_2$=1.6 Hz, 1H), 5.02 (dd, J$_1$=16.8 Hz, J$_2$=1.6 Hz, 1H), 3.70 (s, 3 H), 3.40 (d, J=6.2 Hz, 2 H), 2.81 (q, J=7.5 Hz, 2 H), 1.28 (t, J=7.5 Hz, 3 H). ESI-LCMS m/z calcd for $C_{13}H_{17}NO_2$: 219.1; found 220.0 (M+1)$^+$.

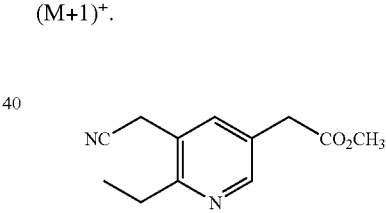

Part 2: 6-ethyl-5-(2-oxo-ethyl)-pyridin-3-yl-acetic acid methyl ester

A solution of 5-allyl-6-ethyl-pyridin-3-yl-acetic acid methyl ester (1.00 g, 4.56 mmol) in 50% methanol in dichloromethane solution (25 mL, 0.2 M) is cooled to −78° C. and treated with ozone. After the solution became blue (30 min), it is purged with nitrogen and treated with dimethyl sulfide (1.7 mL, 23 mmol). After stirring overnight the solvent is removed in vacuo and the product is purified by flash chromatography (50% ethyl acetate in n-heptane) to provide 6-ethyl-5-(2-oxo-ethyl)-pyridin-3-yl-acetic acid methyl ester as a clear oil (0.78 g, 78%): $R_f$ 0.26 (50% ethyl acetate in n-heptane), $^1$H NMR (CDCl$_3$, 300 MHz) δ 9.77 (s, 1 H), 8.41 (s, 1 H), 7.43 (s, 1 H), 3.76 (s, 2 H), 3.72 (s, 3 H), 3.62 (s, 2 H), 2.77 (q, J=7.5 Hz, 2H), 1.27 (t, J=7.5 Hz, 3H). ESI-LCMS m/z calcd for $C_{12}H_{15}NO_3$: 221.1; found 222.0 (M+1)$^+$.

Part 3: 5-Cyanomethyl-6-ethyl-pyridin-3-yl-acetic acid methyl ester

A solution of 6-ethyl-5-(2-oxo-ethyl)-pyridin-3-yl-acetic acid methyl ester (0.77 g, 3.46 mmol), hydroxylamine hydrochloride (0.26 g, 3.80 mmol) and triethylamine (0.53 mL, 3.80 mmol) in acetonitrile (9 mL, 0.4 M) is stirred under nitrogen at room temperature for 2 h. Phthalic anhydride (0.55 g, 3.71 mmol) is added and the mixture is warmed to 90° C. for 16 h. After cooling to room temperature, water (50 mL) is added and the mixture is extracted with ethyl acetate (50 mL). The organic layer is washed with saturated NaHCO$_3$ (50 mL) and dried over Na$_2$SO$_4$. The product is purified by flash chromatography (20-50% ethyl acetate in n-heptane) to provide 5-cyanomethyl-6-ethyl-pyridin-3-yl-acetic acid methyl ester as a clear oil (0.60 g, 80%): $R_f$ 0.31 (50% ethyl acetate in n-heptane), $^1$H NMR (CDCl$_3$, 300 MHz) δ 8.44 (s, 1 H), 7.67 (s, 1 H), 3.74 (s, 2 H), 3.73 (s, 3 H), 3.65 (s, 2 H), 2.83 (q, J=7.5 Hz, 2 H), 1.33 (t, J=7.5 Hz, 3 H). ESI-LCMS m/z calcd for $C_{12}H_{14}N_2O_2$: 218.1; found 219.0 (M+1)$^+$.

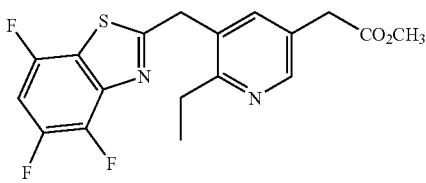

Part 4: 6-Ethyl-5-(4,5,7-trifluoro-benzothiazol-2-ylmethyl)-pyridin-3-yl-acetic acid methyl ester A mixture of 5-cyanomethyl-6-ethyl-pyridin-3-yl-acetic acid methyl ester (0.51 g, 2.34 mmol), 2-amino-3,4,6-trifluorothiophenol hydrochloride (0.54 g, 2.53 mmol) and BHT (10 mg) in a sealed reaction vessel is heated to 120° C. for 9 h. After cooling to room temperatue, the resulting slurry is adsorbed onto silica gel and purified by flash column chromatography (10-30% ethyl acetate in hexanes) to give 6-ethyl-5-(4,5,7-trifluoro-benzothiazol-2-ylmethyl)-pyridin-3-yl-acetic acid-methyl ester as a yellow oil (0.70 g, 79%): $R_f$ 0.36 (50% ethyl acetate in n-heptane), $^1$H NMR (CDCl$_3$, 300 MHz) δ 8.46 (s, 1 H), 7.64 (s, 1 H), 7.08-6.97 (m, 1 H), 4.50 (s, 2 H), 3.72 (s, 3 H), 3.65 (s, 2 H), 2.90 (q, J=7.4 Hz, 2 H), 1.29 (t, J=7.4 Hz, 3 H); ESI-LCMS m/z calcd for C$_{18}$H$_{15}$F$_3$N$_2$O$_2$S: 380.1; found 381.0 (M+1)$^+$.

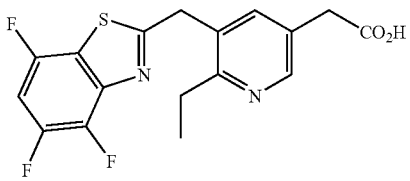

Part 5: 6-ethyl-5-(4,5,7-trifluoro-benzothiazol-2-ylmethyl)-pyridin-3-yl-acetic acid hydrochloride A solution of 6-ethyl-5-(4,5,7-trifluoro-benzothiazol-2-ylmethyl)-pyridin-3-yl-acetic acid-methyl ester (0.27 g, 0.71 mmol) in DME (5 mL, 0.1 M) is cooled to 0° C. under nitrogen and treated with 0.4 M NaOH (3 mL, 1.2 mmol). After stirring for 2 h, the solution is acidified with 2 M HCl, diluted with saturated aq NaCl (10 mL), extracted with ethyl acetate (3×10 mL) and dried over Na$_2$SO$_4$. Purification by HPLC (acetonitrile/water, 0.05% HCl) provided 6-ethyl-5-(4,5,7-trifluoro-benzothiazol-2-ylmethyl)-pyridin-3-yl-acetic acid hydrochloride as a white solid (0.21 g, 80%): mp 220° C. dec; $R_f$ 0.21 (10% methanol in dichloromethane), $^1$H NMR (DMSO-d$_6$, 300 MHz) δ 8.60 (s, 1 H), 8.18 (br s, 1 H), 7.78 (ddd, J$_1$=11.1 Hz, J$_2$=9.6 Hz, J$_3$=5.9 Hz, 1 H), 4.80 (s, 2 H), 3.79 (s, 2 H), 2.97 (q, J=7.6 Hz, 2 H), 1.20 (t, J=7.6 Hz, 3 H); ESI-LCMS m/z calcd for C$_{17}$H$_{13}$F$_3$N$_2$O$_2$S: 366.1; found 367.0 (M+1)$^+$. Anal. Calcd for C$_{17}$H$_{13}$F$_3$N$_2$O$_2$S.HCl: C, 50.69; H, 3.50; N, 6.95; S, 7.96. Found: C, 55.41; H, 3.56; N, 6.91; S, 7.98.

EXAMPLE 15

Preparation of 6-Phenyl-5-(4,5,7-trifluoro-benzothiazol-2-ylmethyl)-pyridin-3-yl-acetic acid hydrochloride

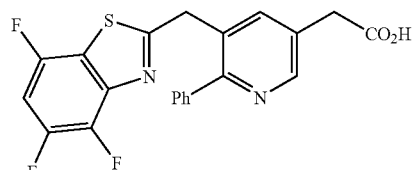

6-Phenyl-5-(4,5,7-trifluoro-benzothiazol-2-ylmethyl)-pyridin-3-yl-acetic acid hydrochloride is prepared in a manner analogous to that set forth in example 14, except 5-allyl-6-phenyl-pyridin-3-yl-acetic acid methyl ester is used instead of 5-allyl-6-ethyl-pyridin-3-yl-acetic acid methyl ester in part 1. mp 205-207° C. dec; $R_f$ 0.23 (10% methanol in dichloromethane), $^1$H NMR (DMSO-d$_6$, 300 MHz) δ 8.65 (s, 1 H), 8.12 (s, 1 H), 7.74 (ddd, J$_1$=11.1 Hz, J$_2$=9.2 Hz, J$_3$=5.6 Hz, 1 H), 7.58-7.43 (m, 5 H), 4.67 (s, 2 H), 3.81 (s, 2 H); ESI-LCMS m/z calcd for C$_{21}$H$_{13}$F$_3$N$_2$O$_2$S: 414.1; found 415.0 (M+1)$^+$. Anal. Calcd for C$_{21}$H$_{14}$F$_3$N$_2$O$_2$S.HCl: C, 55.94; H, 3.13; N, 6.21; S, 7.11. Found: C, 55.71; H, 3.24; N, 6.19; S, 7.18.

EXAMPLE 16

6-Benzyl-5-(4,5,7-trifluoro-benzothiazol-2-ylmethyl)-pyridin-3-yl-acetic acid hydrochloride

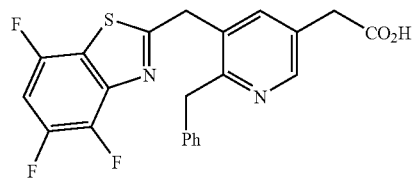

6-Benzyl-5-(4,5,7-trifluoro-benzothiazol-2-ylmethyl)-pyridin-3-yl-acetic acid hydrochloride is prepared in a manner analogous to that set forth in example 14, except 5-allyl-6-benzyl-pyridin-3-yl-acetic acid methyl ester is used instead of 5-allyl-6-ethyl-pyridin-3-yl-acetic acid methyl ester in part 1. mp 185° C. dec; $R_f$ 0.27 (10% methanol in dichloromethane), $^1$H NMR (DMSO-d$_6$, 300 MHz) δ 8.59 (s, 1 H), 8.07 (s, 1 H), 7.73 (ddd, J$_1$=11.1 Hz, J$_2$=9.3 Hz, J$_3$=5.6 Hz, 1 H), 7.16-7.00 (m, 5 H), 4.72 (s, 2 H), 4.33 (s, 2 H), 3.77 (s, 2 H).); ESI-LCMS m/z calcd for C$_{22}$H$_{15}$F$_3$N$_2$O$_2$S: 428.1; found 429.0 (M+1)$^+$. Anal. Calcd for C$_{17}$H$_{13}$F$_3$N$_2$O$_2$S.HCl: C, 56.84; H, 3.47; N, 6.03; S, 6.90. Found: C, 56.56; H, 3.55; N, 6.03; S, 6.95.

EXAMPLE 17

Preparation of 2-phenoxy-5-(4,5,7-trifluoro-benzothiazol-2-ylmethyl)-pyridin-3-yl)-acetic acid hydrochloride

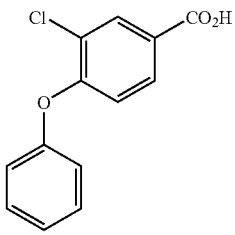

Part 1: 5-chloro-6-phenoxy-pyridin-3-yl-methanol

A solution of phenol (5.40 g, 57.38 mmol) in acetonitrile (18 mL) is cooled to 0° C. and added via cannula under a stream of nitrogen to a suspension of 95% sodium hydride (3.40 g, 134.6 mmol) in anhydrous acetonitrile/DMF (200 mL, 3:1 (v/v)) cooled to 0° C. After the addition is complete, the solution is stirred for 15 min and charged with dichloronicotinic acid (10.00 g, 52.08 mmol) in acetonitrile/DMF (30 mL, 3:1 (v/v)) via the same cannula. The mixture is warmed to a gentle reflux and stirred overnight. After cooling, water (400 mL) is added and the contents of the reaction is acidified with 2 M HCl. The orange solids are filtered, washed with water (100 mL), dried under high vacuum and used without further purification (ESI-LCMS m/z calcd for $C_{12}H_8ClNO_3$: 249.0; found 250.0 $(M+1)^+$).

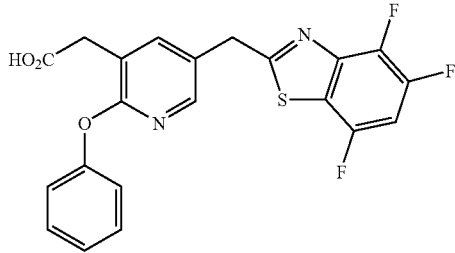

Part 2: 2-phenoxy-5-(4,5,7-trifluoro-benzothiazol-2-ylmethyl)-pyridin-3-yl)-acetic acid hydrochloride 2-Phenoxy-5-(4,5,7-trifluoro-benzothiazol-2-ylmethyl)-pyridin-3-yl)-acetic acid hydrochloride is prepared in a manner analogous to that set forth in example 14. ESI-LCMS m/z calcd for $C_{21}H_{13}F_3N_2O_3S$: 430.0; found 431.0 $(M+1)^+$.

EXAMPLE 18

Preparation of [2,5-Dimethyl-4-(4,5,7-trifluoro-benzothiazol-2-ylmethyl)-thiophen-3-yl]-acetic acid

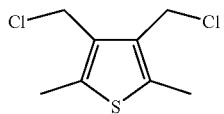

Part 1: 3,4-bis-chloromethyl-2,5-dimethyl-thiophene

A solution of trioxane (72.4 g, 804 mmol) in concentrated hydrochloric acid (75 mL) saturated with gaseous hydrochloric acid, is added to 2,5-dimethyl-thiophene (30.5 mL, 267 mmol) in a dropwise manner with stirring. After 2 h, the mixture is diluted with water and extracted with diethyl ether (3×). The organic layers are combined and washed successively with dilute hydrochloric acid, water, 5% sodium metabisulfite, water, dilute sodium hydroxide, and water. After removing the solvent under reduced pressure, the resulting solid is recrystallized with heptane to give 3,4-bis-chloromethyl-2,5-dimethyl-thiophene (45.9 g, 82%) as an off-white solid: mp 68-70° C.; $R_f$ 0.54 (10% heptane in ethyl acetate); $^1$H NMR (CDCl$_3$, 300 MHz) δ 4.60 (s, 4 H), 2.40 (s, 6 H).

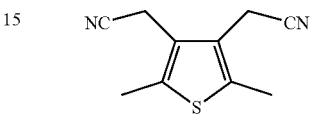

Part 2: (4-cyanomethyl-2,5-dimethyl-thiophen-3-yl)-acetonitrile

A suspension of potassium cyanide (13.2 g, 203 mmol) in DMF (66 mL) is cooled to 0° C. and carefully treated with a solution of 3,4-bis-chloromethyl-2,5-dimethyl-thiophene (10.0 g, 48.0 mmol) in DMF (34 mL). After warming to room temperature and stirring for 18 h, the solution is heated to 40° C. for 1 h, cooled to room temperature and diluted with chloroform and saturated aq NaCl. The chloroform layer is separated, and the aq layer extracted with chloroform. The combined organic layers are washed with saturated aq NaCl, dried over MgSO$_4$, filtered and concentrated in vacuo. The resulting residue is triturated with heptane, filtered under vacuum and dried overnight in a vacuum oven to give (4-cyanomethyl-2,5-dimethyl-thiophen-3-yl)-acetonitrile (8.6 g, 94.6%) as an off-white solid: mp 123.5-125.5° C.; $R_f$ 0.33 (30% ethyl acetate in heptane); $^1$H NMR (CDCl$_3$, 300 MHz) δ 3.65 (s, 4 H), 2.38 (s, 6 H).

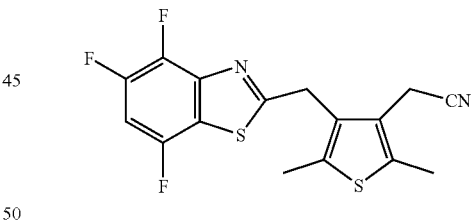

Part 3: [2,5-dimethyl-4-(4,5,7-trifluoro-benzothiazol-2-ylmethyl)-thiophen-3-yl]-acetonitrile A solution of (4-cyanomethyl-2,5-dimethyl-thiophen-3-yl)-acetonitrile (1.90 g, 10.0 mmol) and 2-amino-3,4,6-trifluoro-benzenethiol hydrochloride (2.16 g, 10.0 mmol) in EtOH (22 mL) is heated to reflux for 44 h. After cooling to room temperature, the mixture is concentrated in vacuo and purified by flash chromatography (silica gel, 10-30% ethyl acetate in heptane). Further purification by recrystallization with ethyl acetate and heptane gave [2,5-dimethyl-4-(4,5,7-trifluoro-benzothiazol-2-ylmethyl)-thiophen-3-yl]-acetonitrile (1.1 g, 31.2%) as a white powder: mp 145-146° C.; $R_f$ 0.54 (30% ethyl acetate in heptane); $^1$H NMR (CDCl$_3$, 300 MHz) δ 6.95-7.08 (m, 1 H), 4.36 (s, 2 H), 3.59 (s, 2 H), 2.43 (s, 3 H), 2.41 (s, 3 H).

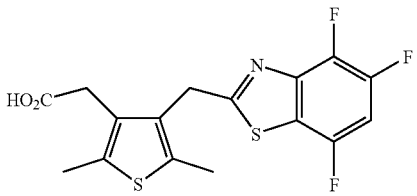

Part 4: [2,5-dimethyl-4-(4,5,7-trifluoro-benzothiazol-2-ylmethyl)-thiophen-3-yl]-acetic acid A solution of 2,5-dimethyl-4-(4,5,7-trifluoro-benzothiazol-2-ylmethyl)-thiophen-3-yl]-acetonitrile (1.0 g, 2.84 mmol) in concentrated hydrochloric acid (15 mL), water (15 mL) and THF (30 mL) is heated to reflux for 48 h. After cooling to room temperature, the reaction mixture is partially concentrated in vacuo and extracted with ethyl acetate. The extracts are washed with water, dried over MgSO4, filtered and concentrated in vacuo. The resulting residue is recrystallized with a mixture of ethyl acetate and heptane to give [2,5-dimethyl-4-(4,5,7-trifluoro-benzothiazol-2-ylmethyl)-thiophen-3-yl]-acetic acid (400 mg, 38%) as a white powder: mp 170-171° C.; $R_f$ 0.44 (10% methanol in dichloromethane); $^1$H NMR (CDCl$_3$, 300 MHz) δ 6.92-7.02 (m, 1 H), 4.36 (s, 2 H), 3.53 (s, 2 H), 2.41 (s, 3 H), 2.36 (s, 3 H); ESI-LC/MS m/z calcd for C$_{16}$H$_{12}$F$_3$NO$_2$S$_2$: 371.4; found 372.0 (M+1)$^+$. Anal calcd for C$_{16}$H$_{12}$F$_3$NO$_2$S$_2$: C, 51.74; H, 3.26; N, 3.77. Found C, 51.80; H, 3.29; N, 3.81.

EXAMPLE 19

Preparation of [5-(4,5,7-trifluoro-benzothiazol-2-ylmethyl)-thiophen-2-yl]-acetic acid

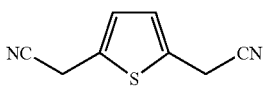

Part 1: (5-Cyanomethyl-thiophen-2-yl)-acetonitrile

A stream of hydrogen chloride gas is added to a stirred solution of aq formaldehyde (37%, 145.4 mL, 1.94 mol) and concentrated hydrochloric acid (35.6 mL, 433 mmol), until the solution became saturated. After the addition is complete, the mixture is allowed to cool to 30° C., and treated with thiophene (47.5 mL, 593 mmol) in a dropwise manner via syringe. After stirring 20 min, the oily brown layer is separated from the remaining mixture and washed with water (5×). The combined organic layers are filtered through celite (rinsing with dichloromethane), dried over Na$_2$SO$_4$, filtered and concentrated under reduced pressure to give 80.8 g 2,5-bis-chloromethyl-thiophene as a crude mixture to be used without further purification.

An solution of sodium cyanide (97.7 g, 1.99 mol) in anhydrous DMF (650 mL) is cooled to 0° C. and treated with 2,5-bis-chloromethyl-thiophene (84.7 g, 468 mmol) in one portion. The reaction mixture is allowed to warm to room temperature with stirring for 24 h, then heated to 40° C. for an additional 0.5 h. After cooling to room temperature, chloroform (300 mL) is added and the mixture is poured into saturated aq NaCl. After separation, the aq layer is extracted with chloroform (3×). The combined organic layers are washed with saturated aq NaCl, dried over MgSO$_4$, filtered and concentrated in vacuo. The resulting residue is purified by distillation to give (5-cyanomethyl-thiophen-2-yl)-acetonitrile (19.2 g, 25.3%) as a light brown oil: (bp 160-165° C., 0.75 mm Hg; $R_f$ 0.26 (15% ethyl acetate in heptane); $^1$H NMR (CDCl$_3$, 300 MHz) δ 6.93 (s, 2 H), 3.85 (s, 4 H).

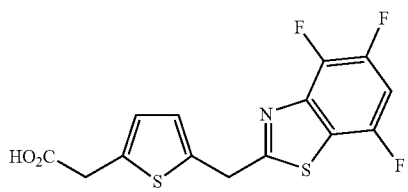

Part 2: [5-(4,5,7-trifluoro-benzothiazol-2-ylmethyl)-thiophen-2-yl]-acetic acid

[5-(4,5,7-Trifluoro-benzothiazol-2-ylmethyl)-thiophen-2-yl]-acetic acid is prepared in a manner analogous to that set forth in example 18, except (5-cyanomethyl-thiophen-2-yl)-acetonitrile is used instead of (4-cyanomethyl-2,5-dimethyl-thiophen-3-yl)-acetonitrile in part 3: mp 132-133° C.; $R_f$ 0.42 (10% methanol in methylene chloride); $^1$H NMR (CDCl$_3$, 300 MHz) δ 6.96-7.05 (m, 1 H), 6.93 (d, J=6.0 Hz, 1 H), 6.88 (d, J=6.0 Hz, 1 H), 4.60 (s, 2 H), 3.84 (s, 2 H); ESI-LC/MS m/z calcd for C$_{14}$H$_8$F$_3$NO$_2$S$_2$: 343.4; found 344.0 (M+1)$^+$. Anal calcd for C$_{14}$H$_8$F$_3$NO$_2$S$_2$: C, 48.98; H, 2.35; N, 4.08. Found C, 48.87; H, 2.39; N, 3.99.

EXAMPLE 20

Preparation of [2-methyl-5-(4,5,7-trifluorobenzothiazol-2-ylmethyl)-thiophen-3-yl]-acetic acid

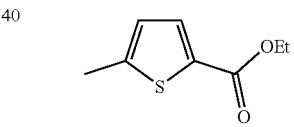

Part 1: 5-methyl-thiophene-2-carboxylic acid ethyl ester

A solution of 5-methyl-thiophene-2-carboxylic acid (25.2 g, 177 mmol) in EtOH (500 mL) is treated with conc. H$_2$SO$_4$ (15 mL) and heated to a gentle reflux for 72 h. The solution is partially concentrated and poured into water (500 mL) and extracted with Et$_2$O (3×). The combined extracts are washed with aq Na$_2$CO$_3$, water, dried over Na$_2$SO$_4$, filtered and concentrated in vacuo. Vacuum distillation of the residue afforded 5-methyl-thiophene-2-carboxylic acid ethyl ester (25.6 g, 85%): bp 98-99° C./9-10 mbar; $^1$H NMR (CDCl$_3$, 300 MHz) δ 7.6 (s, 1 H), 6.78 (s, 1 H), 4.30 (q, J=6.0 Hz, 2 H), 2.50 (s, 3 H), 1.34 (t, J=6.0 Hz, 3 H).

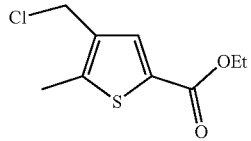

Part 2: 4-chloromethyl-5-methyl-thiophene-2-carboxylic acid ethyl ester

A solution of 5-methyl-thiophene-2-carboxylic acid ethyl ester (20.3 g, 0.119 mol) in chloromethyl methyl ether (265 mL, 3.3 mol) is treated with zinc chloride (16.3 g, 119 mmol) and stirred overnight at room temperature. The mixture is poured into water (800 mL) and extracted with dichloromethane (3×). The combined extracts are dried over $Na_2SO_4$, filtered and concentrated in vacuo. The resulting residue is distilled to give a mixture of desired product 4-chloromethyl-5-methyl-thiopene-2-carboxylic acid ethyl ester and 3,4-bis-chloromethyl-5-methyl-thiophene-2-carboxylic acid ethyl ester (3:1, 25.9 g) as a colorless oil which is used without further purification: bp 145-175° C./9 mbar.

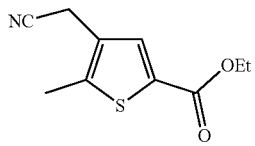

Part 3: 4-cyanomethyl-5-methyl-thiophene-2-carboxylic acid ethyl ester

A solution of the 4-chloromethyl-5-methyl-thiophene-2-carboxylic acid ethyl ester mixture from part 2 (25.6 g) in DMF (350 mL) is treated with potassium cyanide (20 g, 0.312 mol) and heated to 70° C. with stirring for 2 h. After cooling to room temperature, the solution is diluted with water and extracted with chloroform (2×). The combined organic layers are washed with saturated aq NaCl, dried over $Na_2SO_4$, filtered and concentrated in vacuo. The residue is purified by flash chromatography (10% ethyl acetate in heptane) to give 4-cyanomethyl-5-methyl-thiophene-2-carboxylic acid ethyl ester (4.7 g, 18.8%; 2 steps) as a white solid. mp 55-57° C.; $^1$H NMR (CDCl$_3$, 300 MHz) δ 7.63 (s, 1 H), 4.28 (q, J=6.0 Hz, 2 H), 3.60 (s, 2 H), 2.48 (s, 3 H), 1.38 (t, J=6.0 Hz, 3 H).

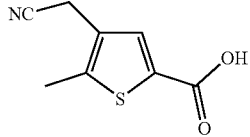

Part 4: 4-cyanomethyl-5-methyl-thiophene-2-carboxylic acid

A solution of 4-cyanomethyl-5-methyl-thiophene-2-carboxylic acid ethyl ester (21.3 g, 102 mmol) in EtOH (200 mL) is treated with a second solution of sodium bicarbonate (18.8 g, 224 mmol) in water (160 mL) and heated to reflux for 5 h. After cooling to room temperature, the mixture is diluted with water and extracted with ether. The aq layer is acidified with conc. HCl and the resulting precipitate is filtered, washed with water and vacuum-dried to give 12.4 g (67.2%) of the acid as an off-white powder: mp 196-198° C.; $^1$H NMR (DMSO-d$_6$, 300 MHz) δ 12.28 (s, 1 H), 6.90 (s, 1 H), 3.25 (s, 2 H), 1.75 (s, 3 H).

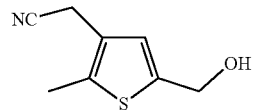

Part 5: (5-hydroxymethyl-2-methyl-thiophen-3-yl)-acetonitrile

A solution of 4-cyanomethyl-5-methyl-thiophene-2-carboxylic acid (12.3g, 67.9 mmol) in THF (400 mL) is treated with borane-dimethylsulfide complex (7.5 mL, 10 M, 74.7 mmol) dropwise via syringe. The mixture is heated to a gentle reflux for 2 h. After cooling, the mixture is quenched with water and extracted with dichloromethane (3×). The combined organic layers are dried over $Na_2SO_4$, filtered and concentrated in vacuo. The resulting residue is purified by flash chromatography (silica gel, 30-50% ethyl acetate in heptane) to give (5-hydroxymethyl-2-methyl-thiophen-3-yl)-acetonitrile (4.7 g, 41.4%) as a white solid. mp 66-68° C.; $^1$H NMR (CDCl$_3$, 300 MHz) δ 6.83 (s, 1 H), 4.71 (d, J=6.0 Hz, 2 H), 3.56 (s, 2 H), 2.40 (s, 3 H), 1.75 (t, J=6.0 Hz, 1 H).

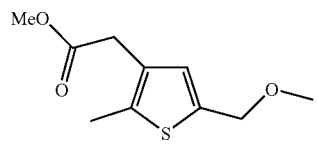

Part 6:

HCl gas is bubbled into a suspension of (5-hydroxymethyl-2-methyl-thiophen-3-yl)-acetonitrile (4.7 g, 28.1 mmol) in methanol (150 mL). After stirring for 2 h, the mixture is diluted with water and extracted with dichloromethane (3×). The combined organic layers are dried over $Na_2SO_4$, filtered and concentrated in vacuo. The residue is purified by flash chromatography (silica gel, 10% ethyl acetate in heptane) to give (5-methoxymethyl-2-methyl-thiophen-3-yl)-acetic acid methyl ester (2.6, 43.2%) as a colorless oil. $^1$H NMR (CDCl$_3$, 300 MHz) δ 6.80 (s, 1 H), 4.50 (s, 2 H), 3.70 (s, 3 H), 3.50 (s, 2 H), 3.18 (s, 3 H), 2.38 (s, 3 H).

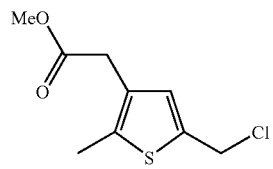

Part 7: (5-chloromethyl-2-methyl-thiophen-3-yl)-acetic acid methyl ester

A solution of (5-methoxymethyl-2-methyl-thiophen-3-yl)-acetic acid methyl ester (2.2 g, 10.1 mmol) in dichloromethane (60 mL) is cooled to −65° C. and treated with boron trichloride (10.1 mL, 1.0 M, 10.1 mmol) dropwise via syringe. The mixture is allowed to warm to 0° C., poured into ice-water and extracted with dichloromethane (3×). The combined organic extracts are washed with saturated aq NaCl, dried over Na$_2$SO$_4$, filtered and concentrated in vacuo to give (5-chloromethyl-2-methyl-thiophen-3-yl)-acetic acid methyl ester (2.2 g, 99%) as an orange oil. $^1$H NMR (CDCl$_3$, 300 MHz) δ 6.90 (s, 1 H), 4.72 (s, 2 H), 3.70 (s, 3 H), 3.50 (s, 2 H), 2.38 (s, 3 H).

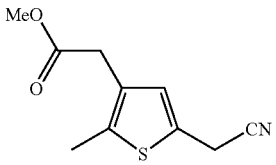

Part 8: (5-cyanomethyl-2-methyl-thiophen-3-yl)-acetic acid methyl ester

A solution of (5-chloromethyl-2-methyl-thiophen-3-yl)-acetic acid methyl ester (2.6 g, 12.1 mmol) and potassium cyanide (1.7 g, 25.4 mmol) in DMF (33 mL) is stirred for 14 h at room temperature then warmed to 50° C. for 0.5 h. After cooling, the mixture is poured into a mixture of CHCl$_3$ and saturated aq NaCl and extracted with CHCl$_3$. The combined extracts are washed with saturated aq NaCl, dried over MgSO$_4$, filtered and concentrated in vacuo. The resulting residue is purified by flash chromatography (silica gel, 10-50% ethyl acetate in heptane) to give (5-cyanomethyl-2-methyl-thiophen-3-yl)-acetic acid methyl ester (1.1 g, 43.4%): $^1$H NMR (CDCl$_3$, 300 MHz) δ 6.83 (s, 1 H), 3.80 (s, 2 H), 3.70 (s, 3 H), 3.50 (s, 2 H), 2.38 (s, 3 H).

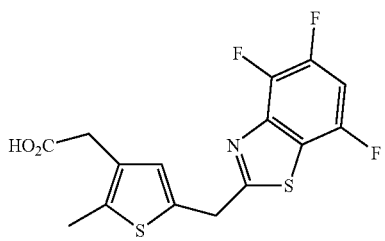

Part 9: [2-methyl-5-(4,5,7-trifluoro-benzothiazol-2-ylmethyl)-thiophen-3-yl]-acetic acid

[2-Methyl-5-(4,5,7-trifluoro-benzothiazol-2-ylmethyl)-thiophen-3-yl]-acetic acid is prepared in a manner analogous to that set forth in Example 1, except (5-cyanomethyl-2-methyl-thiophen-3-yl)-acetic acid methyl ester is used instead of (4-cyanomethyl-2,5-dimethyl-thiophen-3-yl)-acetonitrile in formation of the benzothiazole ring. Hydrolysis of the ester provided the desired final compound.

EXAMPLE 21

Preparation of [4-(4,5,7-Trifluoro-benzothiazol-2-ylmethyl)-thiophen-2-yl]-acetic acid

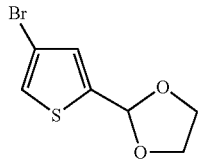

Part 1: 2-(4-bromo-thiophen-2-yl)-[1,3]dioxolane

A mixture of 4-bromo-thiophene-2-carbaldehyde (175 g, 916 mmol), ethylene glycol (71.1 g, 1.15 mol) and p-toluenesulfonic acid (0.19 g, 1.0 mmol) in toluene (250 mL) is heated to reflux for 7 h using a Dean-Stark apparatus. After cooling, the solution is washed with aq NaHCO$_3$, dried over Na$_2$SO$_4$, filtered and concentrated in vacuo. The residue is distilled to give 2-(4-bromo-thiophen-2-yl)-[1,3]dioxolane (210.6 g, 98%) as a colorless liquid: bp 133-143/11-14 mBar; $^1$H NMR (CDCl$_3$, 300 MHz) δ 7.21 (s, 1 H), 7.04 (s, 1 H), 6.04 (s, 1 H), 3.95-4.18 (m, 4 H).

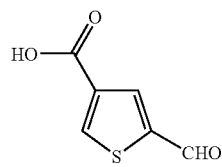

Part 2:

A solution of 2-(4-bromo-thiophen-2-yl)-[1,3]dioxolane (49.0 g, 208 mmol) in Et$_2$O (375 mL) is cooled to −78° C. and treated with n-BuLi (100 mL, 2.5 M, 250 mmol) dropwise. After the addition is complete, the solution is stirred for 15 min, and carbon dioxide is bubbled through the solution until the reaction is complete. The mixture is allowed to warm to room temperature and water is added. The aqueous layer is separated and the organic layer is extracted with water (2×). The combined aqueous layers are acidified with concentrated HCl. The resulting precipitate is filtered, and washed successively with water and heptane to give 5-formyl-thiophene-3-carboxylic acid (20.6 g, 63%) as a white solid: mp 171-173° C.; $^1$H NMR (DMSO-d$_6$, 300 MHz) δ 13.15 (s, 1 H), 9.95 (s, 1 H), 8.74 (s, 1 H), 8.30 (s, 1 H).

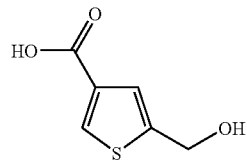

Part 3:

A solution of sodium borohydride (12.5 g, 330 mmol) in water (150 mL) and ethanol (100 mL) at 0° C. is charged with 5-formyl-thiophene-3-carboxylic acid (20.6 g, 132 mmol) in one portion. After warming to room temperature and stirring for 4 h, the mixture is diluted with water and the resulting precipitate vacuum filtered. The filtrate is concentrated and the resulting aqueous solution is washed with ether (2×). The aq layer is acidified with concentrated HCl and extracted with ether (3×). The combined ether extracts are dried over Na$_2$SO$_4$, filtered and concentrated in vacuo to give 5-hydroxymethyl-thiophene-3-carboxylic acid (14.6, 70%) as a white solid; mp 149° C.; $^1$H NMR (DMSO-d$_6$, 300 MHz) δ 12.60 (s, 1 H), 8.10 (s, 1 H), 7.20 (s, 1 H), 5.52 (t, J=6.0 Hz, 1 H), 4.60 (s, 2 H).

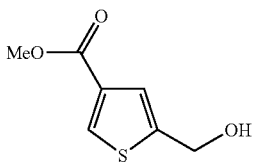

Part 4:

A mixture of 5-hydroxymethyl-thiophene-3-carboxylic acid (14.5 g, 91.7 mmol), concentrated H$_2$SO$_4$ (5.2 mL, 93.5 mmol) and methanol (250 mL) is heated to reflux for 3.5 h. After cooling, the mixture is poured into water and extracted with dichloromethane (3×). The combined extracts are washed successively with saturated aq NaCl, aq NaHCO$_3$ and water followed by drying over Na$_2$SO$_4$, filtration and concentration in vacuo. The residue is purified by distillation to give 5-hydroxymethyl-thiophene-3-carboxylic acid methyl ester (8.8 g, 56%) as a clear oil: bp 155-157° C./6-7 mbar; $^1$H NMR (CDCl$_3$, 300 MHz) δ 7.98 (s, 1 H), 7.35 (s, 1 H), 4.78 (s, 2 H), 3.80 (s, 3 H), 2.63 (s, 1 H).

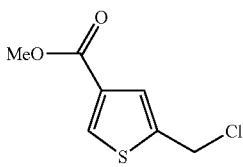

Part 5: 5-chloromethyl-thiophene-3-carboxylic acid methyl ester

A solution of 5-hydroxymethyl-thiophene-3-carboxylic acid methyl ester (8.8 g, 51.1 mmol) and triethylamine (7.8 mL, 56.2 mmol) in dichloromethane (135 mL) is cooled to 0° C. and treated with a solution of thionyl chloride (4.1 mL, 56.2 mmol) in dichloromethane (40 mL) in a dropwise maner. After stirring for 1 h, water is added and the mixture is extracted with dichloromethane. The combined organics are dried over Na$_2$SO$_4$, filtered and concentrated in vacuo. The residue is purified by flash chromatography (silica gel, 10% ethyl acetate in heptane) to give 5-chloromethyl-thiophene-3-carboxylic acid methyl ester (4.5 g, 46%) an amber oil. $^1$H NMR (CDCl$_3$, 300 MHz) δ 8.04 (s, 1 H), 7.43 (s, 1 H), 4.78 (s, 2 H), 3.84 (s, 3 H).

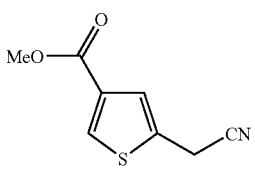

Part 6: 5-cyanomethyl-thiophene-3-carboxylic acid methyl ester

A solution of potassium cyanide (3.2 g, 48.5 mmol) in DMF (25 mL) is treated with 5-chloromethyl-thiophene-3-carboxylic acid methyl ester (4.4 g, 23.1 mmol) in DMF (30 mL). After stirring for 14 h at room temperature the mixture is warmed to 50° C. for 0.5 h. After cooling, the solution is diluted with saturated aq NaCl and extracted with CHCl$_3$ (3×). The combined organic layers are dried over MgSO$_4$, filtered and concentrated in vacuo to give 5-cyanomethyl-thiophene-3-carboxylic acid methyl ester (4.4 g, 100%). $^1$H NMR (CDCl$_3$, 300 MHz) δ 8.00 (s, 1 H), 7.44 (s, 1 H), 3.90 (s, 2 H), 3.84 (s, 3 H).

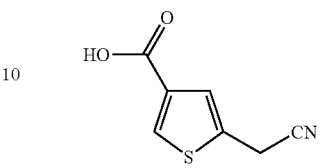

Part 7: 5-cyanomethyl-thiophene-3-carboxylic acid

A solution of 5-cyanomethyl-thiophene-3-carboxylic acid methyl ester (4.4 g, 22.1 mmol) and NHCO$_3$ (4.1 g, 48.6 mmol) in water (35 mL) and ethanol (35 mL) is heated to reflux for 4 h. After cooling, the reaction mixture is diluted with water and washed with ether. The aqueous layer is acidified with 1 N HCl and extracted with dichloromethane (4×). The combined organic layers are washed with saturated aq NaCl, dried over Na$_2$SO$_4$, filtered and concentrated in vacuo to give 5-cyanomethyl-thiophene-3-carboxylic acid (2.7 g, 73%) as a light yellow solid: mp 154-159° C.; $^1$H NMR (DMSO-d$_6$, 300 MHz) δ 12.72 (s, 1 H), 8.20 (s, 1 H), 7.30 (s, 1 H), 4.23 (s, 2 H).

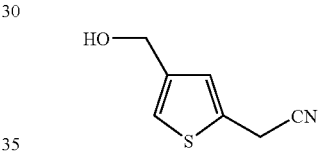

Part 8: (4-hydroxymethyl-thiophen-2-yl)-acetonitrile

A solution of 5-cyanomethyl-thiophene-3-carboxylic acid (2.7 g, 16.1 mmol) in THF (95 mL) is treated with borane dimethylsulfide (1.78 mL, 10.0 M, 17.8 mmol) in a dropwise maner. After the addition is complete, the solution is warmed to reflux for 1 h. After cooling, water is added and the mixture is extracted with dichloromethane (3×). The combined extracts are dried over Na$_2$SO$_4$, filtered and concentrated in vacuo. The residue is purified by flash chromatography (silica gel, 30-50% ethyl acetate in heptane) to give (4-hydroxymethyl-thiophen-2-yl)-acetonitrile (1.7 g, 69%) as a white solid: mp 45-47° C.; $^1$H NMR (CDCl$_3$, 300 MHz) δ 7.16 (s, 1 H), 7.02 (s, 1 H), 4.60 (s, 2 H), 3.84 (s, 2 H), 1.79 (s, 1 H).

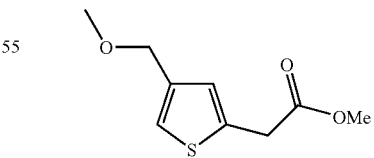

Part 9: (4-methoxymethyl-thiophen-2-yl)-acetic acid methyl ester

Hydrogen chloride gas is bubbled into a suspension of (5-hydroxymethyl-2-methyl-thiophen-3-yl)-acetonitrile (1.7 g, 11.1 mmol) in methanol (20 mL). After stirring for 2 h, the mixture is diluted with water and extracted with dichloromethane (3×). The combined organic layers are dried over Na₂SO₄, filtered and concentrated in vacuo. The residue is purified by flash chromatography (silica gel, 10% ethyl acetate in heptane) to (4-methoxymethyl-thiophen-2-yl)-acetic acid methyl ester (0.70 g, 31.5%) as a colorless oil: ¹H NMR (CDCl₃, 300 MHz) δ 7.08 (s, 1 H), 6.90 (s, 1 H), 4.38 (s, 2 H), 3.80 (s, 2 H), 3.72 (s, 3 H), 3.35 (s, 3 H).

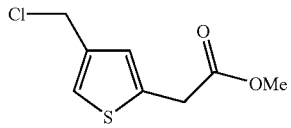

Part 10: (4-chloromethyl-thiophen-2-yl)-acetic acid methyl ester

A solution of (4-methoxymethyl-thiophen-2-yl)-acetic acid methyl ester (0.70 g, 3.50 mmol) in dichloromethane (20 mL) is treated with boron trichloride (3.50 mL, 1.0 M, 3.50 mmol) in a dropwise maner. After stirring at room temperature for 30 min the mixture is poured into water and extracted with dichloromethane (3×). The combined organic layers are washed with saturated aq NaCl, dried over Na₂SO₄, filtered and concentrated in vacuo. The resulting residue is purified by chromatography (silica gel, 5-10% ethyl acetate in heptane) to give (4-chloromethyl-thiophen-2-yl)-acetic acid methyl ester (0.58 g, 81%) as a colorless oil: ¹H NMR (CDCl₃, 300 MHz) δ 7.18 (s, 1 H), 6.95 (s, 1 H), 4.52 (s, 2 H), 3.80 (s, 2 H), 3.72 (s, 3 H).

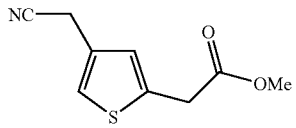

Part 11: (4-cyanomethyl-thiophen-2-yl)-acetic acid methyl ester

A solution of (4-chloromethyl-thiophen-2-yl)-acetic acid methyl ester (0.58 g, 2.83 mmol) and potassium cyanide (0.39 g, 5.95 mmol) in DMF (15 mL) is stirred at room temperature for 14 h then heated to 50° C. for 0.5 h. The mixture is quenched with saturated aq NaCl and extracted with CHCl₃ (3×). The combined organic layers are washed with saturated aq NaCl, dried over Na₂SO₄, filtered and concentrated in vacuo. The residue is purified by chromatography (silica gel, 10% ethyl acetate in heptane) to give (4-cyanomethyl-thiophen-2-yl)-acetic acid methyl ester (0.43 g, 78%) as a colorless oil: ¹H NMR (CDCl₃, 300 MHz) δ 7.10 (s, 1 H), 6.95 (s, 1 H), 3.80 (s, 2 H), 3.72 (s, 3 H), 3.65 (s, 2 H).

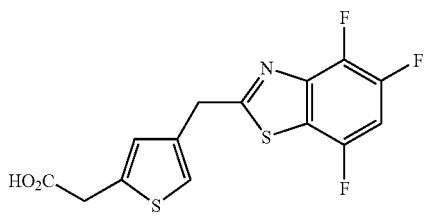

Part 12: [4-(4,5,7-Trifluoro-benzothiazol-2-ylmethyl)-thiophen-2-yl]-acetic acid The title compound is prepared analogous to the procedure employed in Example 1 or Example 4. Purification by chromatography (silica gel, 5% methanol in dichloromethane) gives [4-(4,5,7-Trifluoro-benzothiazol-2-ylmethyl)-thiophen-2-yl]-acetic acid (180 mg, 49%). mp 144-146° C.; R_f 0.36 (10% methanol in dichloromethane); ¹H NMR (DMSO-d₆, 300 MHz) δ 12.45 (s, 1 H), 7.67-7.78 (m, 1 H), 7.38 (s, 1 H), 6.92 (s, 1 H), 4.45 (s, 2 H), 3.80 (s, 2 H); ESI-LC/MS calcd for C₁₄H₈F₃NO₂S₂: 343.4; found 344 (M+1)⁺. Anal calcd for C₁₄H₈F₃NO₂S₂: C, 48.98; H, 2.35; N, 4.08. Found C, 48.92; H, 2.45; N, 3.24.

EXAMPLE 22

Preparation of [4-(5-trifluoromethybenzothiazol-2-ylmethyl)-thiophen-2-yl]-acetic acid

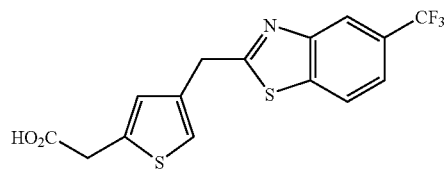

[4-(5-Trifluoromethybenzothiazol-2-ylmethyl)-thiophen-2-yl]-acetic acid is prepared in a manner analogous to that set forth above in Example 18, except 2-amino-5-trifluoromethylbenzenethiol hydrochloride is used instead and 2-amino-3,4,6-trifluoro-benzenethiol hydrochloride in formation of the benzothiazole ring: mp 131-132° C.; R_f 0.35 (10% methanol in methylene chloride); ¹H NMR (DMSO-d₆, 300 MHz) δ 12.45 (s, 1 H), 8.25-8.30 (m, 2 H), 7.75 (d, J=12 Hz, 1H), 7.35 (s, 1H), 6.90 (s, 1H), 4.44 (s, 2H), 3.78 (s, 2H); ESI-LC/MS m/z calcd for C₁₅H₁₀F₃NO₂S₂: 357.4; found 358.0 (M+1)⁺. Anal calcd for C₁₅H₁₀F₃NO₂S₂: C, 50.41; H, 2.82; N, 3.92. Found C, 50.61; H, 2.77; N, 3.95.

EXAMPLE 23

Preparation of [2-(4,5,7-trifluoro-benzothiazol-2-ylmethyl)-thiophen-3-yl]-acetic acid

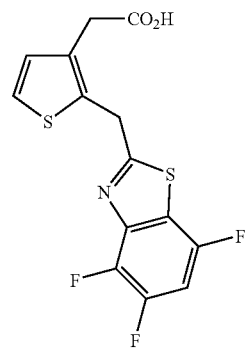

[2-(4,5,7-Trifluoro-benzothiazol-2-ylmethyl)-thiophen-3-yl]-acetic acid is prepared in a manner analogous to that set forth in Example 1, except (2-cyanomethyl-thiophen-3-yl)-acetonitrile is used instead of (4-cyanomethyl-2,5-dimethylthiophen-3-yl)-acetonitrile in the formation of the benzothiazole ring. Minor regioisomer obtained during course of isolation: mp 142-144° C.; $R_f$ 0.30 (10% methanol in methylene chloride); $^1$H NMR (CDCl$_3$, 300 MHz) δ 7.28 (d, J=6 Hz, 1H), 6.93-7.10 (m, 2H), 4.62 (s, 2H), 4.42 (s, 2×0.09H), 3.95 (s, 2×0.09H), 3.84 (s, 2H); ESI-LC/MS m/z calcd for $C_{14}H_8F_3NO_2S_2$: 343.4; found 344.0 (M+1)$^+$. Anal calcd for $C_{14}H_8F_3NO_2S_2$: C, 48.98; H, 2.35; N, 4.08. Found C, 48.87; H, 2.39; N, 3.99.

EXAMPLE 24

Preparation of [4-methyl-5-(4,5,7-trifluoro-benzothiazol-2-ylmethyl)-thiophen-3-yl]-acetic acid

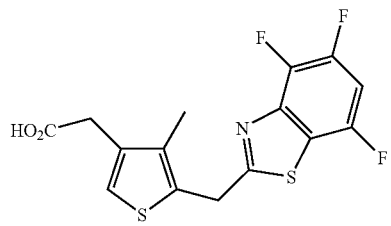

[4-Methyl-5-(4,5,7-trifluoro-benzothiazol-2-ylmethyl)-thiophen-3-yl]-acetic acid is prepared in a manner analogous to that set forth in Example 1, (4-Cyanomethyl-3-methyl-thiophen-2-yl)-acetonitrile is used instead of (4-cyanomethyl-2,5-dimethyl-thiophen-3-yl)-acetonitrile in the formation of the benzothiazole ring. Minor regioisomer obtained during course of isolation (6%): $^1$H NMR (DMSO-d$_6$, 300 MHz) δ 7.68-7.80 (m, 1H), 7.35 (s, 0.06 H), 7.21 (s, 1H), 4.60 (s, 2H), 4.50 (s, 2×0.06 H), 3.80 (s, 2×0.06H), 3.49 (s, 2H), 2.10 (s, 1H), 2.01 (s, 3×0.06 H); ESI-LC/MS m/z calcd for $C_{15}H_{10}F_3NO_2S_2$: 357.4; found 358.0 (M+1)$^+$.

EXAMPLES 24A-24U

Example 24A

[6-methyl-3-(4,5,7-trifluoro-benzothiazol-2-ylmethyl)-pyrrolo[2,3-b]pyridin-1-yl]-acetic acid (m)ethyl ester Example 24B

[3-(4,5,7-trifluoro-benzothiazol-2-ylmethyl)-pyrrolo[2,3-b]pyridin-1-yl]-acetic acid (m)ethyl ester Example 24C 2,6-Dimethyl-5-(4,5,7-trifluoro-benzothiazole-2-ylmethyl)-pyridin-3-yl-acetic acid hydrochloride (m)ethyl ester Example 24D

[2,6-Diethyl-5-(4,5,7-trifluoro-benzothiazol-2-ylmethyl)-pyridin-3-yl] acetic acid methyl ester Example 24E

[2,6-Diphenyl-5-(4,5,7-trifluoro-benzothiazol-2-ylmethyl)-pyridin-3-yl] acetic acid (m)ethyl ester Example 24F

[2,6-Dipropyl-5-(4,5,7-trifluoro-benzothiazol-2-ylmethyl)-pyridin-3-yl] acetic acid methyl ester Example 24G 5-(4,5,7-trifluoro-benzothiazol-2-ylmethyl)-pyridin-3-yl-acetic acid (m)ethyl ester Example 24H 2,4,6-trimethyl-5-(4,5,7-trifluoro-benzothiazol-2-ylmethyl)-pyridin-3-yl-acetic acid (m)ethyl ester Example 24I 2,6-dimethyl-4-ethyl-5-(4,5,7-trifluoro-benzothiazol-2-ylmethyl)-pyridin-3-yl-acetic acid (m)ethyl ester Example 24J 2-Ethyl-5-(4,5,7-trifluoro-benzothiazol-2-ylmethyl)-pyridin-3-yl-acetic acid (m)ethyl ester Example 24K 2-benzyl-5-(4,5,7-trifluoro-benzothiazol-2-ylmethyl)-pyridin-3-yl-acetic acid (m)ethyl ester Example 24L 2-phenyl-5-(4,5,7-trifluoro-benzothiazol-2-ylmethyl)-pyridin-3-yl-acetic acid (m)ethyl ester Example 24M 6-Phenyl-5-(4,5,7-trifluoro-benzothiazol-2-ylmethyl)-pyridin-3-yl-acetic acid (m)ethyl ester Example 24N 6-Benzyl-5-(4,5,7-trifluoro-benzothiazol-2-ylmethyl)-pyridin-3-yl-acetic acid methyl ester Example 24O 2-phenoxy-5-(4,5,7-trifluoro-benzothiazol-2-ylmethyl)-pyridin-3-yl)-acetic acid methyl ester Example 24P

[2,5-dimethyl-4-(4,5,7-trifluoro-benzothiazol-2-ylmethyl)-thiophen-3-yl]-acetic acid (m)ethyl ester Example 24Q

[5-(4,5,7-trifluoro-benzothiazol-2-ylmethyl)-thiophen-2-yl]-acetic acid

87

Example 24R

[4-(4,5,7-Trifluoro-benzothiazol-2-ylmethyl)-thiophen-2-yl]-acetic acid methyl ester

Example 24S

[4-(5-trifluoromethybenzothiazol-2-ylmethyl)-thiophen-2-yl]-acetic acid (m)ethyl ester

Example 24T

[2-(4,5,7-trifluoro-benzothiazol-2-ylmethyl)-thiophen-3-yl]-acetic acid (m)ethyl ester

88

Example 24U

[4-methyl-5-(4,5,7-trifluoro-benzothiazol-2-ylmethyl)-thiophen-3-yl]-acetic acid methyl ester

EXAMPLES 25-188

The compounds of Examples 25-188, which are represented by Formula IA below, are prepared essentially according to the procedures set forth above in the schemes and Examples 1-24. The various substituents A, Z, R5a, R5b, R5c, R'a, R'b, R'c, R'd are defined in Table 1.

TABLE 1

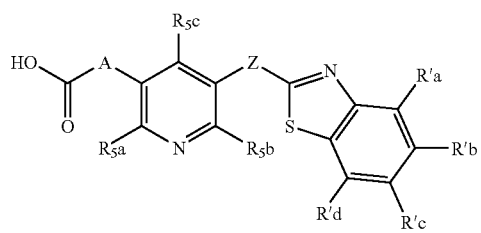

IA

| Example number | A | Z | R5a | R5b | R5c | R'a | R'b | R'c | R'd |
|---|---|---|---|---|---|---|---|---|---|
| 25 | $CH_2$ | $CH_2$ | H | $CH_2CH_3$ | H | F | H | H | H |
| 26 | $CH_2$ | $CH_2$ | H | $CH_2CH_3$ | H | F | F | H | H |
| 27 | $CH_2$ | $CH_2$ | H | $CH_2CH_3$ | H | F | H | H | F |
| 28 | $CH_2$ | $CH_2$ | H | $CH_2CH_3$ | H | H | F | H | H |
| 29 | $CH_2$ | $CH_2$ | H | $CH_2CH_3$ | H | H | F | H | F |
| 30 | $CH_2$ | $CH_2$ | H | $CH_2CH_3$ | H | H | H | F | F |
| 31 | $CH_2$ | $CH_2$ | H | $CH_2CH_3$ | H | H | $CF_3$ | H | H |
| 32 | $CH_2$ | $CH_2$ | H | $CH_2CH_3$ | H | H | H | H | $CF_3$ |
| 33 | $CH_2$ | $CH_2$ | H | $CH_2CH_3$ | H | F | $CF_3$ | H | H |
| 34 | $CH_2$ | $CH_2$ | H | $CH_2CH_3$ | H | H | $CF_3$ | H | F |
| 35 | $CH_2$ | $CH_2$ | H | $CH_2CH_3$ | H | H | Cl | H | H |
| 36 | $CH_2$ | $CH_2$ | $CH_2CH_3$ | H | H | F | H | H | H |
| 37 | $CH_2$ | $CH_2$ | $CH_2CH_3$ | H | H | F | F | H | H |
| 38 | $CH_2$ | $CH_2$ | $CH_2CH_3$ | H | H | F | H | H | F |
| 39 | $CH_2$ | $CH_2$ | $CH_2CH_3$ | H | H | H | F | H | H |
| 40 | $CH_2$ | $CH_2$ | $CH_2CH_3$ | H | H | H | F | H | F |
| 41 | $CH_2$ | $CH_2$ | $CH_2CH_3$ | H | H | H | H | F | F |
| 42 | $CH_2$ | $CH_2$ | $CH_2CH_3$ | H | H | H | $CF_3$ | H | H |
| 43 | $CH_2$ | $CH_2$ | $CH_2CH_3$ | H | H | H | H | H | $CF_3$ |
| 44 | $CH_2$ | $CH_2$ | $CH_2CH_3$ | H | H | F | $CF_3$ | H | H |
| 45 | $CH_2$ | $CH_2$ | $CH_2CH_3$ | H | H | H | $CF_3$ | H | F |
| 46 | $CH_2$ | $CH_2$ | $CH_2CH_3$ | H | H | H | Cl | H | H |
| 47 | $CH_2$ | $CH_2$ | H | $CH_3$ | H | F | H | H | H |
| 48 | $CH_2$ | $CH_2$ | H | $CH_3$ | H | F | F | H | H |
| 49 | $CH_2$ | $CH_2$ | H | $CH_3$ | H | F | H | H | F |
| 50 | $CH_2$ | $CH_2$ | H | $CH_3$ | H | H | F | H | H |
| 51 | $CH_2$ | $CH_2$ | H | $CH_3$ | H | H | F | H | F |
| 52 | $CH_2$ | $CH_2$ | H | $CH_3$ | H | H | H | F | F |
| 53 | $CH_2$ | $CH_2$ | H | $CH_3$ | H | H | $CF_3$ | H | H |
| 54 | $CH_2$ | $CH_2$ | H | $CH_3$ | H | H | H | H | $CF_3$ |
| 55 | $CH_2$ | $CH_2$ | H | $CH_3$ | H | F | $CF_3$ | H | H |
| 56 | $CH_2$ | $CH_2$ | H | $CH_3$ | H | H | $CF_3$ | H | F |
| 57 | $CH_2$ | $CH_2$ | H | $CH_3$ | H | H | Cl | H | H |
| 58 | $CH_2$ | $CH_2$ | $CH_3$ | H | H | F | H | H | H |
| 59 | $CH_2$ | $CH_2$ | $CH_3$ | H | H | F | F | H | H |
| 60 | $CH_2$ | $CH_2$ | $CH_3$ | H | H | F | H | H | F |
| 61 | $CH_2$ | $CH_2$ | $CH_3$ | H | H | H | F | H | H |
| 62 | $CH_2$ | $CH_2$ | $CH_3$ | H | H | H | F | H | F |
| 63 | $CH_2$ | $CH_2$ | $CH_3$ | H | H | H | H | F | F |
| 64 | $CH_2$ | $CH_2$ | $CH_3$ | H | H | H | $CF_3$ | H | H |
| 65 | $CH_2$ | $CH_2$ | $CH_3$ | H | H | H | H | H | $CF_3$ |
| 66 | $CH_2$ | $CH_2$ | $CH_3$ | H | H | F | $CF_3$ | H | H |
| 67 | $CH_2$ | $CH_2$ | $CH_3$ | H | H | H | $CF_3$ | H | F |

TABLE 1-continued

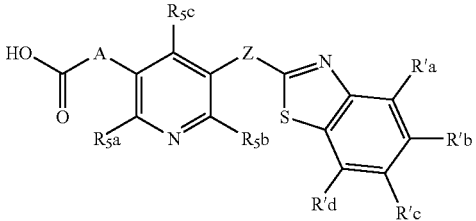

| Example number | A | Z | R5a | R5b | R5c | R'a | R'b | R'c | R'd |
|---|---|---|---|---|---|---|---|---|---|
| 68 | $CH_2$ | $CH_2$ | $CH_3$ | H | H | H | Cl | H | H |
| 69 | $CH_2$ | $CH_2$ | H | OH | H | F | H | H | H |
| 70 | $CH_2$ | $CH_2$ | H | OH | H | F | F | H | H |
| 71 | $CH_2$ | $CH_2$ | H | OH | H | F | H | H | F |
| 72 | $CH_2$ | $CH_2$ | H | OH | H | H | F | H | H |
| 73 | $CH_2$ | $CH_2$ | H | OH | H | H | F | H | F |
| 74 | $CH_2$ | $CH_2$ | H | OH | H | H | H | F | F |
| 75 | $CH_2$ | $CH_2$ | H | OH | H | H | $CF_3$ | H | H |
| 76 | $CH_2$ | $CH_2$ | H | OH | H | H | H | H | $CF_3$ |
| 77 | $CH_2$ | $CH_2$ | H | OH | H | F | $CF_3$ | H | H |
| 78 | $CH_2$ | $CH_2$ | H | OH | H | H | $CF_3$ | H | F |
| 79 | $CH_2$ | $CH_2$ | H | OH | H | H | Cl | H | H |
| 80 | $CH_2$ | $CH_2$ | OH | H | H | F | H | H | H |
| 81 | $CH_2$ | $CH_2$ | OH | H | H | F | F | H | H |
| 82 | $CH_2$ | $CH_2$ | OH | H | H | F | H | H | F |
| 83 | $CH_2$ | $CH_2$ | OH | H | H | H | F | H | H |
| 84 | $CH_2$ | $CH_2$ | OH | H | H | H | F | H | F |
| 85 | $CH_2$ | $CH_2$ | OH | H | H | H | H | F | F |
| 86 | $CH_2$ | $CH_2$ | OH | H | H | H | $CF_3$ | H | H |
| 87 | $CH_2$ | $CH_2$ | OH | H | H | H | H | H | $CF_3$ |
| 88 | $CH_2$ | $CH_2$ | OH | H | H | F | $CF_3$ | H | H |
| 89 | $CH_2$ | $CH_2$ | OH | H | H | H | $CF_3$ | H | F |
| 90 | $CH_2$ | $CH_2$ | OH | H | H | H | Cl | H | H |
| 91 | $CH_2$ | $CH_2$ | H | $NH_2$ | H | F | H | H | H |
| 92 | $CH_2$ | $CH_2$ | H | $NH_2$ | H | F | F | H | H |
| 93 | $CH_2$ | $CH_2$ | H | $NH_2$ | H | F | H | H | F |
| 94 | $CH_2$ | $CH_2$ | H | $NH_2$ | H | H | F | H | H |
| 95 | $CH_2$ | $CH_2$ | H | $NH_2$ | H | H | F | H | F |
| 96 | $CH_2$ | $CH_2$ | H | $NH_2$ | H | H | H | F | F |
| 97 | $CH_2$ | $CH_2$ | H | $NH_2$ | H | H | $CF_3$ | H | H |
| 98 | $CH_2$ | $CH_2$ | H | $NH_2$ | H | H | H | H | $CF_3$ |
| 99 | $CH_2$ | $CH_2$ | H | $NH_2$ | H | F | $CF_3$ | H | H |
| 100 | $CH_2$ | $CH_2$ | H | $NH_2$ | H | H | $CF_3$ | H | F |
| 101 | $CH_2$ | $CH_2$ | H | $NH_2$ | H | H | Cl | H | H |
| 102 | $CH_2$ | $CH_2$ | H | $NH_2$ | H | F | F | H | F |
| 103 | $CH_2$ | $CH_2$ | $NH_2$ | H | H | F | H | H | H |
| 104 | $CH_2$ | $CH_2$ | $NH_2$ | H | H | F | F | H | H |
| 105 | $CH_2$ | $CH_2$ | $NH_2$ | H | H | F | H | H | F |
| 106 | $CH_2$ | $CH_2$ | $NH_2$ | H | H | H | F | H | H |
| 107 | $CH_2$ | $CH_2$ | $NH_2$ | H | H | H | F | H | F |
| 108 | $CH_2$ | $CH_2$ | $NH_2$ | H | H | H | H | F | F |
| 109 | $CH_2$ | $CH_2$ | $NH_2$ | H | H | H | $CF_3$ | H | H |
| 110 | $CH_2$ | $CH_2$ | $NH_2$ | H | H | H | H | H | $CF_3$ |
| 111 | $CH_2$ | $CH_2$ | $NH_2$ | H | H | F | $CF_3$ | H | H |
| 112 | $CH_2$ | $CH_2$ | $NH_2$ | H | H | H | $CF_3$ | H | F |
| 113 | $CH_2$ | $CH_2$ | $NH_2$ | H | H | H | Cl | H | H |
| 114 | $CH_2$ | $CH_2$ | $NH_2$ | H | H | F | H | F | F |
| 115 | $CH_2CH_2$ | $CH_2$ | H | $CH_2CH_3$ | H | F | H | H | H |
| 116 | $CH_2CH_2$ | $CH_2$ | H | $CH_2CH_3$ | H | F | F | H | H |
| 117 | $CH_2CH_2$ | $CH_2$ | H | $CH_2CH_3$ | H | F | H | H | F |
| 118 | $CH_2CH_2$ | $CH_2$ | H | $CH_2CH_3$ | H | H | F | H | H |
| 119 | $CH_2CH_2$ | $CH_2$ | H | $CH_2CH_3$ | H | H | F | H | F |
| 120 | $CH_2CH_2$ | $CH_2$ | H | $CH_2CH_3$ | H | H | H | F | F |
| 121 | $CH_2CH_2$ | $CH_2$ | H | $CH_2CH_3$ | H | H | $CF_3$ | H | H |
| 122 | $CH_2CH_2$ | $CH_2$ | H | $CH_2CH_3$ | H | H | H | H | $CF_3$ |
| 123 | $CH_2CH_2$ | $CH_2$ | H | $CH_2CH_3$ | H | F | $CF_3$ | H | H |
| 124 | $CH_2CH_2$ | $CH_2$ | H | $CH_2CH_3$ | H | H | $CF_3$ | H | F |
| 125 | $CH_2CH_2$ | $CH_2$ | H | $CH_2CH_3$ | H | H | Cl | H | H |
| 126 | $CH_2CH_2$ | $CH_2$ | $CH_2CH_3$ | H | H | F | H | H | H |
| 127 | $CH_2CH_2$ | $CH_2$ | $CH_2CH_3$ | H | H | F | F | H | H |
| 128 | $CH_2CH_2$ | $CH_2$ | $CH_2CH_3$ | H | H | F | H | H | F |
| 129 | $CH_2CH_2$ | $CH_2$ | $CH_2CH_3$ | H | H | H | F | H | H |
| 130 | $CH_2CH_2$ | $CH_2$ | $CH_2CH_3$ | H | H | H | F | H | F |

TABLE 1-continued

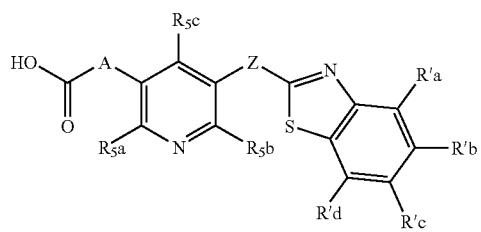

IA

| Example number | A | Z | R5a | R5b | R5c | R'a | R'b | R'c | R'd |
|---|---|---|---|---|---|---|---|---|---|
| 131 | CH$_2$CH$_2$ | CH$_2$ | CH$_2$CH$_3$ | H | H | H | H | F | F |
| 132 | CH$_2$CH$_2$ | CH$_2$ | CH$_2$CH$_3$ | H | H | H | CF$_3$ | H | H |
| 133 | CH$_2$CH$_2$ | CH$_2$ | CH$_2$CH$_3$ | H | H | H | H | H | CF$_3$ |
| 134 | CH$_2$CH$_2$ | CH$_2$ | CH$_2$CH$_3$ | H | H | F | CF$_3$ | H | H |
| 135 | CH$_2$CH$_2$ | CH$_2$ | CH$_2$CH$_3$ | H | H | H | CF$_3$ | H | F |
| 136 | CH$_2$CH$_2$ | CH$_2$ | CH$_2$CH$_3$ | H | H | H | Cl | H | H |
| 137 | CH$_2$ | CH$_2$CH$_2$ | H | CH$_2$CH$_3$ | H | F | H | H | H |
| 138 | CH$_2$ | CH$_2$CH$_2$ | H | CH$_2$CH$_3$ | H | F | F | H | H |
| 139 | CH$_2$ | CH$_2$CH$_2$ | H | CH$_2$CH$_3$ | H | F | H | H | F |
| 140 | CH$_2$ | CH$_2$CH$_2$ | H | CH$_2$CH$_3$ | H | H | F | H | H |
| 141 | CH$_2$ | CH$_2$CH$_2$ | H | CH$_2$CH$_3$ | H | H | F | F | H |
| 142 | CH$_2$ | CH$_2$CH$_2$ | H | CH$_2$CH$_3$ | H | H | F | H | F |
| 143 | CH$_2$ | CH$_2$CH$_2$ | H | CH$_2$CH$_3$ | H | H | H | F | F |
| 144 | CH$_2$ | CH$_2$CH$_2$ | H | CH$_2$CH$_3$ | H | H | CF$_3$ | H | H |
| 145 | CH$_2$ | CH$_2$CH$_2$ | H | CH$_2$CH$_3$ | H | H | H | H | CF$_3$ |
| 146 | CH$_2$ | CH$_2$CH$_2$ | H | CH$_2$CH$_3$ | H | F | CF$_3$ | H | H |
| 147 | CH$_2$ | CH$_2$CH$_2$ | H | CH$_2$CH$_3$ | H | H | CF$_3$ | H | F |
| 148 | CH$_2$ | CH$_2$CH$_2$ | H | CH$_2$CH$_3$ | H | H | Cl | H | H |
| 149 | CH$_2$ | CH$_2$CH$_2$ | CH$_2$CH$_3$ | H | H | F | H | H | H |
| 150 | CH$_2$ | CH$_2$CH$_2$ | CH$_2$CH$_3$ | H | H | F | F | H | H |
| 151 | CH$_2$ | CH$_2$CH$_2$ | CH$_2$CH$_3$ | H | H | F | H | H | F |
| 152 | CH$_2$ | CH$_2$CH$_2$ | CH$_2$CH$_3$ | H | H | H | F | H | H |
| 153 | CH$_2$ | CH$_2$CH$_2$ | CH$_2$CH$_3$ | H | H | H | F | H | F |
| 154 | CH$_2$ | CH$_2$CH$_2$ | CH$_2$CH$_3$ | H | H | F | F | H | F |
| 155 | CH$_2$ | CH$_2$CH$_2$ | CH$_2$CH$_3$ | H | H | H | H | F | F |
| 156 | CH$_2$ | CH$_2$CH$_2$ | CH$_2$CH$_3$ | H | H | H | CF$_3$ | H | H |
| 157 | CH$_2$ | CH$_2$CH$_2$ | CH$_2$CH$_3$ | H | H | H | H | H | CF$_3$ |
| 158 | CH$_2$ | CH$_2$CH$_2$ | CH$_2$CH$_3$ | H | H | F | CF$_3$ | H | H |
| 159 | CH$_2$ | CH$_2$CH$_2$ | CH$_2$CH$_3$ | H | H | H | CF$_3$ | H | F |
| 160 | CH$_2$ | CH$_2$CH$_2$ | CH$_2$CH$_3$ | H | H | H | Cl | H | H |
| 161 | CH(CH$_3$) | CH$_2$ | CH$_2$CH$_3$ | H | H | F | F | H | F |
| 162 | CH(CH$_3$) | CH$_2$ | H | CH$_2$CH$_3$ | H | F | F | H | F |
| 163 | CH(CH$_3$) | CH$_2$ | CH$_3$ | H | H | F | F | H | F |
| 164 | CH(CH$_3$) | CH$_2$ | H | CH$_3$ | H | F | F | H | F |
| 165 | CH(CH$_3$) | CH$_2$ | OH | H | H | F | F | H | F |
| 166 | CH(CH$_3$) | CH$_2$ | H | OH | H | F | F | H | F |
| 167 | CH$_2$ | CH(CH$_3$) | CH$_2$CH$_3$ | H | H | F | F | H | F |
| 168 | CH$_2$ | CH(CH$_3$) | H | CH$_2$CH$_3$ | H | F | F | H | F |
| 169 | CH$_2$ | CH(CH$_3$) | CH$_3$ | H | H | F | F | H | F |
| 170 | CH$_2$ | CH(CH$_3$) | H | CH$_3$ | H | F | F | H | F |
| 171 | CH$_2$ | CH(CH$_3$) | OH | H | H | F | F | H | F |
| 172 | CH$_2$ | CH(CH$_3$) | H | OH | H | F | F | H | F |
| 173 | CH$_2$ | CH$_2$ | CH$_2$CH$_3$ | H | F | F | F | H | F |
| 174 | CH$_2$ | CH$_2$ | H | CH$_2$CH$_3$ | F | F | F | H | F |
| 175 | CH$_2$ | CH$_2$ | CH$_2$CH$_3$ | H | CH$_3$ | F | F | H | F |
| 176 | CH$_2$ | CH$_2$ | H | CH$_2$CH$_3$ | CH$_3$ | F | F | H | F |
| 177 | CH$_2$ | CH$_2$ | CH$_2$CF$_3$ | H | H | F | F | H | F |
| 178 | CH$_2$ | CH$_2$ | H | CH$_2$CF$_3$ | H | F | F | H | F |
| 179 | CH$_2$ | CH$_2$ | CH$_2$F | H | H | F | F | H | F |
| 180 | CH$_2$ | CH$_2$ | H | CH$_2$F | H | F | F | H | F |
| 181 | CH$_2$ | CH$_2$ | CH$_2$CH$_2$F | H | H | F | F | H | F |
| 182 | CH$_2$ | CH$_2$ | H | CH$_2$CH$_2$F | H | F | F | H | F |
| 183 | CH$_2$ | CH$_2$ | NHCH$_3$ | H | H | F | F | H | F |
| 184 | CH$_2$ | CH$_2$ | H | NHCH$_3$ | H | F | F | H | F |
| 185 | CH$_2$ | CH$_2$ | N(CH$_3$)$_2$ | H | H | F | F | H | F |
| 186 | CH$_2$ | CH$_2$ | H | N(CH$_3$)$_2$ | H | F | F | H | F |
| 187 | CH$_2$ | CH$_2$ | NHEt | H | H | F | F | H | F |
| 188 | CH$_2$ | CH$_2$ | H | NHEt | H | F | F | H | F |

EXAMPLE 189

Representative compounds of the invention are tested for their potency, selectivity and efficacy as inhibitors of human aldose reductase. The potency or aldose reductase inhibiting effects of the compounds are tested using methods similar to those described by Butera et al. in *J. Med. Chem.* 1989, 32, 757. Using this assay, the concentrations required to inhibit human aldose reductase (hALR2) activity by 50% (IC50) are determined.

Optionally, in a second assay, a number of the same compounds can be tested for their ability to inhibit aldehyde reductase (hALR1), a structurally related enzyme. The test method employed is essentially that described by Ishii, et al., *J. Med. Chem.* 1996 39: 1924. Using this assay, the concentrations required to inhibit human aldehyde reductase activity by 50% (IC50) can be determined.

From these data, the hALR1:hALR2 ratios can be determined. Since high potency of test compounds as inhibitors of aldose reductase is desirable, low hALR2 $IC_{50}$ values are sought. On the other hand, high potency of test compounds as inhibitors of aldehyde reductase is undesirable, and high hALR1 $IC_{50}$s values are sought. Accordingly, the hALR1:hALR2 ratio can be used to determine the selectivity of the test compounds. The importance of this selectivity is described in Kotani, et al., *J. Med. Chem.* 40: 684, 1997.

The ability of representative compounds of the invention to inhibit aldose reductase is illustrated in Table 2.

TABLE 2

| Example number | Name | hAR-#1 (aldose) |
|---|---|---|
| 1 | [6-Ethyl-3-(4,5,7-trifluoro-benzothiazol-2-ylmethyl)-pyrrolo[2,3-b]pyridin-1-yl]-acetic acid | 12 nM |
| 2 | [6-Methyl-3-(4,5,7-trifluoro-benzothiazol-2-ylmethyl)-pyrrolo[2,3-b]pyridin-1-yl]-acetic acid | 8 nM |
| 3 | [3- (4,5,7-Trifluoro-benzothiazol-2-ylmethyl)-pyrrolo[2,3-b]pyridin-1-yl]-acetic acid | 7 nM |
| 4 | [2,6-Dimethyl-5-(4,5,7-trifluoro-benzothiazol-2-ylmethyl)-pyridin-3-yl]-acetic acid | 4 nM |
| 5 | [2,6-Diethyl-5-(4,5,7-trifluoro-benzothiazol-2-ylmethyl)-pyridin-3-yl]-acetic acid | 7 nM |
| 6 | [2,6-Diphenyl-5-(4,5,7-trifluoro-benzothiazol-2-ylmethyl) -pyridin-3-yl]-acetic acid | 11 nM |
| 7 | [2,6-Dipropyl-5-(4,5,7-trifluoro-benzothiazol-2-ylmethyl)-pyridin-3-yl]-acetic acid | 7 nM |
| 8 | [5-(4,5,7-Trifluoro-benzothiazol-2-ylmethyl)-pyridin-3-yl]-acetic acid | 8 nM |
| 9 | [2,4,6-Trimethyl-5-(4,5,7-trifluoro-benzothiazol-2-ylmethyl)-pyridin-3-yl]-acetic acid | 6 nM |
| 10 | [4-Ethyl-2, 6-dimethyl-5-(4,5,7-trifluoro-benzothiazol-2-ylmethyl)-pyridin-3-yl]-acetic acid | 31 nM |
| 11 | [2-Ethyl-5-(4,5,7-trifluoro-benzothiazol-2-ylmethyl)-pyridin-3-yl]-acetic acid | 6 nM |
| 12 | [2-Benzyl-5-(4,5,7-trifluoro-benzothiazol-2-ylmethyl)-pyridin-3-yl]-acetic acid | 5 nM |
| 13 | [2-Phenyl-5-(4,5,7-trifluoro-benzothiazol-2-ylmethyl)-pyridin-3-yl]-acetic acid | 8 nM |
| 14 | [6-Ethyl-5-(4,5,7-trifluoro-benzothiazol-2-ylmethyl)-pyridin-3-yl]-acetic acid | 7 nM |
| 15 | [6-Phenyl-5-(4,5,7-trifluoro-benzothiazol-2-ylmethyl)-pyridin-3-yl]-acetic acid | 6 nM |
| 16 | [6-Benzyl-5-(4,5,7-trifluoro-benzothiazol-2-ylmethyl)-pyridin-3-yl]-acetic acid | 7 nM |
| 17 | [2-Phenoxy-5-(4,5,7-trifluoro-berizothiazol-2-ylmethyl)-pyridin-3-yl]-acetic acid | |
| 18 | [5-(4,5,7-Trifluoro-benzothiazol-2-ylmethyl) -thiophen-2-yl]-acetic acid | 27 nM |
| 19 | [3-Methyl-4-(4,5,7-trifluoro-berizothiazol-2-ylmethyl)-thiophen-2-yl]-acetic acid | 270 nM |
| 20 | [4-(4,5,7-Trifluoro-berizothiazol-2-ylmethyl)-thiophen-2-yl]-acetic acid | 9 nM |
| 21 | [2-(4,5,7-Trifluoro-benzothiazol-2-ylmethyl)-thiophen-3-yl]-acetic acid | 24 nM |
| 22 | [4-Methyl-5-(4,5,7-trifluoro-benzothiazol-2-ylmethyl)-thiophen-3-yl]-acetic acid | 31 nM |
| 23 | [5-(4,5,7-Trifluoro-benzothiazol-2-ylmethyl)-thiophen-3-yl]-acetic acid | 27 nM |
| 24 | [2,5-Dimethyl-4-(4,5,7-trifluoro-benzothiazol-2-ylmethyl)-thiophen-3-yl]-acetic acid | 36 nM |
| 25 | [2-(4,5,7-Trifluoro-benzothiazol-2-ylmethyl)-thiazol-4-yl]-acetic acid | 130 nM |

The results show the superior potency of representative compounds of the invention. Such compounds are useful in the treatment of chronic complications arising from diabetes mellitus, such as diabetic cataracts, retinopathy and neuropathy. Accordingly, an aspect of the invention is treatment of such complications with the inventive compounds; treatment includes both prevention and alleviation. The compounds are useful in the treatment of, for example, diabetic cataracts, retinopathy, nephropathy and neuropathy.

In a third, optional, set of experiments, the compounds can be assayed for their ability to normalize or reduce sorbitol accumulation in the sciatic nerve of streptozotocin-induced diabetic rats. The test methods employed to determine the efficacy are essentially those of Mylari, et al., *J. Med. Chem.* 34: 108, 1991.

EXAMPLE 190

Uricosuric Activity in the Chimpanzee

Compound of Example 14 was administered to chimpanzees orally as a single 4 mg/kg does. While four animals were dosed, complete data was not collected for one animal (Chimp #4), as an adverse reaction to anesthesia required early termination of this animal from the study. Data from the remaining three animals shows a clear uricosuric effect of this compound. On average, a maximal lowering of blood uric acid levels of about 44% was observed at approximately 12 hours following dosage in all animals (Table 1). Uric acid data for the urine (Table 2) shows a concomitant increase in the urinary excretion of uric acid over the first 24 hours following dosage. These data suggest the observed drop of uric acid concentration in the blood was a result of the enhanced urinary excretion of uric acid. Thus, this data demonstrates that the compound of Example 14 is a potent uricosuric agent.

TABLE 1

Concentrations of uric acid in serum drawn at various times following a single oral 4 mg/kg dose of compound of Example 14 in the Chimpanzee.

| Time (hours) | Chimp #1 mg/dL | Chimp #2 mg/dL | Chimp #3 mg/dL | Chimp #4 mg/dL | mean mg/dL | s.dev | cv |
|---|---|---|---|---|---|---|---|
| Baseline | 2.9 | 1.9 | 2.3 | 2.5 | 2.4 | 0.4 | 15 |
| 0 | 3.0 | 1.7 | 2.2 | 2.5 | 2.4 | 0.5 | 20 |
| 0.25 | 3.0 | 1.8 | 2.3 | 2.6 | 2.4 | 0.4 | 18 |
| 0.50 | 3.0 | 1.8 | 2.3 | 2.5 | 2.4 | 0.4 | 18 |
| 1.0 | 3.0 | 1.8 | 2.1 | 2.7 | 2.4 | 0.5 | 20 |
| 2.0 | 2.8 | 1.7 | 1.9 | 2.3 | 2.2 | 0.4 | 19 |
| 6.0 | 2.2 | 1.2 | 1.6 | 1.8 | 1.7 | 0.4 | 21 |
| 12 | 1.9 | 0.9 | 1.6 | 1.7 | 1.5 | 0.4 | 25 |
| 24 | 2.3 | 1.4 | 1.9 | N/D | 1.9 | 0.4 | 20 |
| 48 | 3.4 | 1.2 | 1.9 | N/D | 2.2 | 0.9 | 42 |
| 72 | 3.2 | 1.4 | 2.4 | N/D | 2.3 | 0.7 | 32 |

TABLE 2

Amount of uric acid excreted in the urine in 24 hour intervals following a single oral 4 mg/kg dose of compound of Example 14 in the Chimpanzee.

| Time Hours | Chimp #1 mg | Chimp #2 mg | Chimp #3 mg | Chimp #4 mg | mean mg | s.dev | cv |
|---|---|---|---|---|---|---|---|
| Baseline | 321 | 474 | 347 | 450 | 398 | 65 | 16 |
| 0-24 | 1020 | 758 | 843 | N/D | 874 | 109 | 12 |
| 24-48 | 686 | 399 | 189 | N/D | 425 | 204 | 48 |
| 48-72 | 657 | 290 | 216 | N/D | 388 | 193 | 50 |

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula

D-A-C(O)R' or a pharmaceutically acceptable salt thereof wherein D represents

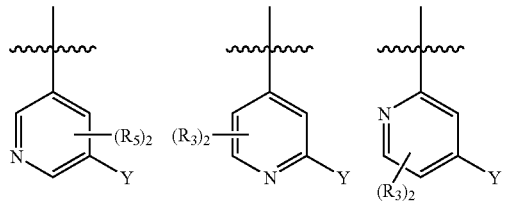

or

-continued

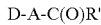

where

Y is -Z-Ar where

Z is a bond, O, S, C(O)NH, or $C_1$-$C_6$ alkylene optionally substituted with $C_1$-$C_2$ alkyl; and Ar represents benzothiazolyl or benzothiazolyl($C_1$-$C_6$)alkyl, where the benzothiazolyl portion is optionally substituted by one, two or three groups independently selected from (1) halogen, ($C_1$-$C_6$)alkyl, hydroxy, ($C_1$-$C_6$)haloalkyl, ($C_2$-$C_6$)haloacetyl, cyano, nitro, ($C_1$-$C_6$)alkanoyl, ($C_1$-$C_6$)alkylthio, ($C_1$-$C_6$)haloalkylthio, $OR_{27}$, $SR_{27}$, $S(O)R_{27}$, $S(O)_2R_{27}$ and $N(R_{27})_2$ wherein each $R_{27}$ is independently hydrogen, $C_1$-$C_6$ alkyl, $C_1$-$C_6$ haloalkyl, or $C_1$-$C_6$ haloalkoxy; and (2) phenyl, pyridyl, furyl, and thienyl, each of which is optionally substituted with one, two, or three groups independently selected from halogen, ($C_1$-$C_6$)alkyl, hydroxy, halogen, ($C_1$-$C_6$)haloalkyl, ($C_2$-$C_6$)haloacetyl, cyano, nitro, ($C_1$-$C_6$)alkanoyl, ($C_1$-$C_6$)alkylthio, ($C_1$-$C_6$)haloalkylthio, $OR_{37}$, $SR_{37}$, $S(O) R_{37}$, $S(O)2R_{37}$ and $N(R_{37})_2$ wherein each $R_{37}$ is independently hydrogen, $C_1$-$C_6$ alkyl, $C_1$-$C_6$ haloalkyl, or $C_1$-$C_6$ haloalkoxy;

$R_3$ is hydrogen, halogen, hydroxy, ($C_1$-$C_6$)alkyl, ($C_1$-$C_6$)haloalkyl, amino, ($C_1$-$C_6$)alkylamino, di($C_1$-$C_6$)alkylamino, aryl, —$SR_{15}$ or —$OR_{15}$, where $R_{15}$ is ($C_1$-$C_6$)alkyl, aryl, or aryl($C_1$-$C_6$)alkyl where each aryl is optionally mono-, di-, or trisubstituted with halogen, ($C_1$-$C_6$)alkyl, hydroxy, halogen, ($C_1$-$C_6$)haloalkyl, ($C_2$-$C_6$)haloacetyl, cyano, nitro, ($C_1$-$C_6$)alkanoyl, ($C_1$-$C_6$)alkylthio, ($C_1$-$C_6$)haloalkylthio, $OR_7$, $SR_7$, $S(O)R_7$, $S(O)_2R_7$, and $N(R_7)_2$, $R_5$ represents hydrogen, halogen, hydroxy, ($C_1$-$C_6$)alkoxy, ($C_1$-$C_6$)alkyl, halo($C_1$-$C_6$)alkyl, hydroxy, amino, mono or di($C_1$-$C_6$)alkylamino, or aryl where aryl is optionally substituted with up to three groups independently selected from halogen, $(C_1-C_6)$alkyl, hydroxy, halogen, $(C_1-C_6)$haloalkyl, $(C_2-C_6)$haloacetyl, cyano, nitro, $(C_1-C_6)$alkanoyl, $(C_1-C_6)$alkylthio, $(C_1-C_6)$haloalkylthio, $OR_7$, $SR_7$, $S(O)R_7$, $S(O)_2R_7$ and $N(R_7)_2$;

each $R_7$ is independently hydrogen, $C_1-C_6$ alkyl, $C_1-C_6$ haloalkyl, or $C_1-C_6$ haloalkoxy;

A is a $C_1-C_4$ alkylene group optionally substituted with $C_1-C_2$ alkyl or mono- or disubstituted with halogen; and R' is hydroxy, benzyloxy, di($C_1-C_6$)alkylaminoethyloxy, acetoxymethyl, pivaloyloxymethyl, phthalidoyl, ethoxycarbonyloxyethyl, 5-methyl-2-oxo-1,3-dioxol-4-yl methyl, or $(C_1-C_6)$alkoxy optionally substituted by N-morpholino or di($C_1-C_6$)alkylamino.

2. A compound according to claim 1, wherein Z is $(C_1-C_6)$alkylene and Ar is a substituted benzothiazole of Formula III

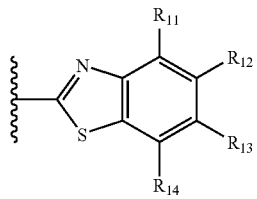

wherein $R_{11}$, $R_{12}$, $R_{13}$ and $R_{14}$ are independently hydrogen, halogen, $(C_1-C_6)$alkyl, halogen, $(C_1-C_6)$haloalkyl, $(C_2-C_6)$haloacetyl, cyano, nitro, $(C_1-C_6)$alkanoyl, $(C_1-C_6)$alkylthio, $(C_1-C_6)$haloalkylthio, $OR_7$, $SR_7$, $S(O)R_7$, $S(O)_2R_7$ or $N(R_7)$.

3. A compound according to claim 2, wherein $R_{11}$, $R_{12}$, $R_{13}$ and $R_{14}$ are independently hydrogen, hydroxy, $(C_1-C_6)$alkoxy, halogen, $(C_1-C_6)$alkyl, halogen, $(C_1-C_6)$haloalkyl, cyano, nitro, or $N(R_7)_2$ wherein each $R_7$ is independently hydrogen or $C_1-C_6$ alkyl.

4. A compound according to claim 3, wherein $R_{11}$, $R_{12}$, $R_{13}$ and $R_{14}$ are independently hydrogen, fluorine, chlorine, bromine, trifluoromethyl or nitro.

5. A compound according to claim 3, wherein Z is $(C_1-C_3)$alkylene.

6. A compound according to claim 5, wherein A and Z are both methylene.

7. A compound according to claim 6, wherein R' is hydroxy or $C_1-C_6$ alkoxy.

8. A compound according to claim 7 where each $R_3$ is independently hydrogen, $C_1-C_6$ alkyl, or phenyl($C_1-C_6$) alkyl where the phenyl portion is optionally substituted with one, two or three groups independently selected from halogen, hydroxy, $C_1-C_6$ alkyl, amino, $(C_1-C_6)$alkylamino, and di($C_1-C_6$)alkylamino.

9. A compound according to claim 7, where D is

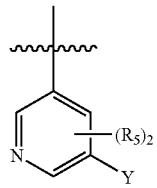

where each $R_5$ is independently hydrogen, $C_1-C_6$ alkyl, $C_1-C_6$ alkoxy, amino, mono- or di($C_1-C_6$)alkylamino, or phenyl($C_1-C_6$)alkyl, phenoxy or phenyl where each phenyl portion is optionally mono, di, or trisubstituted with independently selected hydroxy, halogen, $C_1-C_6$ alkyl, $C_1-C_6$ alkoxy, amino, or mono- or di($C_1-C_6$)alkylamino groups.

10. A compound according to claim 9, wherein D is

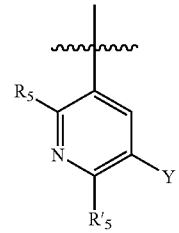

where $R_5$ and $R_5'$ independently represent hydrogen, $C_1-C_6$ alkyl, $C_1-C_6$ alkoxy, or phenyl($C_1-C_6$)alkyl, phenoxy or phenyl where each phenyl portion is optionally substituted with one or two independently selected hydroxy, halogen, $C_1-C_6$ alkyl, or $C_1-C_6$ alkoxy groups.

11. A compound according to claim 5, wherein $R_{11}$, $R_{12}$, $R_{13}$ and $R_{14}$ are independently hydrogen, hydroxy, $(C_1-C_2)$alkoxy, trifluoromethyl, $(C_1-C_3)$alkyl, fluoro, chloro, bromo, nitro, amino, mono($C_1-C_2$)alkylamino or di($C_1-C_2$)alkylamino.

12. A compound according to claim 5, wherein $R_{11}$, $R_{12}$, $R_{13}$ and $R_{14}$ are independently hydrogen, hydroxy, fluoro, chloro, nitro, or amino.

13. A compound according to claim 5, wherein three of $R_{11}$, $R_{12}$, $R_{13}$ and $R_{14}$ are fluoro and the other is hydrogen.

14. A compound according to claim 5 where at least one of $R_{11}$, $R_{12}$, $R_{13}$, and $R_{14}$ is trifluoromethyl.

15. A compound according to claim 10, wherein $R_{12}$ is trifluoromethyl.

16. A compound according to claim 7, wherein $R_{11}$, $R_{12}$, and $R_{14}$ represent fluorine and $R_{13}$ is hydrogen.

17. A compound according to claim 14, wherein $R_{11}$, $R_{12}$, and $R_{14}$ represent fluorine and $R_{13}$ is hydrogen.

18. A compound according to claim 5, wherein R' is hydroxy.

19. A compound according to claim 5, wherein R' is $C_1-C_6$ alkoxy.

20. A compound according to claim 1, which is [2,6-Dimethyl-5-(4,5,7-trifluoro-benzothiazol-2-ylmethyl)-pyridin-3-yl]-acetic acid.

21. A compound according to claim 1, which is [2,6-Diethyl-5-(4,5,7-trifluoro-benzothiazol-2-ylmethyl)-pyridin-3-yl]-acetic acid.

22. A compound according to claim 1, which is [2,6-Diphenyl-5-(4,5,7-trifluoro-benzothiazol-2-ylmethyl)-pyridin-3-yl]-acetic acid.

23. A compound according to claim 1, which is [2,6-Dipropyl-5-(4,5,7-trifluoro-benzothiazol-2-ylmethyl)-pyridin-3-yl]-acetic acid.

24. A compound according to claim 1, which is [5-(4,5,7-Trifluoro-benzothiazol-2-ylmethyl)-pyridin-3-yl]-acetic acid.

25. A compound according to claim 1, which is [2,4,6-Trimethyl-5-(4,5,7-trifluoro-benzothiazol-2-ylmethyl)-pyridin-3-yl]-acetic acid.

26. A compound according to claim 1, which is [4-Ethyl-2,6-dimethyl-5-(4,5,7-trifluoro-benzothiazol-2-ylmethyl)-pyridin-3-yl]-acetic acid.

27. A compound according to claim 1, which is [2-Ethyl-5-(4,5,7-trifluoro-benzothiazol-2-ylmethyl)-pyridin-3-yl]-acetic acid.

28. A compound according to claim 1, which is [2-Benzyl-5-(4,5,7-trifluoro-benzothiazol-2-ylmethyl)-pyridin-3-yl]-acetic acid.

29. A compound according to claim 1, which is [2-Phenyl-5-(4,5,7-trifluoro-benzothiazol-2-ylmethyl)-pyridin-3-yl]-acetic acid.

30. A compound according to claim 1, which is [6-Ethyl-5-(4,5,7-trifluoro-benzothiazol-2-ylmethyl)-pyridin-3-yl]-acetic acid.

31. A compound according to claim 1, which is [6-Phenyl-5-(4,5,7-trifluoro-benzothiazol-2-ylmethyl)-pyridin-3-yl]-acetic acid.

32. A compound according to claim 1, which is [6-Benzyl-5-(4,5,7-trifluoro-benzothiazol-2-ylmethyl)-pyridin-3-yl]-acetic acid.

33. A compound according to claim 1, which is [2-Phenoxy-5-(4,5,7-trifluoro-benzothiazol-2-ylmethyl)-pyridin-3-yl]-acetic acid.

34. A method of alleviating chronic complications arising from diabetes mellitus, where the chronic complications are selected from the group consisting of diabetic cataracts, retinopathy, nephropathy and neuropathy, which method comprises administering to a mammal in need of such treatment a therapeutically effective amount of a compound according to claim 1.

35. A method for reducing serum uric acid levels, wherein the method comprises administering to a mammal in need of such treatment a therapeutically effective amount of a compound of claim 1.

36. A method for treating gout, wherein the method comprises administering to a mammal in need of such treatment a therapeutically effective amount of a compound of claim 1.

\* \* \* \* \*